United States Patent
Szakács et al.

(10) Patent No.: US 10,744,127 B2
(45) Date of Patent: Aug. 18, 2020

(54) MDR-REVERSING 8-HYDROXY-QUINOLINE DERIVATIVES

(71) Applicant: MAGYAR TUDOMÁNYOS AKADÉMIA TERMÉSZETTUDOMÁNYI KUTATÓKÖZPONT, Budapest (HU)

(72) Inventors: Gergely Szakács, Budapest (HU); Tibor Soós, Budapest (HU); Roberta Ferenczi-Palkó, Budapest (HU); András Füredi, Budapest (HU); Szilárd Tóth, Jászapáti (HU); Dóra Türk, Budapest (HU); Veronika Pape, Unna (DE); Ferenc Fülöp, Szeged (HU); István Szatmári, Szeged (HU); György Dormán, Piliscsaba (HU)

(73) Assignee: Magyar Tudományos Akadémia Természettudományi Kutatóközpont, Budapest (HU)

(*) Notice: Subject to any disclaimer, the term of this patent is extended or adjusted under 35 U.S.C. 154(b) by 0 days.

(21) Appl. No.: 16/091,134

(22) PCT Filed: Apr. 5, 2017

(86) PCT No.: PCT/HU2017/050009
§ 371 (c)(1),
(2) Date: Oct. 4, 2018

(87) PCT Pub. No.: WO2017/175018
PCT Pub. Date: Oct. 12, 2017

(65) Prior Publication Data
US 2019/0151306 A1 May 23, 2019

(30) Foreign Application Priority Data
Apr. 5, 2016 (HU) .................... 1600234

(51) Int. Cl.
| | | |
|---|---|---|
| A61K 31/4709 | (2006.01) |
| C07D 215/38 | (2006.01) |
| C07D 401/04 | (2006.01) |
| C07D 401/12 | (2006.01) |
| C07D 417/12 | (2006.01) |
| C07D 471/04 | (2006.01) |
| C07D 495/04 | (2006.01) |
| A61K 45/06 | (2006.01) |
| A61K 31/47 | (2006.01) |
| C07D 215/36 | (2006.01) |
| C07D 401/14 | (2006.01) |
| A61P 35/04 | (2006.01) |
| A61K 31/4704 | (2006.01) |
| A61K 31/4725 | (2006.01) |
| A61K 31/498 | (2006.01) |
| C07D 215/28 | (2006.01) |

(52) U.S. Cl.
CPC .......... *A61K 31/4709* (2013.01); *A61K 31/47* (2013.01); *A61K 31/4704* (2013.01); *A61K 31/4725* (2013.01); *A61K 31/498* (2013.01); *A61K 45/06* (2013.01); *A61P 35/04* (2018.01); *C07D 215/28* (2013.01); *C07D 215/36* (2013.01); *C07D 215/38* (2013.01); *C07D 401/04* (2013.01); *C07D 401/12* (2013.01); *C07D 401/14* (2013.01); *C07D 417/12* (2013.01); *C07D 471/04* (2013.01); *C07D 495/04* (2013.01)

(58) Field of Classification Search
CPC ............. A61K 31/4709; C07D 215/02; C07D 401/06; C07D 401/14
USPC ............................... 514/312; 546/256, 268.1
See application file for complete search history.

(56) References Cited

U.S. PATENT DOCUMENTS

| | | |
|---|---|---|
| 2,681,910 A | 6/1954 | Burckhalter |
| 2008/0214606 A1 | 9/2008 | Szakacs et al. |
| 2010/0316655 A1 | 12/2010 | Hall et al. |
| 2011/0301163 A1 | 12/2011 | Liu et al. |

(Continued)

FOREIGN PATENT DOCUMENTS

| | | | |
|---|---|---|---|
| FR | 2160718 | * 6/1973 | ............. A61K 27/00 |
| FR | 2.160.718 A1 | 7/1973 | |
| WO | 96/09291 A1 | 3/1996 | |

(Continued)

OTHER PUBLICATIONS

Skalli, et. al., Quimica Analitica (Barcelona) (1998), 17(2), 83-88.*
Dardqari, et. al., Farmaco (2004), 59(3), 195-199.*
Türk et al.: "Identification of compounds selectively killing multidrug resistant cancer cells", Cancer Res., 2009; vol. 69: (21), pp. 8293-8301.
Sosic et al.: "Development of New Cathespin B Inhibitors: Combining Bioisosteric Replacements and Structure-Based Design to Explore the Structure—Activity Relationships of Nitroxoline Derivatives", J. Med. Chem., 2013, vol. 56, pp. 521-533.

(Continued)

*Primary Examiner* — Jeffrey H Murray
(74) *Attorney, Agent, or Firm* — Jason D. Voight

(57) ABSTRACT

The present invention is related to 8-hydroxy-quinoline derivatives having multidrug-resistance reversing activity with improved selectivity and increased cytotoxicity towards multidrug-resistant cancer cells, preparation thereof and use of the same in the treatment of cancer, especially multidrug-resistant variants thereof.

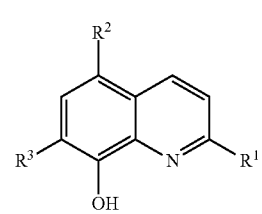

(1)

15 Claims, 4 Drawing Sheets

(56) References Cited

U.S. PATENT DOCUMENTS

2013/0131096 A1    5/2013    Puskas et al.
2015/0306081 A1    10/2015    Richardson et al.

FOREIGN PATENT DOCUMENTS

| WO | 2010/138686 A1 | 12/2010 |
| WO | 2012/033601 A1 | 3/2012 |
| WO | 2012/058269 A2 | 5/2012 |

OTHER PUBLICATIONS

Mohammed et al.: "8-Hydroxyquinoline-based inhibitors of the Rce1 protease disrupt Ras membrane localization in human cells", Bioorg. Med. Chem., 2016, vol. 24, pp. 160-178.

Database Registry: "7-[[[(3,4-dichlorophenyl)methyl]amino]methyl]-8-quinolinol", Chemical Abstracts Service, 2003, accession No. 501655-04-5, XP-002770661.

Chemistry Database: "7-[(benzylamino)methyl]-5-fluoroquinolin-8-ol", PubChem CID 20667449, 2007, XP055377184.

Sakee et al.: "First Synthesis of 5-Chloro-7-[1,3]oxazolo[4,5-b]pyridin-2-ylquinolin-8-ol by Pd-Catalyzed Arylation", Synthetic Communications, 2009, vol. 39, pp. 3031-3037.

Szatmári et al.: "Solvent-Free Synthesis of 1-Hydroxyquinolyl)- and 1-(Hydroxyisoquinolyl)-1,2,3,4-tetrahydroisoquinolines by Modified Mannich Reaction", Synthesis, 2011, vol. 2011, No. 5, pp. 745-748.

Ilisz et al.: "High-performance liquid chromatographic enantioseparation of naphthol-substituted tetrahydroisoquinolines on polysaccharide-based chiral stationary phases", Biomedical Chromatography, 2013, vol. 28, pp. 142-151.

Padalkar et al.: "Excited-dtate intramolecular proton transfer (ESIPT) inspired azole-quinoline based fluorophores: Synthesis and photophysical properties study", Journal of Luminescence, 2014, vol. 155, pp. 58-64.

Khalil et al.: "Synthesis of some Oxazolo-, Imidazolo-, Selenadiazolo-, Thiadiazolo-, Azetidinono- and Thiazolidinono-8-hydroxyquinolines", Journal of the Indian Chemical Society, 1987, vol. 64, pp. 42-45.

Database Registry: "5-iodo-7-(1-piperidinylmethyl)-8-quinolinol", Chemical Abstracts Service, 2008, accession No. 1025921-59-8, XP-002774164.

Al-Yu Shen et al.: "Synthesis and Cytotoxicity Evaluation of Some 8-Hydroxyquinoline Derivatives", J. Pharm. Pharmacol., 1999, vol. 51, pp. 543-548.

Medic-Saric et al: "Nitroxoline Mannich bases: relationship between chromatographic RM values, Wiener's number and antibacterial activities", Acta Pharm. Jugosl., 1983, vol. 33, pp. 199-208.

Prati et al.: "Novel 8-Hydroxyquinoline Derivatives as Multitarget Compounds for the Treatment of Alzheimer's Disease", ChemMedChem, 2016, vol. 11, pp. 1284-1295.

Shterev et al.: "Comparative study on aminomethylation of 5-nitro-8-hydroxyquinoline", Trudove na Nauchnoizsledovatelskiya Khimikofarmatsevtichen, 1986, CAPLUS Registry Abstract, 552901.

Ghaemmaghami et al.: "Discovery of 2-Aminothiazoles as Patent Antiprion Compounds", Journal of Virology, 2010, pp. 3408-3412.

Rivera et al.: "7-(Imidazolidin-1-Ylmethyl)Quinolin-8-Ol: An Unexpected Product From a Mannich-Type Reaction in Basic Medium", Heterocycles, 2006, vol. 68, No. 3, pp. 531-537.

Burckhalter et al: "Amino- and Chloromethylation of 8-Quinolinol, Mechanism of Preponderant ortho Substitution in Phenols under Mannich Conditions", J. Org. Chem., 1961, vol. 26, pp. 4078-4083.

Türk: "Multidrog rezisztens tumorsejtek szelektív eliminására képes vegyületek azonosítása és in vitro vizsgálata", Doctoral dissertation, 2014.

Hall et al.: "Synthesis, Activity, and Pharmacophore Development for Isatin-Beta-thiosemicarbazones with Selective Activity toward Multidrug-Resistant Cells", Journal of Medicinal Chemistry, 2009, pp. A-N.

Ludwig et al.: "Selective Toxicity of NSC73306 in MDR1-Positive Cells as a New Strategy to Circumvent Multidrug Resistance in Cancer", Cancer Res, 2006, vol. 66, pp. 4808-4815.

Orina et al.::: "Evaluation of current methods used to analyze the expression profiles of ATP-binding cassette transporters yields an improved drug-discovery database", Mol Cancer Ther, 2009, vol. 8, pp. 2057-2066.

Szakács et al.: "Predicting drug sensitivity and resistance: Profiling ABC transporter genes in cancer cells", Cancer Cell, 2004, vol. 6, pp. 129-137.

\* cited by examiner

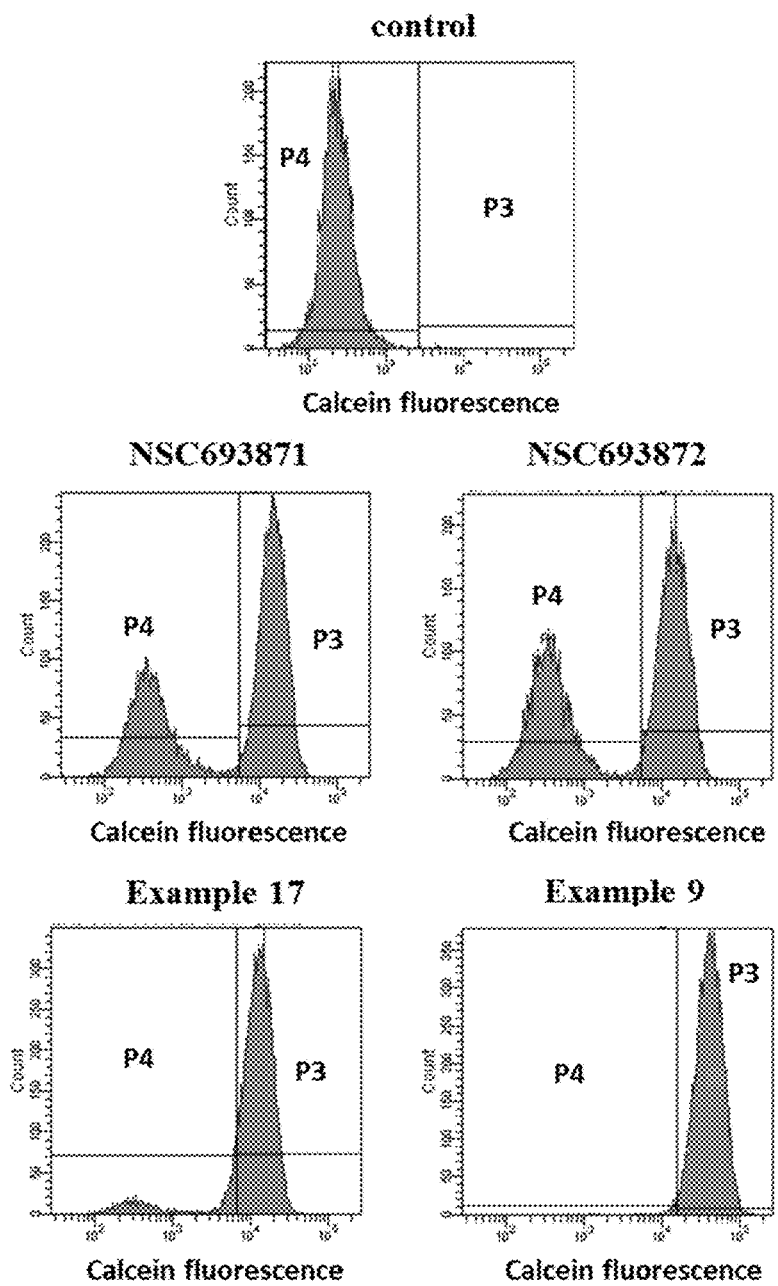
Figure 1: Fraction of P-gp-positive and -negative cells in the population after treatment with a single dose of the state of the art and two example compounds of the invention

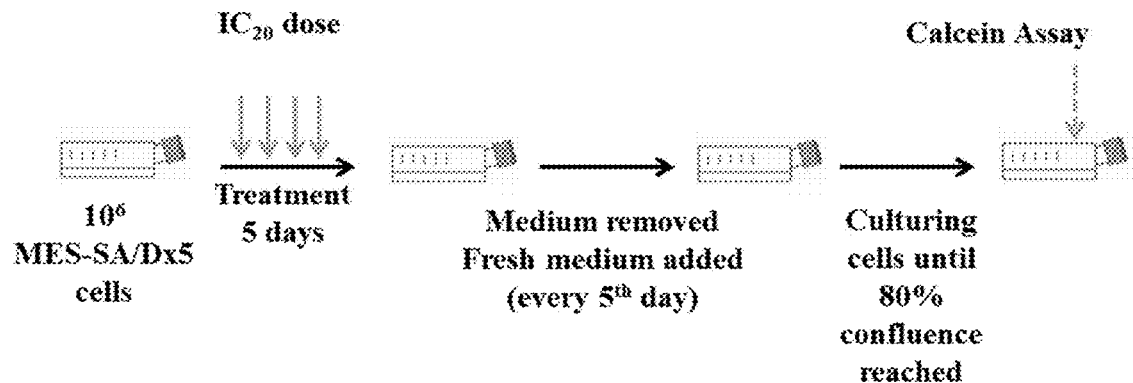
Figure 2: P-glycoprotein „switch" assay
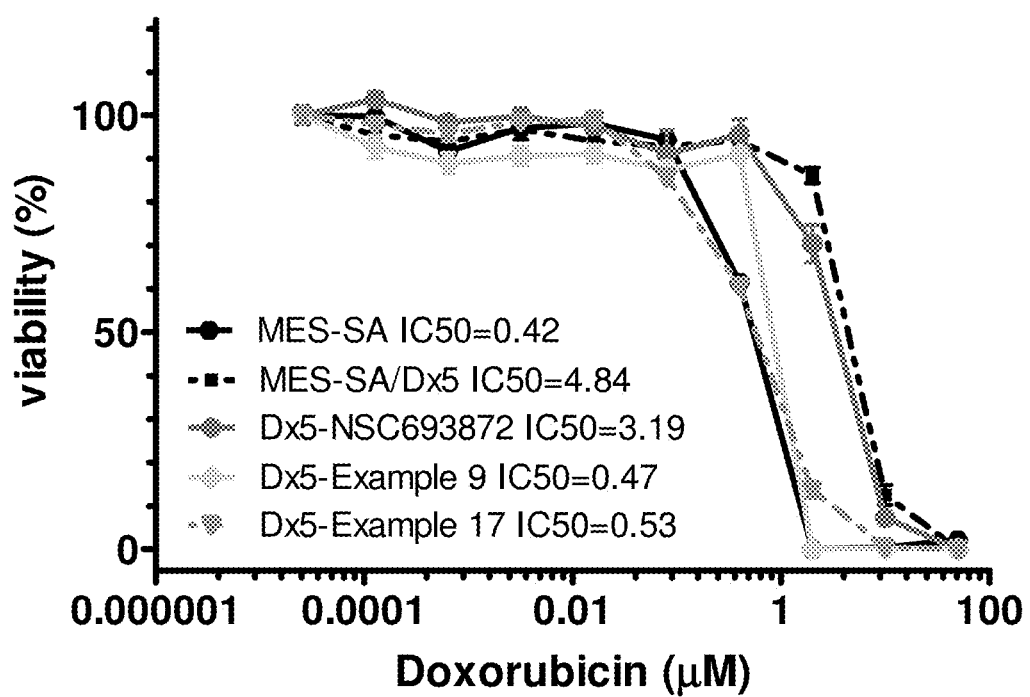
Figure 3. Renewed sensitivity of MDR cells to doxorubicin following a single treatment with the example compounds of the present invention.

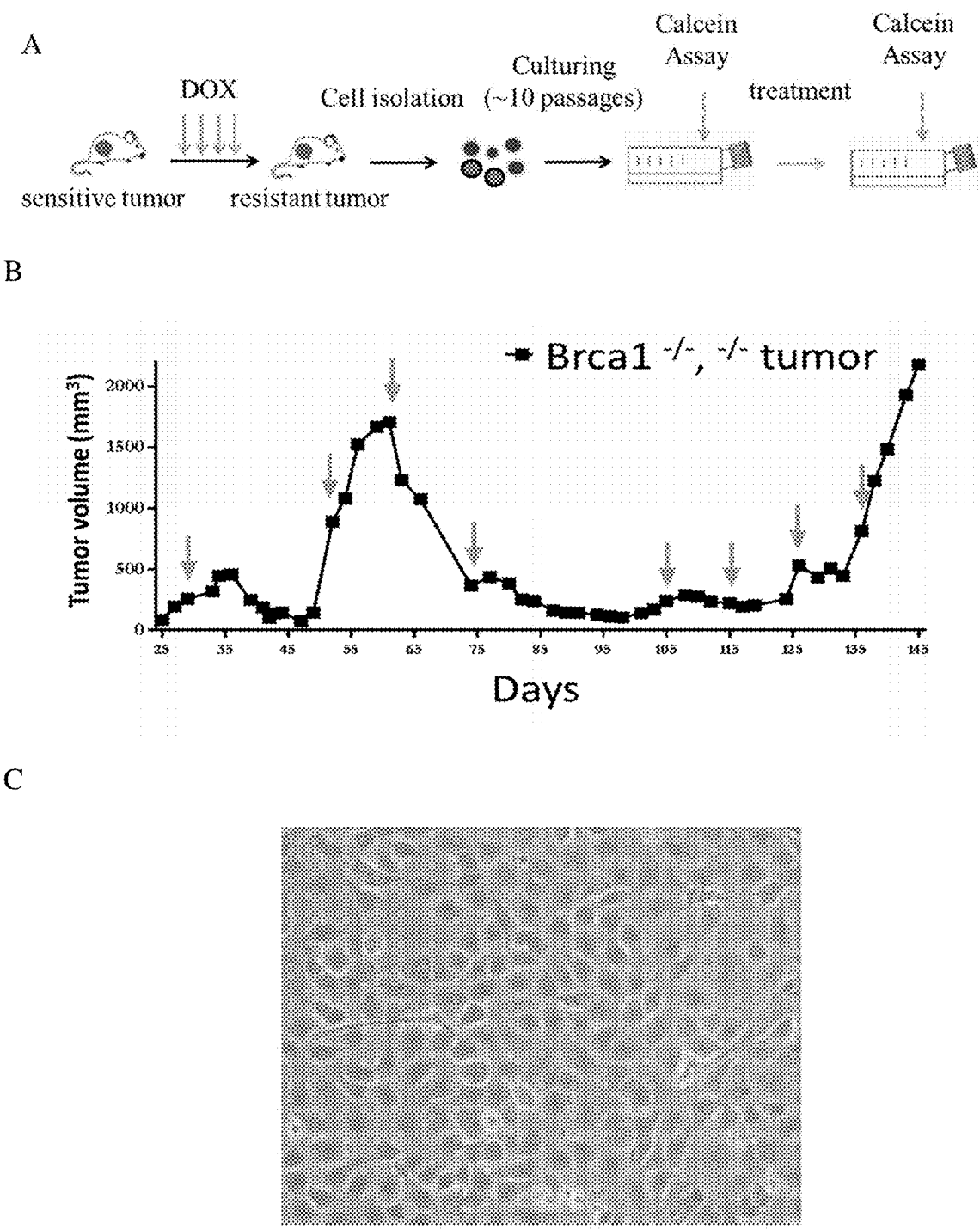
Figure 4 A, 4B and 4C. Effect on P-gp expression (MDR phenotype switch) in a realistic model of drug resistance D
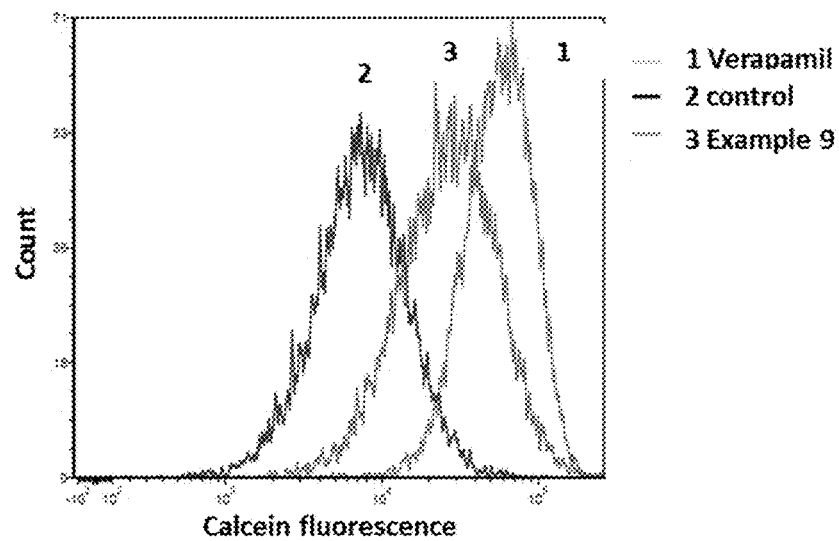
Figure 4D. Effect on P-gp expression (MDR phenotype switch) in a realistic model of drug resistance

MDR-REVERSING 8-HYDROXY-QUINOLINE DERIVATIVES

This is the national stage of International Application PCT/HU2017/050009, filed Apr. 5, 2017.

TECHNICAL FIELD OF THE INVENTION

The present invention relates to 8-hydroxyquinoline derivatives possessing improved selectivity and increased cytotoxicity towards multidrug-resistant cancer cells; the preparation thereof and use of the same in the treatment of cancer, especially multidrug-resistant variants thereof.

BACKGROUND OF THE INVENTION

Anticancer therapies designed to counter cancer-specific pathways have a substantial impact on patient survival in several cancers. However, even among those patients that show initial response to currently available anticancer therapy, drug-resistant clones frequently evolve by a variety of mechanisms. Ultimately, resistance to chemotherapy results in treatment failure, which is the main reason why cancer remains a deadly disease. Multidrug resistant (MDR) cancer cells are able to resist multiple cytotoxic agents with distinct targets. One of the best characterized mechanisms of multidrug resistance is the increased drug efflux mediated by ATP-binding cassette (ABC) transporters, in particular P-glycoprotein (P-gp, MDR1, ABCB1) (Gottesman et al. 2002) (Szakács et al. 2006). ABC proteins, present in all living organisms from prokaryotes to mammals, are transmembrane proteins that control the passage of their substrates across membrane barriers. ABC transporters make up a complex cellular defense system responsible for the recognition and the energy-dependent removal of environmental toxic agents entering the cells or organisms (Sarkadi et al. 2006). In cancer, P-glycoprotein acts as a primary shield that keeps intracellular chemotherapy drug levels below a cell-killing threshold. Cancer cells overexpressing P-glycoprotein become multidrug resistant, as the promiscuity of P-glycoprotein (P-gp) allows the efflux of most clinically used anticancer agents (Türk & Szakács 2009). The contribution of P-gp to poor chemotherapy response was convincingly demonstrated in hematological malignancies, sarcomas, breast cancer, and other solid cancers (Szakacs et al. 2006). Recently, acquired doxorubicin resistance was associated with increased expression of the mouse Mdr1 genes in a genetically engineered mouse model for BRCA1-related breast cancer. Significantly, even moderate increases of Mdr1 expression were found to be sufficient to cause doxorubicin resistance, which could be reversed by the third-generation P-gp inhibitor tariquidar (Pajic et al. 2009). These results confirm that P-gp indeed plays a pivotal role in causing drug resistance in a realistic model of cancer.

Unfortunately, clinical studies conducted with several generations of P-gp inhibitors have failed and the pharmaceutical industry seems to have abandoned the concept of P-gp inhibition (Libby & Hromas 2010).

However, there is still a need for compounds which act as efficient cytostatic and/or chemotherapeutic agents against multidrug-resistant cancer cells with minimal side-effects, as well as for compounds which are suitable for decreasing or eliminating multidrug resistance in cancer cells, thus making them sensitive to existing chemotherapeutic agents.

It was suggested that an alternative strategy to overcome MDR may rely on the concept of collateral sensitivity, first introduced to describe the paradoxical hypersensitivity of drug resistant bacteria against certain compounds (Szybalski & Bryson 1952). According to this concept the objective to treat multidrug resistant cancer could be fulfilled by providing compounds exhibiting selective and preferential cytotoxicity against multidrug-resistant cell lines. Thus, these cell lines, while resistant to one or more drugs, pay the fitness cost of resistance by becoming sensitive to other drugs. Multidrug resistant cells overexpressing resistance-providing transporters exhibit collateral sensitivity against MDR-selective compounds that are selectively toxic to the transporter-expressing cells.

A review of the scientific literature identifies several compounds that were reported to be preferentially toxic against P-gp-expressing cells (Szakács et al. 2014). Most compounds were identified in studies that were undertaken with the intent of characterizing the extent of drug resistance in multidrug-resistant cells.

In several cases (e.g. tiopronin (Goldsborough et al. 2011)), however, the test compounds' MDR-selective activity was found to be restricted to a specific MDR cell line. In such cases, selective toxicity toward P-gp-expressing cells could not be reversed by inhibition of P-glycoprotein, and P-gp-transfected cells and a number of other resistant P-gp-expressing cells were not hypersensitive to the compounds. These data suggested that a molecular alteration in multidrug-resistant cells, not related to P-gp expression, was responsible for the hypersensitivity of cells to such compounds. Thus, in these cases P-gp expression was either not necessary or not sufficient to make the MDR cell hypersensitive against the drugs tested.

Different studies report outstanding MDR-selectivity of desmosdumotin derivatives (Nakagawa-Goto et al., 2010) and Dp44mT (Jansson et al. 2015), which findings, however, were not found to be reproducible in further MDR cell lines expressing P-gp.

In contrast, in the specific case of collateral sensitivity, the toxicity of certain MDR-selective compounds is uniformly increased by the P-gp transporter protein in P-gp-expressing MDR cells e.g. in comparison with control cells not expressing P-gp, whereas this toxicity is abrogated in the presence of P-gp inhibitors (Szakács, Annereau, Lababidi, Shankavaram, Arciello, Kimberly J. Bussey, et al. 2004; Türk et al. 2009). This reveals that in addition to the export of toxic substrates, P-gp can directly sensitize MDR cells against these P-gp-potentiated MDR-selective compounds (Szakács et al. 2004; Ludwig et al. 2006; Türk et al. 2009; Hall et al. 2009). Ludwig et al. describe that cells become hypersensitive to NSC73306 in proportion to their P-gp function, and this selectivity is abrogated by functional inhibition or downregulation of P-gp, thereby supporting the causal link between toxicity and P-gp function (Ludwig et al. 2006).

As it comes from the above analysis, according to this approach MDR-selective compounds applied for treating of MDR cancer can selectively destroy cells expressing the transporter responsible for drug efflux-based multidrug resistance (i.e. P-gp).

Several classes of compounds having MDR-selective activity have been disclosed in the state of the art.

The published International Patent Application WO2006009765 discloses diverse compounds capable for reversing multidrug-resistance in cancer cells. The application relates to a method of inhibiting the growth of neoplastic cells by administering to the subject an antiproliferative agent, wherein the antiproliferative effect of the agent is potentiated by P-gp (i.e. the ABCB1 transporter), including the case when said neoplastic cells have already been exposed to an anti-cancer therapeutical agent which is substrate to P-gp. The application furthermore relates to a method for inhibiting the development of multidrug resistance.

International Patent Applications WO2009102433 and WO2012033601 disclose thiosemicarbazone derivatives having MDR-inverse (i.e. MDR-selective) activity which are effective against multidrug-resistant cells. The selective cytotoxicity ("MDR1 selectivity", see Table 1) has been assessed as a ratio of the "absolute" cytotoxicity of the disclosed compounds measured using the MTT assay in the parental P-gp-negative adenocarcinoma cells to the cytotoxicity determined in an adenocarcinoma cell line expressing high levels of P-gp. The concept of determining the ratio of cytotoxicity of a parental, non multidrug-resistant cell line to the cytotoxicity of a multidrug-resistant cell line is referred to in this specification as determining selective toxicity ratio, selectivity ratio (SR) or briefly, selectivity. Selectivity of the compounds disclosed in WO2009102433 and WO2012033601 are generally lower than approx. 9 and 14, respectively.

International Patent Application WO2012058269 discloses compounds belonging to the class of tiopronins capable of reversing multidrug resistance, exhibiting selectivity up to 51.0. However, tiopronins can not be regarded as MDR-selective compounds in the sense MDR-selectivity is used in the present invention since these do not confirm the criteria thereto described above.

International Patent Application WO2014078898 discloses metal, especially iron and copper complexes of substituted hydrazons, semicarbazones and analogues thereof without disclosing their selectivity.

In the paper of Orina et al. (Orina et al. 2009), correlations were assumed between the expression profile of 48 human ABC transporters and the growth inhibitory profiles of candidate anticancer drugs in the NCI60 cell panel. Orina et al. disclose in the above-mentioned paper that the compound NSC693871 [7-(pyrrolidin-1-ylmethyl)quinolin-8-ol hydrochloride] exhibits selectivity in the order of magnitude of 10 in respect of ABCB1-overexpressing and parental HEK293 cells.

International Patent Application WO2010138686 and Türk et al. (Dóra Türk, Matthew D. Hall, Benjamin F. Chu, Joseph A. Ludwig et al., 2009) discloses compounds suitable for eliciting the reversal of multidrug-resistance. These publications disclose that the 8-hydroxy-quinoline derivatives NSC693871 (see above) and NSC693872 [7-(N,N-diethylaminomethyl)quinolin-8-ol] exhibited selectivity of about 8.48 and 3.90, respectively.

International Patent Application WO2011148208 discloses substituted 8-hydroxyquinolines which are useful for the treatment of diseases associated with neurological and/or oxidative stress. This reference indicates the cytotoxic effect of some compounds in cancer cell lines but is silent with respect to their selectivity and potency.

A further patent search revealed several documents which disclose compounds falling within the scope of the general formula (I) of the claims discussed below. However, some of these documents do not mention any pharmacological effect (i.e. they concentrate on the synthesis way) while the remaining documents declare a very different pharmaceutical utility for the disclosed compounds. Here we list these documents and give in brackets the relevant parts thereof, mentioning the effect, too, if any.

*J. Med. Chem.*, 56(2), 521-533 (2013) (Compound 13; having Catheprim B inhibitory activity);
*Acta Pharmaceutica Jugoslavica*, 33(3-4), 199-208 (1983) (Compounds 5, 7 and 11, having antibacterial activity);
FR 2160718 A1 (Roussel) (1973 Jul. 6) (Example 1, having antibacterial activity);
*ChemMedChem*, 11(12), 1284-1295 (2016 Feb. 16) (Compounds 6a and 6b, having anti-Alzheimer activity);
WO 2010/042163 A2 (Johns Hopkins Univ.) (2010 Apr. 15) (Compound 2b), having angiogenesis inhibitory activity);
WO 96/09291 A1 (Henkel) (1996 Mar. 28) (Example 1—no activity is disclosed);
U.S. Pat. No. 2,681,910 (Burckhalter) (1954 Jun. 22) (Example 10—no activity is disclosed);
*Trudove na Nauchnoizsledovatelskiya Khimikofarmatsevtichen Institut*, 15, 71-80 (1985) & Caplus abstract (AN:1986:552901)—no activity is disclosed
*J. Virology*, 84(7), 3408-3412 (2010) (FIG. 3, having anti-prion activity);
*Heterocycles*, 68(3), 531-537 (2006) (Compound 3—no activity is disclosed);
*Biomedical Chromatography*, 28(1), 142-151 (2014) (Compound 12 to 15—no activity is disclosed);
*J. Org. Chem.*, 26, 4078-4083 (1961) (Compounds (I) and (IV)—no activity is disclosed).

These compounds are excluded from the scope of claims by disclaimers. Here we maintain our right to draw further disclaimers, if it is necessary for the complete delimitation.

The object of the present inventors was to provide a solution for inhibition of the proliferation or killing of multidrug-resistant cells. Surprisingly it has been found that a group of 8-hydroxyquinoline derivatives are useful for this purpose. The above objectives thus have been solved according to the present invention.

SUMMARY OF THE INVENTION

We have unexpectedly found that certain 8-hydroxyquinoline derivatives exhibit cytotoxicity for P-gp-expressing multidrug-resistant cancer cells, allowing effectively inhibiting the growth of such cancer cells. Furthermore, we have surprisingly found that 8-hydroxyquinoline derivatives according to the present invention are capable of selectively eliminating P-gp-expressing multidrug-resistant cell lines.

In addition to the above, we have unexpectedly found that treatment, preferably already a single dose treatment, more preferably a single, high dose treatment of the P-gp-expressing multidrug-resistant cells with the new MDR-selective 8-hydroxyquinoline derivatives according to the present invention resulted in the loss of P-gp expression and re-sensitization to chemotherapy. In human MDR cell lines, this rapid phenotype-switch resulted in an at least 50%, at least 60%, at least 70%, at least 80% or at least 90% ratio of non-P-gp-expressing cells in the cell population survived said treatment, preferably a single dose treatment, more preferably a single, high dose treatment. Moreover, MDR-selective 8-hydroxy-quinoline derivatives also essentially eradicated P-glycoprotein expression in a primary breast tumor culture obtained from doxorubicin resistant spontaneous mouse mammary carcinoma.

Thus, the compounds according to the present invention are useful for the treatment of hyperproliferative diseases, especially multidrug-resistant cancer and metastatic cancer when administered individually or in combination with a further chemotherapeutical agent. Forms of hyperproliferative diseases which can be treated according to the invention include solid tumors, such as sarcomas and carcinomas. Additional types of multidrug resistant hyperproliferative diseases, wherein the compounds according to the present invention can be used, are e.g. multidrug resistant prostate, breast, colon, bladder, cervical, skin, testicular, kidney, ovarian, stomach, brain, liver, pancreatic or esophageal cancer, lymphoma, hematological tumors including leukemias, polycythemia vera, Hodgkin's disease, non-Hodgkin's lymphoma, multiple myeloma and myelodysplasia.

Compounds according to the present invention can be used alone or in combination with cytostatic or chemotherapeutical agents, wherein at least one compound according to the present invention is administered simultaneously, consecutively or prior to cytostatic or chemotherapeutical treatment. Agents used in connection with the compounds of the present invention can be selected from e.g. chemotherapeutical agents, such as alkylating agents, alkylating-like agents, antimetabolites, anti-microtubule agents, topoisomerase inhibitors or anticancer antibodies.

The compounds of the invention can also be used for the prevention of the diseases listed above or herein. The compounds of the invention can also be used for preventing the development of the MDR phenotype in cells, e.g. cancerous cells of a patient.

The present invention relates to the following subjects:

1. Compound, which is a 8-hydroxy-quinoline derivative of general Formula I,

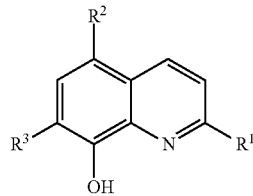

Formula I wherein
$R^1$ represents
a) hydrogen;
b) $C_1$-$C_6$-alkyl;
c) heterocyclyl1, which group is a heterocyclyl group derived from a saturated, partially unsaturated or aromatic ring system with 3 to 5 carbon atoms and 1 to 2 heteroatom(s) selected from the group of N, O and S;
d) —NH—N=$R^a$ wherein =$R^a$ is a $C_1$-$C_6$-alkylidenyl group substituted with aryl or heterocyclyl1 group, in which the aryl or heterocyclyl1 is optionally substituted with 1 to 3 substituent(s) selected from the group of hydroxyl and $C_1$-$C_6$-alkoxy groups; or
e) —CH=N—NH—$R^e$, wherein $R^e$ is aryl or heteroaryl1, where heteroaryl1 is a heteroaryl group derived from a monocyclic or bicyclic aromatic ring system with 1 to 3 heteroatom(s) selected from the group of N, O and S and the other ring forming atoms are carbon atoms, where the aryl and heteroaryl1 is optionally substituted with 1 to 3 substituent(s) selected from the group of hydroxyl and $C_1$-$C_6$-alkoxy groups;
$R^2$ is hydrogen, halogen, nitro, ($C_1$-$C_6$-alkyl)sulfonyloxy, phenylsulfonyloxy or toluenesulfonyloxy or ((2-(3-methyl-3H-diazirin-3-yl)ethyl)(prop-2-yn-1-yl)amino)methyl;
$R^3$ is —CHR$^f$—NHR$^g$, wherein
$R^f$ is H or $C_1$-$C_6$ alkoxycarbonyl, and
$R^g$ is $C_{3-8}$ cycloalkyl or —(CH$_2$)$_n$-aryl, wherein n is an integer from 1 to 3 and aryl is optionally substituted with 1 to 3 substituent(s) selected from the group of halogen atoms and $C_1$-$C_6$-alkoxy groups;
or $R^f$ and $R^g$ form, together with the adjacent atoms, a heteroaryl2 group which is a heteroaryl derived from a partially saturated bicyclic or tricyclic ring system with 1 to 3 heteroatom(s) selected from the group of N, O and S and the other ring forming atoms are carbon atoms, which group is optionally substituted with 1 to 3 $C_1$-$C_6$-alkoxy group(s);
or $R^f$ and $R^g$ form, together with the adjacent atoms, a saturated bicyclic ring system containing 2 N atoms as heteroatoms and the other ring forming atoms are carbon atoms, which group is optionally substituted with an oxo group;
or $R^3$ is ((2-(3-methyl-3H-diazirin-3-yl)ethyl)(prop-2-yn-1-yl)amino)methyl;
or $R^3$ is —(CH$_2$)$_n$-heterocyclyl2, wherein n is an integer from 1 to 3 and heterocyclyl2 is a 5- to 6-membered saturated ring system with 3 to 5 carbon atoms and 1 to 2 nitrogen heteroatom(s);
with the proviso that when $R^1$ and $R^2$ are hydrogen, $R^3$ is different from 1-pyrrolidinyl-methyl,
and stereoisomers, pharmaceutically acceptable salts, solvates and metal complexes thereof,
for use in anti-cancer chemotherapy, wherein the compound has P-gp-potentiated MDR selectivity whereby it is capable of killing P-gp-expressing multidrug-resistant cells and wherein the compound is capable of reducing expression of P-gp in a population of P-gp-expressing cells.

2. The compound for use according to point 1, wherein said compound reduces expression of P-gp in P-gp-expressing multidrug-resistant cells so that preferably the ratio of non-P-gp-expressing cells is at least 20%, 30%, 40%, 50%, 60%, or 70% after the first 10, preferably 5, 4, 3 or 2 doses or highly preferably after the first dose treatment by said compound.

3. The compound for use according to point 1 or 2, where the compound is applied in the use individually or in combination with a second therapeutical agent in the treatment of cancer, in particular multidrug-resistant and/or metastatic cancer, wherein the second therapeutical agent, if present, is preferably a chemotherapeutical agent or an anti-cancer antibody.

4. The compound for use according to point 3 where the compound is applied in the use in combination with a second therapeutical agent, preferably with a chemotherapeutical agent in the treatment of cancer, in particular multidrug-resistant cancer, wherein the second therapeutical agent is administered simultaneously with or subsequently to said compound.

5. The compound for use according to point 3 or 4 where the compound is applied in the use in combination with a second therapeutical agent which is a chemotherapeutical agent in the treatment of cancer, wherein the second therapeutical agent is preferably a chemotherapeutical agent selected from alkylating agents, alkylating-like agents, alkylating-like agents, antimetabolites, anti-microtubule agents, topoisomerase inhibitors and cytotoxic antibiotics.

6. The compound for use according to any of points 1 to 5 where the use comprises a therapeutic regimen wherein
a) a P-gp-potentiated MDR selective compound of any of points 1 to 4 is administered for a given period of time thereby killing P-gp-expressing cells and arriving at a non-P-gp-expressing phenotype in surviving tumor cells,
b) a cytotoxic chemotherapeutic compound, preferably by a chemotherapeutic compound transportable by P-gp, is administered thereby killing the surviving tumor cells of non-P-gp-expressing phenotype and
c) optionally in a further stage of the treatment one or both of a further P-gp-potentiated MDR selective compound of any of points 1 to 4 and a further cytotoxic chemotherapeutic compound is/are administered as defined in steps a) and b).

Here we mention that the preferred embodiments for the compounds for use according to the above points 1 to 6 are the same as given points 8 to 10 below, but without the proviso parts applied in points 8 to 10 (i.e. without any limitation).

7. Compound, which is a 8-hydroxy-quinoline derivative of general Formula I,

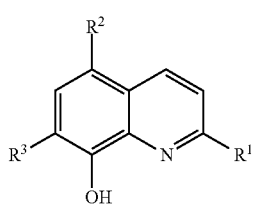

Formula I wherein
$R^1$ represents
a) hydrogen;
b) $C_1$-$C_6$-alkyl;
c) heterocyclyl1, which group is a heterocyclyl group derived from a saturated, partially unsaturated or aromatic ring system with 3 to 5 carbon atoms and 1 to 2 heteroatom(s) selected from the group of N, O and S;
d) —NH—N=$R^a$ wherein =$R^a$ is a $C_1$-$C_6$-alkylidenyl group substituted with aryl or heterocyclyl1 group, in which the aryl or heterocyclyl1 is optionally substituted with 1 to 3 substituent(s) selected from the group of hydroxyl and $C_1$-$C_6$-alkoxy groups; or
e) —CH=N—NH—$R^e$, wherein $R^e$ is aryl or heteroaryl1, where heteroaryl1 is a heteroaryl group derived from a monocyclic or bicyclic aromatic ring system with 1 to 3 heteroatom(s) selected from the group of N, O and S and the other ring forming atoms are carbon atoms, where the aryl and heteroaryl1 is optionally substituted with 1 to 3 substituent(s) selected from the group of hydroxyl and $C_1$-$C_6$-alkoxy groups;

$R^2$ is hydrogen, halogen, nitro, ($C_1$-$C_6$-alkyl)sulfonyloxy, phenylsulfonyloxy or toluenesulfonyloxy or ((2-(3-methyl-3H-diazirin-3-yl)ethyl)(prop-2-yn-1-yl)amino)methyl);

$R^3$ is —CHR$^f$—NHR$^g$, wherein
$R^f$ is H or $C_1$-$C_6$ alkoxycarbonyl, and
$R^g$ is $C_{3-8}$ cycloalkyl or —(CH$_2$)$_n$-aryl, wherein n is an integer from 1 to 3 and aryl is optionally substituted with 1 to 3 substituent(s) selected from the group of halogen atoms and $C_1$-$C_6$-alkoxy groups;
or $R^f$ and $R^g$ form, together with the adjacent atoms, a heteroaryl2 group which is a heteroaryl derived from a partially saturated bicyclic or tricyclic ring system with 1 to 3 heteroatom(s) selected from the group of N, O and S and the other ring forming atoms are carbon atoms, which group is optionally substituted with 1 to 3 $C_1$-$C_6$-alkoxy group(s);
or $R^f$ and $R^g$ form, together with the adjacent atoms, a saturated bicyclic ring system containing 2 N atoms as heteroatoms and the other ring forming atoms are carbon atoms, which group is optionally substituted with an oxo group;
or $R^3$ is ((2-(3-methyl-3H-diazirin-3-yl)ethyl)(prop-2-yn-1-yl)amino)methyl;

or $R^3$ is —(CH$_2$)$_n$-heterocyclyl2, wherein n is an integer from 1 to 3 and heterocyclyl2 is a 5- to 6-membered saturated ring system with 3 to 5 carbon atoms and 1 to 2 nitrogen heteroatom(s);
with the proviso that
when $R^1$ and $R^2$ are hydrogen, $R^3$ is different from (pyrrolidin-1-yl)-methyl, (piperazin-1-yl)-methyl, (imidazolidin-1-yl)methyl, 1,2,3,4-tetrahydro-isoguionoline-1-yl, 6,7-dimethoxy-1,2,3,4-tetrahydro-isoguionoline-1-yl, (piperidine-1-yl)-methyl;
when $R^1$ is hydrogen, $R^2$ is bromine, $R^3$ is different from (piperidine-1-yl)-methyl, (pyrrolidin-1-yl)-methyl;
when $R^1$ is hydrogen, $R^2$ is chlorine, $R^3$ is different from benzylamino-methyl, (piperazin-1-yl)-methyl, (piperidine-1-yl)-methyl, (pyrrolidin-1-yl)-methyl;
when $R^1$ is hydrogen, $R^2$ is nitro, $R^3$ is different from benzylamino-methyl, (piperidine-1-yl)-methyl, (pyrrolidine-1-yl)-methyl, phenylethyl-amino-methyl, (piperazine-1-yl)-methyl;
when $R^1$ is methyl, $R^2$ is hydrogen, $R^3$ is different from (piperidine-1-yl)-methyl, 1,2,3,4-tetrahydro-isoguionoline-1-yl, 6,7-dimethoxy-1,2,3,4-tetrahydro-isoguionoline-1-yl;
and stereoisomers, pharmaceutically acceptable salts, solvates and metal complexes thereof.

8. Compound of general Formula I according to point 7, wherein
$R^1$ is selected from the group of hydrogen; methyl; pyridine-2-yl; imidazole-2-yl; 1-aryl-($C_1$-$C_2$-alkylidene)-hydrazin-1-yl, wherein the aryl group may be substituted by hydroxyl; 1-piridin-2-yl-($C_1$-$C_2$-alkylidene)-hydrazin-1-yl; thiosemicarbamoyl-1-phenyl wherein the phenyl groups can have a methoxy substituent; 2-(1,3-benzothiazol-2-yl)hydrazin-1-ylidene]methyl]; and [2-(8-hydroxyquinolin-2-yl)hydrazin-1-ylidene]methyl];
$R^2$ is selected from the group of hydrogen, halogen; nitro, ($C_1$-$C_6$)alkylsulfonyl and (((2-(3-methyl-3H-diazirin-3-yl)ethyl)(prop-2-yn-1-yl)amino)methyl);
$R^3$ is selected from the group of [($C_3$-$C_8$-cycloalk)-1-yl]-amino-methyl; a benzylamino-methyl wherein the aryl group of the benzyl and the methyl group may be substituted by one to three $C_1$-$C_6$-alkoxy, $C_1$-$C_6$-alkyl or halogens; 1,2,3,4-tetrahydroisoquinolin-1-yl optionally substituted by one to three $C_1$-$C_6$-alkoxy groups, 4,5,6,7-tetrahydrothieno[3,2-c]pyridine-4-yl, 1H,2H, 3H,4H, 9H-pyrido-[3,4-b]indol-1-yl, octahydroquinoxal-2(1H)-one-3-in-yl, piperidin-1-yl-methyl group and (((2-(3-methyl-3H-diazirin-3-yl)ethyl)(prop-2-yn-1-yl)amino)methyl) group;
with the proviso that
when $R^1$ and $R^2$ are hydrogen, $R^3$ is different from (piperidine-1-yl)-methyl, 1,2,3,4-tetrahydro-isoquionoline-1-yl, 6,7-dimethoxy-1,2,3,4-tetrahydro-isoquinoline-1-yl;
when $R^1$ is hydrogen, $R^2$ is bromine, $R^3$ is different from (piperidine-1-yl)-methyl;
when $R^1$ is hydrogen, $R^2$ is chlorine, $R^3$ is different from benzylamino-methyl, (piperidine-1-yl)-methyl;
when $R^1$ is hydrogen, $R^2$ is nitro, $R^3$ is different from benzylamino-methyl, (piperidine-1-yl)-methyl;
when $R^1$ is methyl, $R^2$ is hydrogen, $R^3$ is different from (piperidine-1-yl)-methyl, 1,2,3,4-tetrahydro-isoquionoline-1-yl, 6,7-dimethoxy-1,2,3,4-tetrahydro-isoquionoline-1-yl;
and stereoisomers, pharmaceutically acceptable salts, solvates and metal complexes thereof.

9. Compound of general Formula I according to point 7 or 8, wherein $R^1$ is selected from the group of hydrogen, methyl, 1-(2-hydroxyphenyl)-ethylidene]-hydrazin-1-yl, 1-(pyridin-2-yl)-ethylidene]-hydrazin-1-yl, 2-[(E/Z)-2-[1-(pyridin-2-yl)-ethylidene]hydrazin-1-yl, (Z)-2-[(pyridin-2-yl)-methylidene]-hydrazin-1-yl, (benzothiazol-2-yl)-hydrazin-1-ylidene)-methyl, 2-(8-hydroxyquinolin-2-yl)-hydrazin-1-ylidene)methyl, thiosemicarbamoyl-1-(4-methoxyphenyl) and pyridine-2-yl, imidazole-2-yl;

$R^2$ is selected from the group of hydrogen, nitro, $(C_1-C_6)$ alkylsulfonyl, pyridinyl, imidazolyl and halogen, $R^3$ is selected from the group of hydrogen, (piperidin-1-yl)methyl, cyclohexylamino-methyl, (4-methoxybenzyl)-amino-methyl, (2-methoxybenzyl)-amino-methyl, (2,4-dimethoxybenzyl)-amino-methyl, 3,4-dimethoxybenzyl-amino-methyl, fluorobenzyl)-amino-methyl, ethyl-2-{[(2-fluorophenyl)methyl]amino}acetate, {1H,2H,3H,4H,9H-pyrido[3,4-b]indol-1-yl}, {4H,5H,6H,7H-tetrahydrothieno[3,2-c]pyridin-4-yl}, 1,2,3,4-tetrahydroisoquinolin-1-yl, 6,7-dimethoxy-1,2,3,4-tetrahydroisoquinolin-1-yl, (pyridin-3-yl)[(1,3-thiazol-2-yl)amino]methyl and benzyl-amino-methyl;

with the proviso that when $R^1$ and $R^2$ are hydrogen, $R^3$ is different from (piperidine-1-yl)-methyl, 1,2,3,4-tetrahydro-isoquionoline-1-yl, 6,7-dimethoxy-1,2,3,4-tetrahydro-isoquionoline-1-yl;

when $R^1$ is hydrogen, $R^2$ is bromine, $R^3$ is different from (piperidine-1-yl)-methyl;

when $R^1$ is hydrogen, $R^2$ is chlorine, $R^3$ is different from benzylamino-methyl, (piperidine-1-yl)-methyl;

when $R^1$ is hydrogen, $R^2$ is nitro, $R^3$ is different from benzylamino-methyl, (piperidine-1-yl)-methyl;

when $R^1$ is methyl, $R^2$ is hydrogen, $R^3$ is different from (piperidine-1-yl)-methyl, 1,2,3,4-tetrahydro-isoquionoline-1-yl, 6,7-dimethoxy-1,2,3,4-tetrahydro-isoquionoline-1-yl;

and stereoisomers, pharmaceutically acceptable salts, solvates and metal complexes thereof.

10. A compound of general Formula I according to point 7 selected from the group of:
7-(((2,4-dimethoxybenzyl)amino)methyl)-5-(methylsulfonyl)quinolin-8-ol;
7-(((3,4-dimethoxybenzyl)amino)methyl)-5-nitroquinolin-8-ol;
7-(((2-methoxybenzyl)amino)methyl)-5-nitroquinolin-8-ol;
7-(((2,4-dimethoxybenzyl)amino)methyl)-5-nitroquinolin-8-ol;
7-(((4-methoxybenzyl)amino)methyl)-5-nitroquinolin-8-ol;
(3R,4aS,8aS)-3-(5-chloro-8-hydroxyquinolin-7-yl)octahydroquinoxalin-2(1H)-one;
(3S,4aS,8aS)-3-(5-chloro-8-hydroxyquinolin-7-yl)octahydroquinoxalin-2(1H)-one;
5-bromo-7-(((3,4-dimethoxybenzyl)amino)methyl)quinolin-8-ol;
5-chloro-7-(((2,4-dimethoxybenzyl)amino)methyl)quinolin-8-ol;
(E/Z)-7-(piperidin-1ylmethyl)-2-(1-(pyridin-2-yl)ethylidene)hydrazinyl)quinolin-8-ol;
(E/Z)-2-(2-(1-(2-hydroxyphenyl)ethylidene)hydrazinyl)-7-(piperidin-1-ylmethyl)quinolin-8-ol;
(E/Z)-7-(piperidin-1-ylmethyl)-2-(2-(pyridine-2-ylmethylene)hydrazinyl)quinolin-8-ol; 5-chloro-7-((cyclohexylamino)methyl)quinolin-8-ol;
5-chloro-7-(((4-methoxybenzyl)amino)methyl)quinolin-8-ol;
5-bromo-7-(((2-methoxybenzyl)amino)methyl)quinolin-8-ol;
5-bromo-7-(((2,4-dimethoxybenzyl)amino)methyl)quinolin-8-ol;
5-bromo-7-(((4-methoxybenzyl)amino)methyl)quinolin-8-ol;
5-chloro-7-({[(2-fluorophenyl)methyl]amino}methyl)quinolin-8-ol;
5-chloro-7-(1,2,3,4-tetrahydroisoquinolin-1-yl)quinolin-8-ol;
5-bromo-7-(1,2,3,4-tetrahydroisoquinolin-1-yl)quinolin-8-ol;
5-nitro-7-(1,2,3,4-tetrahydroisoquinolin-1-yl)quinolin-8-ol;
5-chloro-7-(6,7-dimethoxy-1,2,3,4-tetrahydroisoquinolin-1-yl)quinolin-8-ol;
5-chloro-7-(4,5,6,7-tetrahydrothieno[3,2-c]pyridin-4-yl)quinolin-8-ol;
7-(4,5,6,7-tetrahydrothieno[3,2-c]pyridin-4-yl)quinolin-8-ol;
5-nitro-7-(4,5,6,7-tetrahydrothieno[3,2-c]pyridin-4-yl)quinolin-8-o and
2-(2-methyl-7-{4,5,6,7-tetrahydrothieno[3,2-c]pyridin-4-yl}quinolin-8-ol and stereoisomers, pharmaceutically acceptable salts, solvates and metal complexes thereof.

11. Pharmaceutical formulations containing a compound of the general Formula I according to any of points 7 to 10 in admixture with pharmaceutically acceptable excipients.

12. A compound of the general Formula I according to any of points 7 to 10 for use in therapy.

13. Compounds of the general Formula I according to any of points 7 to 10 for use individually or in combination with a second therapeutical agent, preferably with a chemotherapeutical agent in the treatment of a hyperproliferative disease, in particular multidrug-resistant or metastatic cancer, selected from sarcomas and carcinomas including fibrosarcoma, myxosarcoma, liposarcoma, chondrosarcoma, osteogenic sarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, tumors of the CNS system including glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma, prostate, breast, colon, bladder, cervical, skin, testicular, kidney, ovarian, stomach, brain, liver, pancreatic or esophageal cancer, lymphoma, leukemia including acute lymphocytic leukemia, acute myelocytic leukemia, acute myelogenous leukemia and myeloblasts, promyelocytic, myelomonocytic, monocytic and erythroleukemia, chronic myelocytic (granulocytic) leukemia, chronic myelogenous leukemia, chronic lymphocytic leukemia), polycythemia vera, lymphoma, Hodgkin's disease, non-Hodgkin's lymphoma, multiple myeloma, Waldenstrom's macro globulinemia, heavy chain disease, myelodysplastic syndrome, hairy cell leukemia and myelodysplasia.

14. Compounds of the general Formula I according to any of points 7 to 10 for use in combination with a second therapeutical agent, preferably with a chemotherapeutical agent for the treatment of cancer, in particular multidrug-resistant and/or metastatic cancer, wherein the multidrug-resistance is predominantly originating from the overexpression of P-gp.

15. Method for the treatment of a hyperproliferative disease, especially multidrug-resistant or metastatic cancer, selected from sarcomas and carcinomas including fibrosarcoma, myxosarcoma, liposarcoma, chondrosarcoma, osteogenic sarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, tumors of the CNS system including glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma, prostate, breast, colon, bladder, cervical, skin, testicular, kidney, ovarian, stomach, brain, liver, pancreatic or esophageal cancer, lymphoma, leukemia including acute lymphocytic leukemia, acute myelocytic leukemia, acute myelogenous leukemia and myeloblasts, promyelocytic, myelomonocytic, monocytic and erythroleukemia, chronic myelocytic (granulocytic) leukemia, chronic myelogenous leukemia, chronic lymphocytic leukemia), polycythemia vera, lymphoma, Hodgkin's disease, non-Hodgkin's lymphoma, multiple myeloma, Waldenstrom's macro globulinemia, heavy chain disease, myelodysplastic syndrome, hairy cell leukemia and myelodysplasia, which comprises administering a compound of the general Formula I according to any of points 7 to 10 alone or in combination with a further therapeutical agent including chemotherapeutical agents to a patient in need of such treatment.

SHORT DESCRIPTION OF THE FIGURES

FIG. 1: Fraction of P-gp-positive and -negative cells in the population after treatment with a single dose of the state of the art and two example compounds of the invention FIG. 2: P-glycoprotein "switch" assay FIG. 3: Renewed sensitivity of MDR cells to doxorubicin following a single treatment with the example compounds of the present invention.

FIG. 4: Effect on P-gp expression in a realistic model of drug resistance (MDR phenotype switch).

A. Schematic overview of the experimental strategy. Primary cells were derived from brca1-/-/;p53-/- spontaneous mammary tumors transplanted orthotopically into syngeneic wild-type female mice.

B. Representative curve (tumor volume over time) showing response to repeated treatments of mammary tumor-bearing mice with the maximum tolerable dose of doxorubicin (arrows).

C. Microscopic image of a primary tumor cell culture isolated from a resistant tumor.

D. Functional expression of P-gp as determined by the Calcein assay in primary tumor cells obtained from resistant tumors before (2) and after treatment with a single dose of the compound of Example 9 (3). Verapamil control (corresponding to complete P-gp inhibition) is also given (1).

DETAILED DESCRIPTION OF THE INVENTION

Definitions

In the present application, the term "P-gp-potentiated MDR-selective" is used herein for compounds whose toxicity is directly increased by P-gp. Such compounds exhibit selective toxicity to MDR cells in many cell types, however, MDR-cell selectivity is abrogated in the presence of P-gp inhibitors and long/short term treatment results in the loss of P-gp.

The term "tumor" is used to describe an abnormally increased mass of tissue or population of cells.

"Cancer", as used herein is a malignant tumor, and relates to a group of diseases involving abnormal cell growth with the potential to invade or spread to other parts of the body.

A "chemotherapeutic agent" is a substance, preferably compound or molecule useful in chemotherapy i.e. in cancer treatment that uses chemical substances, administered according to a given chemotherapy regimen and given with a curative intent, or to prolong life or to reduce symptoms (palliative chemotherapy) or to prevent onset of or exacerbation of cancer.

A "chemotherapeutic agent" may be a "cytotoxic" agent having the meaning an agent acting by killing cells that divide rapidly.

Some of the compounds according to the present invention can exist as individual stereoisomers or as a mixture of stereoisomers, e.g. as racemates, mixtures of enantiomers or pure chiral compounds etc. All such stereoisomers belong to the scope of the present invention.

As used herein, the term "halogen" means fluorine, chlorine, bromine or iodine, preferably fluorine, chlorine, bromine, even more preferably bromine or chlorine.

As used herein, the term "alkyl" alone or in combinations means a straight or branched-chain alkyl group containing from 1 to 6, preferably 1 to 5 carbon atom(s) (i.e. "$C_{1-6}$" or "$C_{1-5}$" alkyl groups), such as methyl, ethyl, propyl, isopropyl, butyl, sec-butyl, t-butyl and pentyl. In special cases this phrase can relate to alkyl groups containing from 1 to 4, or 1 to 3 or 1 to 2 carbon atom(s) (i.e. "$C_{1-4}$" or "$C_{1-3}$" or "$C_{1-2}$" alkyl groups), where the methyl is a preferred embodiment.

As used herein, the term "cylolalkyl" means a group that is derived from a $C_{3-8}$, preferably $C_{3-6}$ cycloalkane by removal of a hydrogen atom from the ring, for example cyclopropyl, cyclobutyl, cyclopentyl, cyclohexyl, wherein the cyclohexyl and cyclopentyl are preferred embodiments, especially the cyclohexyl.

When there is in formula (I) a group of —CHR$^f$—NHR$^g$ [see in the meaning of R$^3$], then R$^f$ is preferably H, especially when R$^g$ is cycloalkyl or —(CH$_2$)n-aryl.

As used herein, the term "alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

As used herein, the term "$C_{1-6}$ alkoxycarbonyl" means an alkyl-O—C(O)— group in which the alkyl group is as previously described $C_{1-5}$ alkyl group, preferably $C_{1-4}$ or $C_{1-3}$ alkyl group, most preferably ethyl group. The bond to the parent moiety is through the carbon atom of the carboxyl [C(O)] moiety.

As used herein the term "aryl", alone or in combinations means an aromatic monocyclic or polycyclic ring system comprising 6 to 14 carbon atoms, preferably 6 to 10 carbon atoms. Non-limiting examples of suitable aryl groups include phenyl, and naphthyl, where phenyl is a preferred embodiment.

The term "heterocyclyl1" means a heterocyclyl group derived from a (condensed) saturated, partially unsaturated or aromatic ring system with 3 to 5 carbon atoms and 1 to 2 heteroatom(s) selected from the group of N, O and S [i.e. group of N (nitrogen), O (oxygen) or S (sulfur) atoms], for example furanyl, pyrrolyl, thienyl, pyridil (pyridinyl), pyranyl, oxazinyl, imidazolyl, pyrazolyl, oxazolyl, thiazolyl, pyrrolidinyl, piperidinyl, imidazolidinyl (and the di- and tetrahydro derivatives of the aromatic type groups). Preferred are saturated, partially unsaturated or aromatic 5- to 6-membered ring systems with 3 to 4 carbon atoms and 1 to 2 nitrogen heteroatom(s) for example pyrrolyl, dihydropyrrolyl, pyrrolidinyl, pyridyl (pyridinyl), dihydropyridyl, piperidinyl, imidazolyl (+di- and tetrahydro derivatives thereof) imidazolidinyl pyrazolyl(+di- and tetrahydro derivatives thereof), where the aromatic 5- to 6-membered ring systems with 3 to 4 carbon atoms and 1 to 2 nitrogen heteroatom(s) are even more preferred, where pyridyl (pyridinyl) and imidazolyl are the most preferred embodiments, When the "heterocyclyl1" is the substituent of $=R^a$, then it can be preferably aromatic 6-membered ring systems with 4 to 5 carbon atoms and 1 to 2 nitrogen heteroatom(s), most preferably pyridyl (pyridinyl), The term "heterocyclyl2" means a group derived from a 5- to 6-membered (condensed) saturated ring system with 3 to 5 carbon atoms and 1 to 2 nitrogen atoms, preferable piperidinyl.

The term alkylidenyl means a divalent group derived from an alkane by removal of two hydrogen atoms from the same carbon atom and the free valencies being part of a double bond, preferably $C_{1-6}$-alkylidenyl group, even more preferably $C_{1-4}$-alkylidenyl group, e.g. methylidenyl (methylenyl) or ethylidenyl, most preferably ethylidenyl. If it is substituted, preferably it takes place on the C-1 atom (which carries the double bond).

When the "heterocyclyl1" is the substituent of $=R^a$, then it can be preferably aromatic 6-membered ring systems with 4 to 5 carbon atoms and 1 to 2 nitrogen heteroatom(s), most preferably pyridyl (pyridinyl), The term "heteroaryl1" means a group derived from a monocyclic or bicyclic aromatic ring system (condensed double ring systems) with 1 to 3 heteroatom(s) selected from the group of N, O and S [i.e. group of N (nitrogen), O (oxygen) or S (sulfur) atoms], where the other ring forming atoms are carbon atoms. In a preferred embodiment the "heteroaryl1" means a group derived from a bicyclic aromatic ring system with 1 to 2 heteroatom(s) selected from the group of N, O and S [where N and 5 is preferred) and the other ring forming atoms are carbon atoms, where the most preferred embodiments are 1,3-benzothiazol and quinoline, optionally substituted with hydroxyl (OH), see e.g. 8-hydroxyquinoline.

The term "heteroaryl2" means a heteroaryl group derived from a partially saturated bicyclic or tricyclic ring system (condensed double and triple ring systems) with 1 to 3 heteroatom(s) selected from the group of N, O and S [i.e. group of N (nitrogen), O (oxygen) or S (sulfur) atoms] and the other ring forming atoms are carbon atoms. In a preferred embodiment the "heteroaryl2" means a group derived from a bi- or tricyclic partially saturated and partially aromatic ring system with 1 to 2 heteroatom(s) selected from the group of N, O and S [where N and S is preferred] where the other ring forming atoms are carbon atoms. Examples for such groups are as follows: 1,2,3,4-tetrahydroisoquinolinyl (preferably 1,2,3,4-tetrahydroisoquinolin-1-yl), 4,5,6,7-tetrahydrothieno[3,2-c]pyridinyl (preferably 4,5,6,7-tetrahydrothieno[3,2-c]pyridin-4-yl), and 1H,2H,3H,4H,9H-pyrido[3,4-b]indolyl (1H,2H,3H,4H,9H-pyrido[3,4-b]indol-1-yl).

When $R^f$ and $R^g$ form, together with the adjacent atoms, a (condensed) saturated bicyclic ring system containing 2 N atoms as heteroatoms where the other ring forming atoms are carbon atoms, which group is optionally substituted with an oxo group, a preferred embodiment is the group deriving from octahydroquinoxalin-2(1H)-one (octahydroquinoxalin-2(1H)-one-yl).

The expressions such as "pyrimidinyl", "imidazolyl" etc. embrace all possible stereoisomers, e.g. 2-pyrimidinyl, 3-pyrimidinyl, 4-pyrimidinyl.

The term "salt" means any ionic compound formed between one of the embodiments of the present invention and an acidic or basic molecule that can donate or accept ionic particles to/from its corresponding base/acid. The quaternary amine salts are also included.

Pharmaceutically acceptable (i.e., non-toxic, physiologically acceptable) salts are preferred, although other salts are also useful. Salts of the compounds of the formula (I) may be formed, for example, by reacting a compound of formula (I) with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like. Additionally, acids which are generally considered suitable for the formation of pharmaceutically useful salts from basic pharmaceutical compounds are known.

The term "solvate" means a compound formed by the combination of solvent molecules with molecules or ions of the solute (solvation). Solute can be any of the embodiments of the present invention and the solvent can be water (forming hydrates) or any organic solvent.

The term "metal complex" means a complex of a compound of general formula (I) with a metal ion, which can be the ions of the usual transition metals of the periodic table like Fe, Cu, Zn.

Subclasses of Compounds of General Formula (I)

a) That is a specific subclass of compounds of general formula (I) wherein a hydrazino group can be found in substituent $R^1$. This hydrazino group can be connected to the core structure directly through the N-atom of the hydrazino group (see compounds where $R^1$ is —NH—N=$R^a$) or through a (further) C-atom (see compounds where $R^1$ is —CH=N—NH—$R^e$ [here $R^3$ is preferably —(CH$_2$)$_n$-heterocyclyl2, wherein heterocyclyl2 is a 5- to 6-membered saturated ring system with 3 to 5 carbon atoms and 1 to 2 nitrogen heteroatom(s) (with the proviso that when $R^1$ and $R^2$ are hydrogen, $R^3$ is different from 1-pyrrolidinylmethyl)]. These two possibilities form together a subclass since these groups carry a hydrazino group which gives a specific character to these side chains.

b) That is another specific subclass of compounds of general formula (I) wherein a nitrogen atom can be found in beta position to that carbon atom of the core structure which carries substituent $R^3$, see compounds where $R^3$ is —$CHR^f$—$NHR^g$ (see the relating definitions above).

Here a further characteristic subgroup is formed by those compounds where $R^f$ and $R^g$ form, together with the adjacent atoms a heteroaryl derived from a partially saturated bicyclic or tricyclic ring system (heteroaryl2 group) or a saturated bicyclic ring system containing 2 N atoms as heteroatoms (which group is optionally substituted with an oxo group). These compounds have at least a bicyclic group in this side chain.

Those compounds are also members of this subgroup where $R^3$ is —$(CH_2)_n$-heterocyclyl2, wherein heterocyclyl2 is a 5- to 6-membered saturated ring system with 3 to 5 carbon atoms and 1 to 2 nitrogen heteroatom(s) (with the proviso that when $R^1$ and $R^2$ are hydrogen, $R^3$ is different from 1-pyrrolidinyl-methyl).

Compound of example 36 is also a member of this subgroup [where $R^3$ is ((2-(3-methyl-3H-diazirin-3-yl)ethyl)(prop-2-yn-1-yl)amino)methyl].

Compounds of general formula (I) wherein $R^1$ is different from H and/or Me also form specific subgroup(s) within the claimed scope.

Preparation of the Compounds

The compounds of the present invention can be prepared according to methods known from the state of the art. Compounds containing a 2-hydrazino group can be synthetized by the condensation of 2-hydrazinyl-8-oxy-quinoline and the appropriately substituted carbonyl-compound. 7-substituted compounds and compounds wherein the substituents in positions 7 and 8 form an oxazine ring, can be prepared by Mannich- or Betti-reactions as exemplified, starting from the appropriately substituted reactants.

The starting materials are available commercially. The starting compound 2-hydrazino-8-quinolinol can be prepared as disclosed in the state of the art (Terry, Rudolph F. Przystal J. P. Phillips 1967) by reacting 2-chloro-8-quinolinol and hydrazine, followed by precipitation of the product with water and optional recrystallization.

The compounds according to the present invention can be prepared by using methods known from the state of the art.

7-substituted compounds can be prepared by Mannich-reaction (Mannich, C.; Krösche, W. (1912), M. Tramontini, L. Angiolini, 1994) or Betti-reactions (Betti, M., 1903) as exemplified, starting from the appropriately substituted reactants. Mannich-reaction is a typical multicomponent reaction which requires an amine, a carbonyl component and an acidic C—H bond presenting molecule in the classical reaction set-up.

Aminomethylation of 8-hydroxyquinolines employing Mannich-type of reaction condition leads to primarily o-substituted (7-substitution) phenolic species. If the 5-position is unsubstituted a side-reaction could occur at the 5-position, accompanying the favoured 7-substitution leading to 5,7-diaminomethylated bis-Mannich products. In order to avoid such a side reaction, the stoichiometry and the addition should be carefully controlled. The reaction condition varies from room temperature to reflux in the corresponding media (such as alcohol, pyridine, acetic acid etc.) depending on the reactivity of the acidic C—H containing species as well as the substitution pattern. In the case of unreactive components the reaction time could reach several days therefore often MW heating is applied to accelerate the reaction. As the carbonyl component aqueous formaldehyde or paraformaldehyde is used. Choosing the appropriate reaction conditions (i.e. reactant concentration, solvent, reaction temperature) belongs to the knowledge of the person skilled in the art.

Preparation of substituted 8-hydroxyquinolines by classical Mannich reaction has been disclosed in: Wangtrakuldee, P., et al., 2013; Sosic, I., et al., 2013; Enquist, P. A., et al., 2012; Shaw, A. Y., et al., 2010; Fernandez-Bachiller, M. I., et al., 2010; Li, L. and B. Xu, 2008; Negm, N. A. et al., 2005; M Movrin, et al., 1980.

Excess formaldehyde (2 eq.) with primary amine components leads to [1,3]oxazino-quinoline derivatives (7 and 8 substitution) which loses the second equivalent formaldehyde in acidic condition giving the open-chain Mannich product. (Szatmári, I. and F. Fülöp, 2013).

The starting substituted 8-hydroxyquinolines are commercially available.

There are several variants of the Mannich reaction, described e.g. in: N. Risch et al. 1998. A special alteration is the modified three-component Mannich reaction, in which the C—H acid is replaced by an electron-rich aromatic compound (e.g. phenol-type of compounds) such as 1- or 2-naphthol, quinolinol or isoquinolinol. This variation is also called Betti reaction (Betti, M. Org. Synth. Coll. Vol., 1941, 1, 381.). They are good C-nucleophiles with the ability to undergo ready addition to C=N double bonds in modified Mannich condensations (Szatmári, I. and F. Fülöp, 2013). Phenols can be reacted with dihydroisoquinolines that give tetrahydroisoquinolinyl-methyl-phenolic species under solventless condition with microwave heating (Szatmári, I. et al., 2006).

Compounds containing a hydrazone in position $R^1$ can be synthetized by the condensation of 2-hydrazinyl-8-hydroxy-quinoline and the appropriately substituted carbonyl-compound.

The starting compound 2-hydrazino-8-quinolinol can be prepared as disclosed in the state of the art (Terry, R F., Przystal J. P. Phillips, J. 1967) by reacting 2-chloro-8-quinolinol and hydrazine, followed by precipitation of the product with water and optional recrystallization. 2-halogeno-8-quinolinols can be obtained in a multistep reaction sequence from 8-hydroxy-quinoline. (Petitjean, A., N. Kyritsakas, and J. M. Lehn, 2005).

The reaction schemes given at the examples provide further details about the prepration processes.

Biological Effects of the Compounds of the Invention

From the point of malignant transformation to metastasis and proliferation, the evolution of tumors is influenced by mutations and selection. The cancer genome is shaped by a high rate of error-prone mutations, which gives rise to heterogeneous clones characterized by extensive genetic, epigenetic, transcriptional and phenotypic diversity. Chemotherapy can be considered as an additional selective pressure favoring the selection of drug-resistant cells that outgrow non-resistant peers. Collateral sensitivity of MDR cells indicates that resistance can be interpreted as a trait that may be targeted by new drugs. This concept is substantially different from the failed strategy of transporter inhibition, which requires the co-administration of cytotoxic drugs with small-molecule P-gp inhibitors devoid of intrinsic toxicity. In contrast, the toxicity of P-gp-potentiated MDR-selective compounds is increased by P-gp in several MDR cell lines selected with cytotoxins, or genetically engineered to overexpress P-gp.

In cancer, collateral sensitivity may be considered as a form of synthetic lethality ensued by the resistance phenotype (such as P-gp) and the toxicity of a drug. The paradoxical hypersensitivity of P-gp-expressing multidrug-resistant cells was initially perceived as a curious anomaly (Herman, T S et al. 1979). As more and more compounds were shown to specifically target resistant cells, it became clear that the collateral sensitivity conveyed by P-gp represents a promising strategy for targeting MDR cancer (Szakács, G et al. 2014). However, a major limitation of these findings is that the causative role of P-glycoprotein in collateral sensitivity was not always assessed, and contribution of further cellular alterations associated with the particular model could not be excluded. In fact, in several cases more thorough study showed that the the toxic effect of prior art compounds were cell-type specific and not P-gp-specific which excluded a robust effect and taught away from medical use. With certain exceptions the prior art MDR-selective compounds did not show consistent P-gp-dependent toxicity.

In contrast to MDR-selective compounds of the prior art, the toxicity of the compounds of the invention was found to be consistently increased by P-gp in several MDR cell lines selected with cytotoxins, or genetically engineered to over-express P-gp. We have shown that P-gp expression is both necessary and sufficient to convey collateral sensitivity to the novel MDR-selective compounds of the invention.

We have compared the compounds of the invention with the closest prior art structures having MDR selectivity, i.e. NSC693871 and NSC693872.

Compounds having P-gp potentiated MDR-selective activity can be characterized by their inhibitory concentration (IC) with regard to a specific cancer cell line. Usually the IC value is given at a certain percentage ratio of non-inhibited molecules or surviving cells. For example an $IC_{20}$ value of a compound on a cell line means that at this inhibitory concentration of the compound 80% of the cells are killed whereas 20% of the cells are still viable. A further characteristic of MDR-selective drugs is the selectivity ratio (SR), which is the ratio of the IC value measured in a non-multidrug resistant cell line to (i.e. divided by) the IC value measured in the corresponding transformed, multidrug-resistant cell line. The inverse value, the resistance ratio (RR) is calculated as the ratio of a compound's IC value against a multidrug resistant cell line divided by the parallel IC value of the same compound against a control non-multidrug resistant cell line. The Activity Index (AI) is calculated here as the ratio of the compound's selectivity ratio (SR) and the the compound's $IC_{50}$ value against the resistant cell. The AI reflects the level of simultaneous toxicity and selectivity towards multidrug-resistant cancer cells.

In a preferred embodiment a cell line derived from a solid tumor is used for the testing of the activity of MDR-selective compounds. Cell lines derived from different hyperproliferative diseases may exhibit different SR values to the same compound.

In a further preferred embodiment a cell line recombinantly expressing a P-gp multidrug resistance transporter protein is used for the testing of the activity of MDR-selective compounds.

In a further preferred embodiment a multidrug resistant cell line which has been made resistant by serial administration of a cytotoxic compound, and thus expressing a P-gp transporter protein, is used for the testing of the activity of MDR-selective compounds.

We have unexpectedly found that 8-hydroxyquinoline derivatives of the invention exhibit selective cytotoxicity against multidrug-resistant cancer cells, allowing the effective growth inhibition of such cancer cells. Furthermore, we have surprisingly found that 8-hydroxyquinoline derivatives according to the present invention are capable of selectively inhibiting the growth of multidrug-resistant cell lines, e.g. a P-gp-overexpressing human uterine sarcoma cell line, the MES-SA/Dx5 cell line (Table 1), and the selectivity ratio expressed as $IC_{50}$ ratio between MES-SA/Dx5 and MES-SA cells significantly exceeds the selectivity which has been previously experienced in connection with the compounds of the same chemical class of 8-hydroxyquinolines belonging to the state of the art, i.e. NSC693871 and NSC693872 (Table 2a).

Furthermore, the compounds exert their selective cytotoxicity at low $IC_{50}$ values which is reflected by a significantly higher activity index as compared to prior art compounds NSC693871 and NSC693872 (see Table 2b).

As explained above, the compounds of the present invention have proved to have a robust effect among various cell types indicating that this effect is independent of the cancer type and depends on the MDR property of the cell, or more specifically P-gp expression. This finding is supported by experiments on two further MDR models engineered by retroviral transfection of P-glycoprotein, an epidermoide carcinoma cell line and a polarised epithelial canine kidney (Madin-Darby canine kidney 2, MDCK II). Experiments suggested the results to be valid in primary cells obtained from multidrug resistant mouse breast cancer (Tables 3 and 4).

Since the P-gp mediated MDR selective toxicity is in fact dependent on the presence of functional multidrug transporter protein P-gp in cell membranes, inhibiting P-gp should reverse this selective toxicity. In fact, in the presence of tariquidar, a selective inhibitor of P-gp function, the toxicity of the compounds selectively diminishes in multidrug-resistant MES-SA/Dx5 cells, while the toxicity is unchanged against parental MES-SA cells (Table 5).

Thus, the acquisition of the new phenotypic trait of drug resistance comes at a cost to the cancer cell. In this context (acquired resistance to anticancer agents), the overexpression of P-gp transporter that confers MDR can prove to be lethal to the cell in the presence of P-gp-potentiated MDR-selective compounds.

The MDR-selective compounds of the present invention efficiently exploit this "fitness cost" and the ensuing paradoxical hypersensitivity that is invariably associated with the expression of P-gp. Collateral sensitivity of MDR cell lines indicates that drug resistant cancer expressing P-glycoprotein can be selectively targeted.

In addition to the above, we have unexpectedly found that treatment, even and preferably a single, high-dose treatment with the new P-gp-potentiated MDR-selective 8-hydroxyquinoline derivatives according to the invention results in the loss of P-gp expression and re-sensitization to chemotherapy.

For example, after even a single treatment, MES-SA/Dx5 cells exhibit a stable phenotype characterized by the loss of P-gp and a renewed sensitivity to doxorubicin (FIG. 3). This newly acquired P-gp-negative, chemotherapy-sensitive phenotype was stable for up to 30 passages (~4 months, data not shown).

MDR cell lines usually provide a very high overexpression of multidrug resistance transporters which is not the case with actual multidrug-resistant cells in a patient. To obtain a more realistic model of drug resistance primary breast tumor cell cultures were established from doxorubicin resistant brca1−/−/p53−/− spontaneous mouse mammary carcinoma, which express P-gp at a relatively low, i.e. clinically relevant levels. These primary cells were studied at a low passage number and the effect of in vitro treatment by the compounds of the invention was evaluated. We have surprisingly found that 8-hydroxy-quinoline derivatives presented in this invention are capable of selectively eliminating multidrug-resistant primary cells in this more realistic model of clinical drug resistance.

Moreover, certain MDR-selective 8-hydroxy-quinoline derivatives also eradicate P-glycoprotein expression in this primary breast tumor culture. We showed in case of several compounds a significant loss in P-gp-mediated calcein efflux capacity of these primary cells, suggesting that the invented P-gp potentiated MDR-selective compounds can effectively revert to the MDR phenotype of cells towards a non-MDR phenotype.

These findings further support that P-gp-potentiated MDR-selective compounds are able to deplete tumors of P-gp-positive MDR cells even in a realistic model of clinical drug resistance.

This rapid phenotype-switch of established human MDR cell lines such as MES-SA/Dx5 and primary cells obtained from multidrug resistant mouse breast cancer, induced by 8-hydroxyquinoline derivatives of the invention exceeds or, in case of several compounds significantly exceeds the effect which has been previously experienced in connection with the compounds of the same chemical class of 8-hydroxyquinolines belonging to the state of the art, i.e. NSC693871 and NSC693872 (Table 6, FIG. 1).

As a summary, as it comes from the above analysis, compounds of the present invention, when applied for treating MDR, can act in two different ways.

a) They can selectively destroy cells expressing the transporter responsible for drug efflux-based multidrug resistance (i.e. P-gp).

b) They can effectively suppress the expression of the transporter (i.e. P-gp) in such cells thereby rendering the cells vulnerable to treatment with cytotoxic drugs. This approach provides a new and potentially more effective possibility for treating multidrug-resistant cancer or reversing the clinically observed multidrug-resistance.

The compounds of the present invention have both of the above effects—here we underline that this type of combined effect ("double action") is not known in the prior art and the closest structural analogue compounds do not have this combined effect—, and therefore they ensure a particularly effective way in the fight against multidrug-resistant cancers where, as a first effect, a direct killing of MDR-resistant cells having high P-gp expression is carried out and, as a second effect, the P-gp expression is decreased/abolished in the surviving cells (i.e. multidrug-resistance in the surviving cancer cells is reversed), making them sensitive to usual chemotherapic agents. Moreover, this second effect preferably can be reached even by a single treatment and this efficiency is a further surprising feature of the invented compounds.

This double action against the MDR cancer cells makes the invented compounds particularly effective against multidrug-resistant cancers.

Unity

Since the above effect b) was not known from the compounds having the same core, this effect [alone or in combination with above effect a)] ensures the unity for all the claimed compounds of general formula (I).

Therapeutic Regimens

The above-mentioned approach may be exploited clinically in the treatment of multidrug-resistant cancers according to several protocols.

For example, when the P-gp-potentiated MDR-selective agent is administered in a concentration suitable for directly inhibiting or killing cancer cells, the agent exerts its activity as a selective cytotoxic agent.

In a further variant, treatment with a P-gp-potentiated MDR-selective agent eliminates transporter expression, resulting in a phenotype-switch accompanied by the loss of P-gp-expression in surviving cancer cells that, as a result, become susceptible to chemotherapy. Surprisingly, even a single treatment shows a remarkable effect, which ensures a direct suppression of transporter expression in MDR cells. In comparison with closest prior art compounds, wherein the ratio of P-gp-negative cells in the surviving cell population is very low, the compounds of the invention typically achieve a very high ratio of P-gp-negative cells and this phenotype remains stable.

Thus, in a therapeutic regimen, one or more P-gp-potentiated MDR-selective agent(s) is/are administered to the patient in one or more effective dose(s) to eliminate the MDR phenotype in the tumor thereby rendering the tumor sensitive to P-gp substrate chemotherapeutic agents. In a specific embodiment the patient has a tumor which is resistant to chemotherapeutic agents transportable by P-gp. In a preferred embodiment in this therapeutic regimen P-gp-potentiated MDR-selective agent(s) of the invention is(are) administered to the patient. Thereafter one or more chemotherapeutic agent(s) transportable by P-gp is/are administered to the patient to kill sensitized tumor cells.

According to a still further therapeutical regimen, an MDR-selective agent is administered simultaneously with existing conventional chemotherapy in order to prevent the development of multidrug-resistance ("concomitant or concurrent systemic therapy").

In a further developed administration scheme a combination of compounds is applied to prevent the recurrence of the resistant phenotype. According to this scheme a first chemotherapeutic compound, which is a P-gp-potentiated MDR selective compound, is administered for a given period thereby killing P-gp-expressing cells and arriving at a non-P-gp-expressing phenotype in the eventually surviving cells. Thus, the surviving cells are eliminated by a further cytotoxic chemotherapeutic compound. (This type of regimen is also called an "adjuvant systemic therapy".) In a preferred embodiment in a further stage of the treatment one or both compounds of the combination (comprising a P-gp-potentiated MDR selective and a further cytotoxic chemotherapeutic compound) is changed and these new compounds are administered for a similar period and according to a similar regimen as previously. Thereby the recurrence of the resistant phenotype is prevented. By changing the compounds of the combination the cancer can be eliminated or the number of cancer (tumor) cells can be reduced below a threshold by maintaining a non-resistant phenotype of cancer cells and controlling or killing the cells in the above-described way.

The two compounds of the combination can be administered simultaneously or consecutively.

In an embodiment in the combination therapy of the invention fixed dose combination (FDC) medicinal products containing two or more active substances within a single pharmaceutical form are applied. Potential advantages of fixed dose combination products beside the benefit of the combined effects of active substances given together may also include the counteracting by one substance of an adverse reaction produced by another one, as explained above. Moreover simplification of therapy, leading to improved compliance, is a further advantage.

In a further developed administration scheme multiple MDR selective compounds of the invention are applied.

In a preferred embodiment exploiting the collateral sensitivity of multidrug-resistant cells would include the determination of the MDR mechanisms or P-gp-potentiated sensitivity in a specific patient's tumor. This could be achieved by molecular pathology of tumor samples or, if it occurs during the course of therapy, by direct in vivo imaging of transporter function. Primary tumor cells can be isolated and tested. Alternatively, human tumors can be expanded in mice, the resultant tumor is explanted into culture and human cancer cell lines can be isolated [Kamiyama, Hirohiko et al. 2013]. Another approach is the study of circulating tumor cells (CTC). Further in vivo and in vitro approaches for the detection of MDR in the laboratory and the mechanisms of MDR in cancers are reviewed by Wu, Qiong et al. [Wu, Qiong et al. 2014].

Based on the test result, if P-gp is expressed in the cancer cells, a P-gp-potentiated MDR selective regimen can be applied in itself or added to the chemotherapy, to kill multidrug-resistant cells that express the transporter.

Another approach can be to automatically add a P-gp-potentiated MDR selective compound to all chemotherapy regimens of cancers likely to express the P-gp transporter, some time during the course of treatment. More specifically if it is known that the chemotherapy drug applied often elicits P-gp-expression mediated MDR, additional administration of the P-gp-potentiated MDR selective compounds of the invention is advisable.

Medical Indications and Pharmaceutical Preparations

On the basis of the surprisingly improved selectivity, improved toxicity, the ability to induce a rapid loss of P-gp expression, and the persistent activity of the compounds in a realistic in vitro model of clinical drug resistance, the compounds according to the present invention are suitable for the treatment of hyperproliferative diseases, especially multidrug-resistant cancer and metastatic cancer when administered individually or in combination with a further chemotherapeutical agent. Forms of hyperproliferative diseases susceptible to the development of multidrug-resistance include solid tumors, such as sarcomas and carcinomas. Additional types of multidrug resistant hyperproliferative diseases, wherein the compounds according to the present invention can be used, are e.g. multidrug resistant prostate, breast, colon, bladder, cervical, skin, testicular, kidney, ovarian, stomach, brain, liver, pancreatic or esophageal cancer, lymphoma, hematological tumors including leukemias, polycythemia vera, Hodgkin's disease, non-Hodgkin's lymphoma, multiple myeloma and myelodysplasia.

Compounds according to the present invention can be used alone or in combination with known cytostatic or chemotherapeutical agents, wherein at least one compound according to the present invention is administered simultaneously, consecutively or prior to cytostatic or chemotherapeutical treatment. Agents used in connection with the compounds of the present invention can be selected from e.g. chemotherapeutical agents, such as alkylating agents, alkylating-like agents, antimetabolites, anti-microtubule agents, topoisomerase inhibitors or anticancer antibodies.

According to a further aspect of the present invention, compounds of the general Formula I as defined above are provided for use as medicaments.

According to a still further aspect of the present invention, the compounds of the general Formula I are provided as defined above for use individually or in combination with a second therapeutical agent in the treatment of cancer, especially multidrug resistant cancer, wherein the mentioned second therapeutical agent might be a chemotherapeutical agent or an anti-cancer antibody.

Chemotherapeutical agents include but are not limited to alkylating agents (e.g. cyclophosphamide, busulfan, melphalan, chlorambucil, mechlorethamine, uramustin, ifosfamide, bendamustin, carmustin, lomustin, streptozocin, thiotepa), alkylating-like agents (e.g. cisplatin, carboplatin, nedaplatin, oxaliplatin, satraplatin, triplatin tetranitrate, procarbazine, altretamin, dacarbazine, temozolomide, mitozolomide, nitrosoureas, thiotepa, mytomycin, hexamethylmelamine) antimetabolites (e.g. methothrexate, pemetrexed, fluorouracil, capecitabine, cytarabine, gemcitabine, decitabine, Vidaza, fludarabine, nelarabine, cladribine, clofarabine, pentostatin, thioguanine and mercaptopurine); anti-microtubule agents (e.g. vincristine, vinblastine, vinorelbine, vindesine, vinflunine, paclitaxel, docetaxel, podophyllotoxin, etoposide, tenoposide), topoisomerase inhibitors (e.g. camptothecin, irinotecan, topotecan, etoposide, doxorubicin, mitoxantrone, teniposide, novobiocin, merbarone, and aclarubicin), cytotoxic antibiotics (e.g. actinomycin, bleomycin, plicamycin, mitomycin, doxorubicin, daunorubicin, epirubicin and idarubicin, pirarubicin, aclarubicin and mitoxantrone). In certain embodiments, further chemotherapeutical agents or other active ingredients may be included into the treatment protocol. Administration of a compound of the general Formula I according to the present invention and the chemotherapeutical agent may be simultaneous or sequential, starting either with the administration of a compound of the general Formula I or alternatively, with that of the chemotherapeutical agent.

According to a further aspect of the present invention, compounds of the general Formula I are provided for the treatment of hyperproliferative diseases including cancer, preferably multidrug-resistant cancer and metastatic, multidrug-resistant cancer.

According to a still further aspect of the present invention, compounds of the general Formula I are provided in combinations with chemotherapeutical agents for the treatment of hyperproliferative disorders showing multidrug-resistance or susceptible thereto, especially for those disorders wherein the multidrug-resistance is linked to or resulting from P-gp overexpression. Examples of such hyperproliferative diseases are solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma), prostate, breast, colon, bladder, cervical, skin, testicular, kidney, ovarian, stomach, brain, liver, pancreatic or esophageal cancer, or lymphoma, leukemia or multiple myeloma.

Further examples of diseases that can be treated by administering a compound of the general Formula I alone or in combination with a chemotherapeutical agent are leukemias, including acute leukemias (such as acute lymphocytic leukemia, acute myelocytic leukemia, acute myelogenous leukemia and myeloblasts, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macro globulinemia, heavy chain disease, myelodysplastic syndrome, hairy cell leukemia and myelodysplasia.

According to a further aspect of the present invention, there is provided a method for the treatment of hyperproliferative diseases mentioned above, especially multidrug resistant and metastatic cancer, which comprises administering a person in need of such treatment a therapeutically effective amount of a compound of the general Formula I alone or in combination with a chemotherapeutical agent.

Dosing of the compounds according to the present invention are to be determined by the physician, e.g. according to the type of disease, severity of disease, accompanying therapeutical protocols, the sex, age, physical condition of the patient to be treated. As a guidance, the daily dose of a compound of the Formula (I) or a pharmaceutically acceptable salt thereof can be, for example, between 0.1-1000 mg/kg body weight for adults. The daily dose can be administered in one or more portions. Medicaments according to the present invention containing a compound of the Formula (I) or a pharmaceutically acceptable salt thereof as active ingredient contain the active ingredient in the form of dosage units. Usual routes of administration, e.g. oral or parenteral, are preferred.

Compounds according to the present invention can be prepared and administered in salt form. Pharmaceutically acceptable salts can be selected according to the principles set forth in P. H. Stahl, C. G. Wermuth: Handbook of Pharmaceutical Salts, Wiley, 2008. Salts may result from reactions with acids, e.g. mineral acids such as hydrochloric acid; aliphatic carboxylic acids, e.g. acetic acid; hydroxy-carboxylic acids, sulphonic acids, phosphoric acid derivatives, amino acids, polyhydroxy acids, heterocyclic acids, aromatic carboxylic acids e.g. benzoic acid etc.

Certain compounds according to the present invention can also form salts with bases, e.g. alkali earth metal and alkali metal cations, cations of transitional metal elements, amino acids, ammonia, aliphatic or aromatic amines, quaternary ammonium bases, hydroxy-substituted amines, amino-sugars.

According to the further aspect of the present invention, medicaments are provided which comprise a compound of the present invention or pharmaceutically acceptable salt thereof alone or in admixture with one or more vehicles or auxiliary agents known from the prior art.

The medicament according to the present invention contains the active ingredient usually in the concentration of 0.1-95 percent by weight, preferable in the concentration of 1 to 50 percent by weight, the most preferably, in the concentration of 5 to 30 percent by weight.

Medicaments according to the present invention can be administered orally (e.g. powders, tablets, coated tablets, capsules, microcapsules, dragees, solutions, suspensions or emulsions), parenterally (e.g. in the form of intravenous, intramuscular, subcutaneous or intraperitoneal injections or in the form of an infusion), rectally (e.g. in the form of suppositories), transdermally (e.g. in the form of patches), as implants or locally (e.g. as creams, ointments or patches). Solid, semisolid and liquid medicaments according to the present invention can be prepared according to the processes known per se from the state of the art.

Solid medicaments suitable for oral administration containing a compound of the Formula (I) or a pharmaceutically acceptable salt thereof as pharmaceutically active ingredient can contain vehicles, filling agents (e.g. lactose, glucose, starch, calcium phosphate, microcrystalline cellulose), binding agents (e.g. gelatin, sorbitol, polyvinylpyrrollidone), disintegrants (e.g. croscarmellose, sodium carboxymethylcellulose, crospovidone), tabletting aids (e.g. magnesium stearate, talc, polyethyleneglycol, silicic acid, silicon dioxide) or surfactants (e.g. sodium lauryl sulphate).

Liquid medicaments intended for oral administration containing a compound of the Formula (I) or a pharmaceutically acceptable salt thereof as active ingredient can be presented in the form of e.g. solutions, suspensions or emulsions and can contain suspending agents (e.g. gelatin, carboxymethyl cellulose), emulsifying agents (e.g. sorbitan monooleate), solvents (e.g. water, oils, glycerol, propylene glycol, ethanol), pH adjusting agents (e.g. acetate, phosphate, citrate buffers) or stabilizing agents (e.g. methyl-4-hydroxy-benzoate).

Liquid medicaments containing a compound of the Formula (I) or a pharmaceutically acceptable salt thereof suitable for parenteral administration are sterile isotonic solutions, which contain a pH-adjusting agent and a stabilizing agent besides the solvent.

Semisolid medicaments containing a compound of the Formula (I) or a pharmaceutically acceptable salt thereof as active ingredient, e.g. suppositories, contain the active ingredient of the Formula (I) homogeneously dispersed in the base of the suppository (e.g. in polyethylene glycol or cocoa butter).

Medicaments containing a compound of the Formula (I) or a pharmaceutically acceptable salt thereof as active ingredient can be produced by the methods of pharmaceutical technology known from the state of the art. The active ingredient is admixed with solid or liquid vehicles or auxiliary agents and is converted into a pharmaceutical dosage form. Vehicles and auxiliary agents and the processes suitable for the manufacture of the medicament are known from the art (Martin, E. W, 1995).

Medicaments according to the present invention containing a compound of the Formula (I) or a pharmaceutically acceptable salt thereof as active ingredient contain the active ingredient in the form of dosage units.

Below the invention is further illustrated by exemplary experiments on biological function and effect of the compounds of the invention as well as non-limiting example for compounds and their preparation.

Biological Characteristics of the Compounds of General Formula I

1. Cytotoxicity Towards Multidrug-Resistant Cancer Cells

Cytotoxic activity of the compounds against multidrug-resistant cells can be characterized by their $IC_{50}$ value measured in MES-SA/Dx5 cell line.

Results $IC_{50}$ values of the state of the art and several example compounds presented in this invention are shown in Table 1.

TABLE 1

IC$_{50}$ values (Mes-sa/Dx5 cell line, PrestoBlue assay)

| Compound | IC$_{50}$ (nM) |
| --- | --- |
| NSC693871 (prior art) | 1474 |
| NSC693872 (prior art) | 1583 |
| Example 4 | 160 |
| Example 8 | 161 |
| Example 9 | 118 |
| Example 13 | 127 |
| Example 14 | 130 |
| Example 18 | 157 |
| Example 25 | 131 |
| Example 26 | 133 |

From the results shown in Table 1, it is evident that the compounds presented in this invention show significantly higher cytotoxicity in MES-SA/Dx5 multidrug-resistant cells as compared to 8-hydroxy-quinoline derivatives NSC693871 and NSC693872 known from the state of the art. This unexpected higher cytotoxicity is approximately one order of magnitude higher than the state of the art.

Assay Method

The human uterine sarcoma cell line MES-SA and its doxorubicin resistant counterpart MES-SA/Dx5 were obtained from ATCC (MES-SA: No. CRL-1976™, MES-SA-Dx5: No. CRL-1977™). MES-SA/Dx5 cells express high levels of P-gp, and therefore are multidrug resistant (MDR). Cells were cultured in DMEM supplemented with 10% FBS, 5 mmol/L glutamine and 50 unit/mL penicillin and streptomycin (Life Technologies).

Cell survival was measured by the PrestoBlue® Cell Viability Reagent (Life Technologies, USA). Cells were seeded in 100 µl medium at a density of 5000 cells/well in 96-well plates; the serially diluted drug was added the following day. Cells were then incubated for 72 hours at 37° C. in 5% CO2; the drug containing medium was removed, and the PrestoBlue® reagent was added according to the manufacturer's instructions. Fluorescence of the cells was measured by a Perkin Elmer EnSpire multimode plate reader or Perkin Elmer Victor X3 microplate reader. Data were background corrected and normalized to untreated cells. Curves were fitted with the help of Prism software using the sigmoidal dose-response model. Curve fit statistics were used to determine IC$_{50}$ values. Differences between the IC$_{50}$ values of the respective cell lines were analyzed by two-sided paired unpaired Student's t test and results were considered statistically significant at a P value of <0.05 (*) or 0.01 (**).

2. Selectivity Towards Multidrug-Resistant Cancer Cells

A main characteristic of the compounds presented in this invention is the selective cytotoxicity (selectivity) towards multidrug-resistant cancer cells.

Results

Selectivity towards multidrug-resistant cells is expressed as the ratio of the IC$_{50}$ value measured in the parental MES-SA and multidrug-resistant MES-SA/Dx5 cell line (Selectivity Ratio, SR).

TABLE 2a

Selective toxicity towards the multidrug-resistant MES-SA/Dx5 cell line of the state of the art and some of the example compounds of the present invention

| Compound | IC$_{50}$ (nM) in MES-SA cell line | IC$_{50}$ (nM) in MES-SA/Dx5 cell line | Selectivity Ratio (SR) |
| --- | --- | --- | --- |
| NSC693871 (prior art) | 6248 | 1474 | 4.2 |
| NSC693872 (prior art) | 7808 | 1583 | 4.9 |
| Example 3 | 11258 | 727 | 16.2 |
| Example 5 | 40484 | 1973 | 20.9 |
| Example 9 | 2258 | 118 | 20.4 |
| Example 15 | 12388 | 594 | 23.8 |
| Example 25 | 2913 | 131 | 22.3 |
| Example 26 | 2262 | 130 | 17.6 |
| Example 27 | 6090 | 310 | 19.9 |
| Example 28 | 8652 | 442 | 19.7 |
| Example 29 | 40550 | 2093 | 19.2 |
| Example 30 | 23840 | 1220 | 19.3 |

In comparison to the 8-hydroxyquinoline derivatives NSC693871 and NSC693872 known from the state of the art, the compounds presented in this invention show an unexpectedly higher (4-5 fold) selective cytotoxicity towards the multidrug resistant MES-SA/Dx5 cells, as revealed by the ratio of IC$_{50}$ values measured in MES-SA parental and MES-SA/Dx5 multidrug-resistant cells (Selectivity Ratio, SR).

A novel characteristic of the compounds presented in this invention is that they exert their selective cytotoxicity at low IC$_{50}$ values. Simultaneous toxicity and selectivity towards multidrug-resistant cancer cells is reflected by the Activity Index (AI) of the compounds, which is the ratio of the selectivity ratio (SR) and the IC50 value on the resistant cell line.

TABLE 2b

Activity index (AI = SR/IC$_{50}$) values of the state of the art and some of the example compounds of the present invention

| Compound | IC$_{50}$ (µM) Dx5 | SR | Activity Index (AI) |
| --- | --- | --- | --- |
| NSC693871 (prior art) | 1.47 | 4.2 | 2.9 |
| NSC693872 (prior art) | 1.58 | 4.9 | 3.1 |
| Example 4 | 0.16 | 5.9 | 36.8 |
| Example 8 | 0.16 | 13.5 | 84.2 |
| Example 9 | 0.12 | 20.4 | 173.0 |
| Example 14 | 0.13 | 7.8 | 59.9 |
| Example 15 | 0.59 | 23.8 | 40.0 |
| Example 25 | 0.13 | 22.3 | 169.9 |
| Example 26 | 0.13 | 17.6 | 135.5 |
| Example 27 | 0.31 | 19.9 | 64.2 |
| Example 28 | 0.44 | 19.7 | 44.6 |

The results shown in Table 2b clearly demonstrate that the compounds presented in this invention are much more active in vitro (more cytotoxic and more selective) than the state of the art compounds, possessing at least one order of magnitude higher Activity Indices (AI).

3. Robustness of the Selectivity

The selective toxicity of MDR selective compounds presented in this invention is robust which means that it is not dependent on specific alterations present in specific MDR cell lines. The compounds presented in this invention proved to be selectively cytotoxic against different cell lines engineered to overexpress P-gp which further supports the finding that P-gp expression is a necessary and sufficient condition of MDR-selectivity of these compounds of the invention.

Results

Data on selective toxicity (expressed as Selectivity Ratio, SR) in two MDR models engineered by retroviral transfection of P-glycoprotein (A431/A431-B1 and MDCK II/MDCK II B1 cell lines) are presented in Table 3 and Table 4.

TABLE 3

Selective toxicity of the state of the art and some example compounds presented in this invention in A431 and A431-B1 cell lines

| Compound | Selectivity Ratio (SR) (A431/A431-B1) |
|---|---|
| NSC693871 (prior art) | 3.8 |
| NSC693872 (prior art) | 1.9 |
| Example 3 | 14.4 |
| Example 4 | 11.7 |
| Example 6 | 11.5 |
| Example 7 | 12.6 |
| Example 10 | 11.2 |
| Example 14 | 13.7 |
| Example 16 | 24.7 |
| Example 17 | 12.6 |
| Example 19 | 24.7 |
| Example 20 | 13.2 |
| Example 22 | 18.8 |
| Example 26 | 11.2 |
| Example 27 | 12.6 |
| Example 29 | 25.1 |
| Example 30 | 11.5 |
| Example 37 | 16.7 |

TABLE 4

Selective toxicity of the state of the art and some example compounds presented in this invention towards MDCK II and MDCK II B1 cell lines

| Compound | Selectivity Ratio (SR) (MDCK II/MDCK II B1) |
|---|---|
| NSC693871 (prior art) | 4.4 |
| NSC693872 (prior art) | 3.1 |
| Example 3 | 9.5 |
| Example 9 | 16.8 |
| Example 12 | 8.3 |
| Example 20 | 10.0 |
| Example 25 | 9.4 |
| Example 26 | 8.0 |
| Example 27 | 8.0 |
| Example 29 | 17.1 |
| Example 30 | 16.1 |
| Example 37 | 8.9 |

The results shown in Table 3 and 4 clearly demonstrate that the compounds presented in this invention are much more selective (as expressed by their SR values) than the state of the art compounds on other MDR models as well. These findings confirm the results obtained with the Messa/Dx5 cell lines (presented in Table 2a).

Assay Method

A431 is a human epidermoid carcinoma cell line. Its derivative, the A431-B1 cell line expresses P-gp due to retroviral transfection of the mdr1 gene Türk, D. et al (Türk, D. et al., 2009). MDCK II is a canine kidney cell line. MDCK II B1 was created by inserting the mdr1 gene with transposons [Pape V F S et al. 2015] Both cell express P-gp stably, and show a stable MDR phenotype. Culture conditions were identical as in the case of MES-SA cells.

4. Selective Toxicity is P-Gp Dependent as Shown by P-Gp Inhibitor Tariquidar

The selective toxicity of the compounds presented in this invention towards multidrug-resistant cells is indeed linked to P-gp function, as is proven by the effect of the chemical inhibition of P-gp function on the toxicity of the compounds against MDR cells.

Results

In the presence of tariquidar (an inhibitor of P-gp function), the toxicity of the compounds selectively diminishes in multidrug-resistant MES-SA/Dx5 cells, while the toxicity is unchanged against parental MESSA cells, which is reflected by a decrease in the selectivity ratio (SR (TQ)).

TABLE 5 the SR, SR (TQ) and their SR/SR (TQ) values corresponding to the state of the art and some example compounds presented in this invention

| Compound | SR | SR (TQ) | SR/SR (TQ) |
|---|---|---|---|
| NSC693871 (prior art) | 4.2 | 1.4 | 3.0 |
| NSC693872 (prior art) | 4.9 | 2.6 | 1.9 |
| Example 3 | 16.2 | 1.5 | 10.4 |
| Example 5 | 20.9 | 1.2 | 16.7 |
| Example 7 | 13.4 | 1.3 | 10.3 |
| Example 9 | 20.4 | 1.8 | 11.7 |
| Example 15 | 23.8 | 1.4 | 16.5 |
| Example 16 | 10.3 | 0.9 | 11.7 |
| Example 25 | 22.3 | 1.6 | 14.0 |
| Example 26 | 17.6 | 1.7 | 10.4 |
| Example 27 | 19.9 | 1.6 | 12.8 |
| Example 28 | 19.7 | 1.6 | 12.7 |
| Example 30 | 19.3 | 1.3 | 14.5 |

The results shown in the Table 5 demonstrate that the selective toxicity of the compounds of the general Formula I is linked to the function of P-gp. Furthermore, this observed P-gp dependency of the selective toxicity is valid for the entire SR range, that is to say P-gp-potentiated toxicity is not dependent on the selectivity ratio (SR) values.

In contrast, the two 8-hydroquinoline derivatives NSC693871 and NSC693872 known from the state of the art, retain a partial selective toxicity in the presence of P-gp inhibitors, suggesting that their selective toxicity is only partially dependent on the activity of P-gp. This is demonstrated by their lower SR/SR (TQ) values as compared to the example compounds of the present invention. The proven role of P-gp function in the selective toxicity of the compounds presented in this invention is a further characteristic which distinguishes them from the two state of the art compounds.

Assay Method

To investigate the contribution of P-glycoprotein to the cytotoxic effect of a compound, cell survival was measured in the presence of the P-glycoprotein inhibitor tariquidar (1 µM). Tariquidar (CAS 206873-63-4) can be obtained e.g. from Selleck, Houston, USA.

5. Effect on P-Gp Expression (MDR Phenotype Switch)

Functional expression of P-glycoprotein (P-gp) in cancer cells reduces the efficacy of certain chemotherapies and shortens patient survival (Szakacs, 2004).

According to a further aspect of the present invention, compounds of the general Formula I may be used for the treatment of MDR cancer by resensitizing cancer cells to conventional chemotherapy through eliminating P-gp expression in MDR cancer.

Results

Surprisingly, a treatment with the compounds presented in this invention resulted in an almost complete loss of P-gp expression in MES-SA/Dx5 cells (FIG. 1, Table 6). In general, already a single treatment provided a very significant increase in the P-gp positive cells in the population surviving the treatment. In contrast, a single treatment with the two 8-hydroxy-quinoline derivatives NSC693871 and NSC693872 known from the state of the art, resulted only in an insignificant loss of of P-gp expression in MES-SA/Dx5 cells (FIG. 1, Table 6), so these compounds practically do not show this effect.

TABLE 6

Fraction of P-gp-positive and -negative cells in the population after treatment with a single dose of the state of the art and two example compounds of the invention

| compound | Fraction of P-gp-positive cells (P4) in the population (%) | Fraction of P-gp-negative cells (P3) in the population (%) |
| --- | --- | --- |
| control | 99.8 | 0.2 |
| NSC693871 (prior art) | 90.9 | 9.1 |
| NSC693872 (prior art) | 92.2 | 7.8 |
| Example 3 (PR-1106) | 11.40 | 88.6 |
| Example 5 (PR-1117) | 32.40 | 67.6 |
| Example 9 (PR-1244) | 1.0 | 99.0 |
| Example 13 (GYKI-194) | 12.00 | 88.00 |
| Example 15 (GYKI-207) | 32.80 | 67.2 |
| Example 18 (GYKI-201) | 19.40 | 80.6 |
| Example 25 (PR-1246) | 7.70 | 92.30 |

This shift of the ratio in P-gp positive and negative cells indicates a phenotype switch resulting in the loss of MDR property of the cells.

Methodology: The P-Gp Switch Assay (FIG. 2.)

One million P-gp-expressing MES-SA/Dx5 cells were plated in a T25 cell culture flask. After 24 hours the compound of interest was added directly to the cells at a concentration corresponding to the $IC_{20}$ value (killing 80% of the cells). After 5 days the culture media was removed, the cells were washed with PBS and the culture medium was exchanged. Cells were monitored daily and the recovery was recorded. The medium was changed every 5 days until the confluence of the cells reached 80%. At 80% confluence the cells were removed by gentle trypsinization, counted by an automated cell counter and stained with Calcein AM, a cellular dye able to detect the function of P-gp (Homolya 1993). P-gp-positivity was evaluated based on the ability of P-gp-expressing cells to extrude Calcein AM.

The above treatment with compounds of the general Formula I results in a new, stable phenotype, with the complete resensitization of cells to conventional chemotherapy consisting of P-glycoprotein substrates such as doxorubicin (FIG. 3).

Curves show the sensitivity of MES-SA/Dx5 cells (P-gp overexpressing cell line established from MES-SA) to doxorubicin before and after treatment with a single dose of a state of the art compound (NSC693872) and two compounds relating to this invention (Example compounds No. 9 and No. 17). The sensitivity of MES-SA cells is shown as a reference (P-gp-negative parental cell line). Whereas treatment with the state of the art compound NSC693872 results in an insignificant decrease of the of P-gp-positive population (see Table 6 and FIG. 1), this small change is not sufficient to influence the resistance of the cells to doxorubicin. In contrast, treatment with a single dose of the compounds according to the present invention is sufficient to resensitize MES-SA/Dx5 cells to doxorubicin. (Values indicate the $IC_{50}$ values (μM) derived from the cytotoxicity curves).

6. Effect on P-Gp Expression (MDR Phenotype Switch) in a Realistic Model of Drug Resistance Compounds according to this invention eradicate P-glycoprotein expression in a primary breast tumor culture obtained from doxorubicin resistant brca1−/−/p53−/− spontaneous mouse mammary carcinoma. This has been demonstrated by the compound of Example 9.

The MDR-selective activity of the compounds according to this invention is causally linked to the expression and function of P-gp. However, the fitness cost associated with P-gp may be restricted to MDR cell lines showing extreme expression levels. To ensure stable overexpression of P-gp, cell lines are maintained under continuous selective pressure, which results in significant changes in gene expression patterns.

Using a genetically engineered model of breast cancer, Rottenberg et al. provided evidence that even low levels of P-gp can confer drug resistance (Rottenberg & Borst n.d.).

We have surprisingly found that 8-hydroxy-quinoline derivatives presented in this invention are capable of selectively eliminating multidrug-resistant cells in a more realistic model of clinical drug resistance, based on primary cell cultures established from doxorubicin resistant brca1−/−/p53−/− spontaneous mouse mammary carcinoma. Tumor pieces derived from Brca1−/−;p53−/− FVB mouse mammary tumors were transplanted orthotopically into the mammary fat pad of wild type FVB mice.

As described by Rottenberg et al. (Pajic et al. 2009), treatment with several cycles of the maximum tolerable dose of doxorubicin invariably lead to drug resistance mediated by the moderate upregulation of Mdr1a and/or Mdr1b (FIG. 4A). Primary cultures from resistant tumors were established. In just 10 passages the culture was depleted of stromal components (FIG. 4B).

Functional expression of P-gp in the primary cells was evaluated by the calcein assay. Whereas the primary cells established from drug resistant tumors express functional P-gp, the efflux capacity of the cells could be eradicated by a single treatment with the compound of Example 9 (FIG. 4D).

The invention is demonstrated by the following examples without limiting the invention by any way.

EXAMPLES

Materials and Methods

All reagents and solvents were purchased from commercial vendors and used without further purification. Concentration of reaction mixtures refers to rotary evaporation under reduced pressure carried out at 40° C. Thin layer chromatography (TLC) was performed on Merck Silica gel 60 F254-precoated TLC plates (0.25 mm thickness) and visualized at 254 nm. Silica gel flash chromatography was performed using silica gel (0.040-0.063 mm) from Merck. NMR spectral data were obtained at ambient temperature unless otherwise specified. 1H (13C) NMR spectra were recorded at 300 (75) MHz or 500 (125) MHz (Instrument: Varian UNITY-INOVA 300 MHz or Varian UNITY-INOVA 500 MHz) in $CDCl_3$ or DMSO-$d_6$. Chemical shifts are reported and shown in parts per million (ppm) and referenced against $CDCl_3$ (7.26 ppm for 1H and 77.0 ppm for 13C) or DMSO-$d_6$ (2.50 ppm for 1H and 39.5 ppm for 13C). Melting points were measured by OptiMelt Automated Melting Point System and are uncorrected.

The detection and determination of the purity of the compounds were in each case carried out by means of HPLC-MS using an AB Sciex 3200QTrap tandem mass spectrometer, PS Series200 HPLC system with ESI positive ionization mode (column: Kinetex C18, 150×4.6 mm 5 μm) and a UV detector (254 nm). The eluent was applied with a flow rate of 0.6 mL/min and followed the given gradient table, in which A represents 0.1% formic acid in water, and B 0.1% formic acid in acetonitrile:

| Time (min) | Percent A |
|---|---|
| 4.0 | 10 |
| 7.0 | 75 |
| 7.5 | 75 |
| 12 | 75 |

Scan Type: enhanced MS; Mass range: 50-800 m/z. Purity of all compounds was ≥95%.

Cell lines used throughout the studies are available from the American Type Culture Collection (Manassas, Va., USA); A431 cell line: ATCC CRL-1555; A431-B1 cell line expresses P-gp due to retroviral transfection of the mdr1 gene and was prepared as described by Türk, D. et al (Türk, D. et al., 2009) using the method of Ujhelly O et al. (Ujhelly O et al. 2003); Mes-Sa: ATCC CRL-1976; Mes-Sa/Dx5: ATCC CRL-1977; MDCK II (or MDCK2): ATCC CRL-2936.

Reaction Scheme to Examples 1 to 5

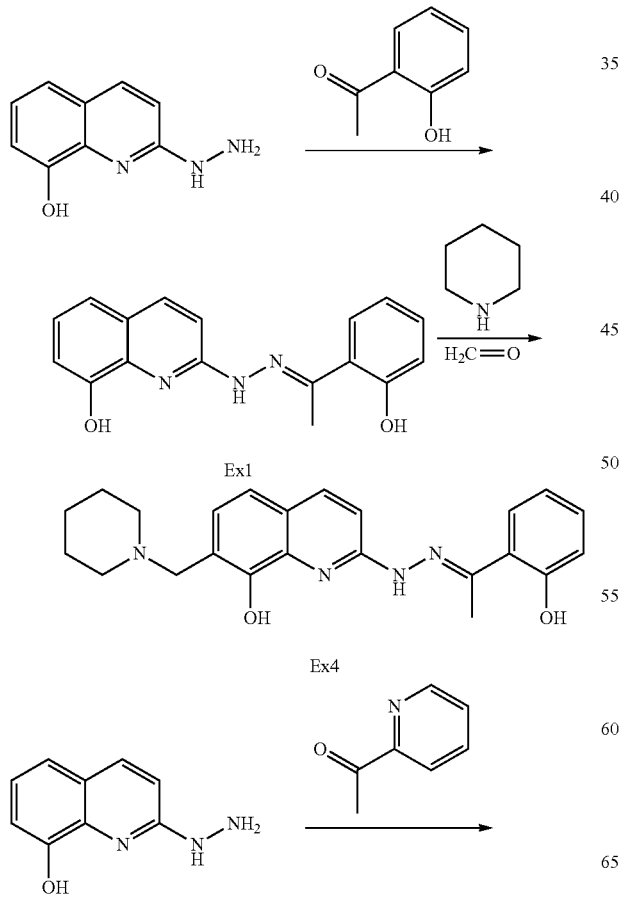

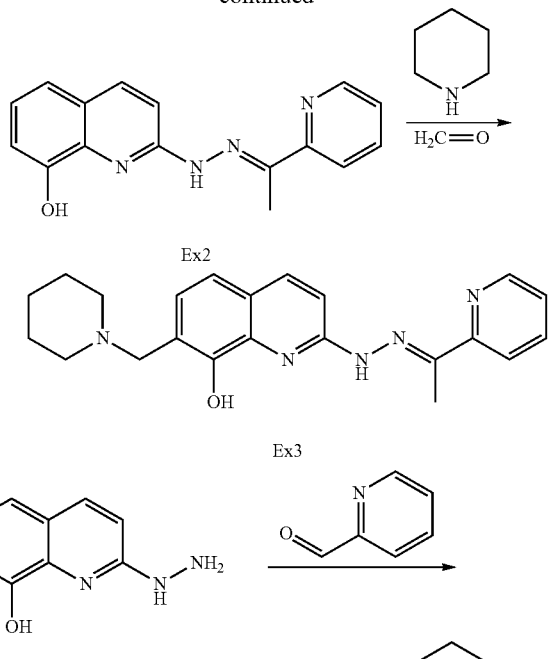

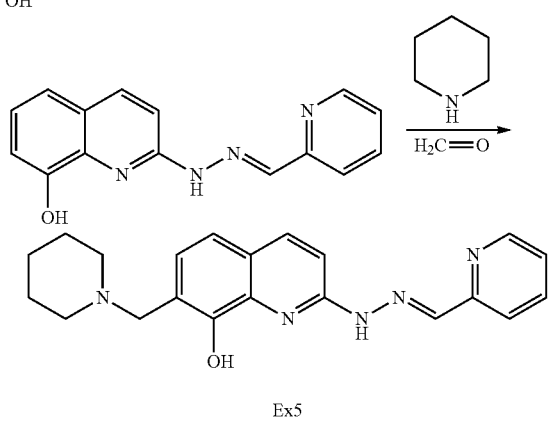

Example 1

(E/Z)-2-(2-(1-(2-Hydroxyphenyl)ethylidene)hydrazinyl)quinolin-8-ol

A solution of 2-hydrazinylquinolin-8-ol (0.35 g, 2 mmol) in ethanol (7 mL) was added 0.272 g (2 mmol) 2'-hydroxyacetophenone and was refluxed for 5 hours. The reaction mixture was allowed to cool down and the obtained precipitate was filtered off, washed with ethanol and crystallized from ethanol to give the titled compound (0.278 g, 47%) as brown crystals. Mp. 225-228° C. 1H NMR (300 MHz, DMSO-$d_6$): δ 2.47 (s, 3H), 6.88-6.89 (m, 2H), 7.07 (d, 1H), 7.18-7.30 (m, 4H), 7.61 (d, 1H), 8.18 (d, 2H), 10.85 (br, 1H), 14.16 (s, 1H). 13C NMR (75 MHz, DMSO-$d_6$): δ 13.0, 110.9, 111.6, 117.1, 118.0, 118.4, 120.1, 123.5, 124.4, 127.4, 130.1, 138.1, 149.9, 150.2, 152.2, 158.1. LCMS RT=3.97 min. ESI+ m/z: 294.3 [M+H+].

Example 2

(E/Z)-2-(2-(1-(Pyridine-2-yl)ethylidene)hydrazinyl)quinolin-8-ol

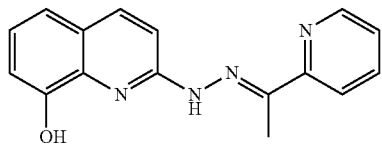 [SMILES: C/C(=N\Nc1ccc2cccc(O)c2n1)c1ccccn1]

A solution of 2-hydrazinylquinolin-8-ol (0.35 g, 2 mmol) in ethanol (7 mL) was added 0.242 g (2 mmol) 2-acetylpyridine and was refluxed for 2 hours. The reaction mixture was allowed to cool down and the obtained precipitate was filtered off, washed with ethanol and crystallized from ethanol to give the titled compound (0.416 g, 75%) as brown crystals. Mp. 213-214° C. 1H NMR (300 MHz, DMSO-$d_6$): δ 2.46 (s, 3H), 7.01 (d, 1H), 7.16 (t, 1H), 7.26-7.35 (m, 2H), 7.48-7.84 (m, 2H), 8.21 (t, 2H), 8.57 (s, 1H), 9.58 (br, 1H). 13C NMR (75 MHz, DMSO-$d_6$): δ 11.3, 110.2, 111.4, 117.9, 119.6, 122.9, 123.4, 124.9, 136.3, 136.9, 138.2, 145.0, 148.4, 151.0, 154.6, 155.6. LCMS RT=3.33 min. ESI+ m/z: 279.0 [M+H+].

Example 3

(E/Z)-7-(Piperidin-1ylmethyl)-2-(2-(1-(pyridin-2-yl)ethylidene)hydrazinyl)quinolin-8-ol

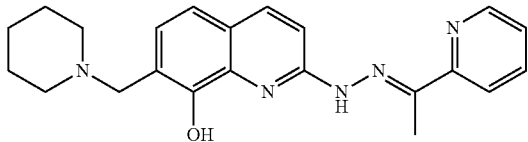 [SMILES: C/C(=N\Nc1ccc2ccc(CN3CCCCC3)c(O)c2n1)c1ccccn1]

The solution of piperidine (135 μL, 0.116 g, 1.37 mmol) in ethanol (4 mL) was added 35% formaldehyde (167 μL, 0.06 g, 2 mmol). The mixture was stirred for 1 hour. Then the solution of (E/Z)-2-(2-(1-(pyridine-2-yl)ethylidene)hydrazinyl)quinolin-8-ol (0.350 g, 1.25 mmol) in ethanol (4 mL) was added to the reaction mixture. After that the mixture was stirred at room temperature for 4 days. The solvent was removed in vacuo. The residue was dissolved in dichloromethane and extracted with 10% NaOH solution (1×), than brine and after that water. The organic phase was dried over $Na_2SO_4$ and concentrated under reduced pressure. The residue was purified by flash chromatography on silica gel (ethyl acetate:methanol:ammonia=5:1:0.4) to give the titled compound (0.136 g, 29%) as brown crystals. Mp. 69-71° C. 1H NMR (300 MHz, CDCl$_3$): δ 1.64 (d, 5H), 2.43-2.60 (m, 8H), 3.82 (s, 2H), 6.92 (d, 1H), 7.12 (d, 1H), 7.19 (t, 1H), 7.69 (q, 2H), 7.99 (d, 1H), 8.18 (d, 1H), 8.56 (d, 1H). 13C NMR (75 MHz, CDCl$_3$): δ 23.9, 25.7, 53.9, 54.3, 62.0, 109.6, 117.3, 118.5, 119.9, 122.6, 123.7, 125.2, 135.9, 137.7, 138.0, 143.9, 148.4, 152.0, 154.6, 156.0. LCMS RT=2.61 min. ESI+ m/z: 376.3 [M+H+].

Example 4

(E/Z)-2-(2-(1-(2-Hydroxyphenyl)ethylidene)hydrazinyl)-7-(piperidin-1-ylmethyl)quinolin-8-ol

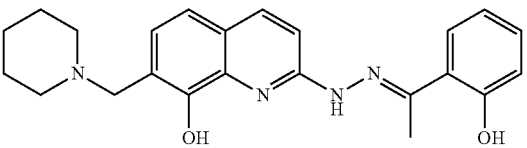 [SMILES: C/C(=N\Nc1ccc2ccc(CN3CCCCC3)c(O)c2n1)c1ccccc1O]

The solution of piperidine (111 μL, 0.096 g, 1.12 mmol) in ethanol (6 mL) was added 35% formaldehyde (137 μL, 0.05 g, 1.63 mmol). The mixture was stirred for 1 hour. Then the solution of (E/Z)-2-(2-(1-(2-hydroxyphenyl)ethylidene)hydrazinyl)quinolin-8-ol (0.3 g, 1.02 mmol) in ethanol (6 mL) was added to the reaction mixture. After that the mixture was stirred at room temperature for 4 days. The solvent was removed in vacuo. The residue was dissolved in dichloromethane and extracted with 10% NaOH solution (1×), than brine and after that water. The organic phase was dried over $Na_2SO_4$ and concentrated under reduced pressure. The residue was purified by flash chromatography on silica gel (eluent:ethyl acetate:methanol:ammonia=10:1:0,2) to give the titled compound (0.07 g, 17%) as yellow crystals. Mp. 184-187° C. 1H NMR (300 MHz, CDCl$_3$): δ 1.51 (d, 6H), 2.53 (s, 7H), 3.75 (s, 2H), 6.61 (t, 1H), 6.72 (d, 1H), 6.80-6.85 (m, 1H), 6.94 (t, 1H), 7.02 (t, 1H), 7.16-7.26 (m, 1H), 7.43 (dd, 1H), 7.87 (d, 1H). 13C NMR (75 MHz, CDCl$_3$): δ 13.9, 23.9, 25.8, 54.0, 61.9, 109.1, 117.0, 117.4, 118.5, 118.9, 120.0, 121.3, 127.1, 128.0, 130.2, 134.8, 138.6, 144.2, 150.2, 153.6, 158.1. LCMS RT=2.95 min. ESI+ m/z: 391.5 [M+H+].

Example 5

(E/Z)-7-(Piperidin-1-ylmethyl)-2-(2-(pyridine-2-ylmethylene)hydrazinyl)quinolin-8-ol

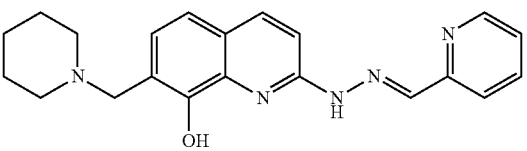 [SMILES: Oc1c(CN2CCCCC2)ccc2ccc(N/N=C/c3ccccn3)nc12]

The solution of piperidine (82 μL, 0.071 g, 0.832 mmol) in ethanol (4 mL) was added 35% formaldehyde (102 μL, 0.036 g, 1.21 mmol). The mixture was stirred for 1 hour. Then the solution of (E/Z)-2-(2-(pyridine-2-yl-methylene)hydrazinyl)quinolin-8-ol (0.2 g, 0.756 mmol) in ethanol (4 mL) was added to the reaction mixture. After that the mixture was stirred at room temperature for 3 days. The solvent was removed in vacuo. The residue was dissolved in dichloromethane and extracted with 10% NaOH solution (1×), than brine and after that water. The organic phase was dried over $Na_2SO_4$ and concentrated under reduced pressure. The residue was treated with ethanol to give the titled compound was (0.09 g, 33%) as orange crystals. Mp.

248-250° C. 1H NMR (300 MHz, DMSO-$d_6$): δ 1.46 (d, 6H), 2.48 (d, 4H), 3.73 (s, 2H), 7.02 (d, 1H), 7.17 (d, 1H), 7.29 (t, 1H), 7.57 (d, 1H), 7.80 (t, 1H), 7.98 (d, 1H), 8.11 (d, 2H), 8.52 (s, 1H), 11.70 (s, 1H), 14.92 (s, 1H). 13C NMR (75 MHz, DMSO-$d_6$): δ 23.6, 25.4, 53.3, 59.7, 109.1, 117.2, 119.2, 119.4, 123.0, 124.0, 124.1, 136.5, 137.1, 138.0, 139.6, 149.3, 150.7, 154.0, 154.1. LCMS RT=5.22 min. ESI+ m/z: 362.2 [M+H+].

Reaction scheme to some further compounds

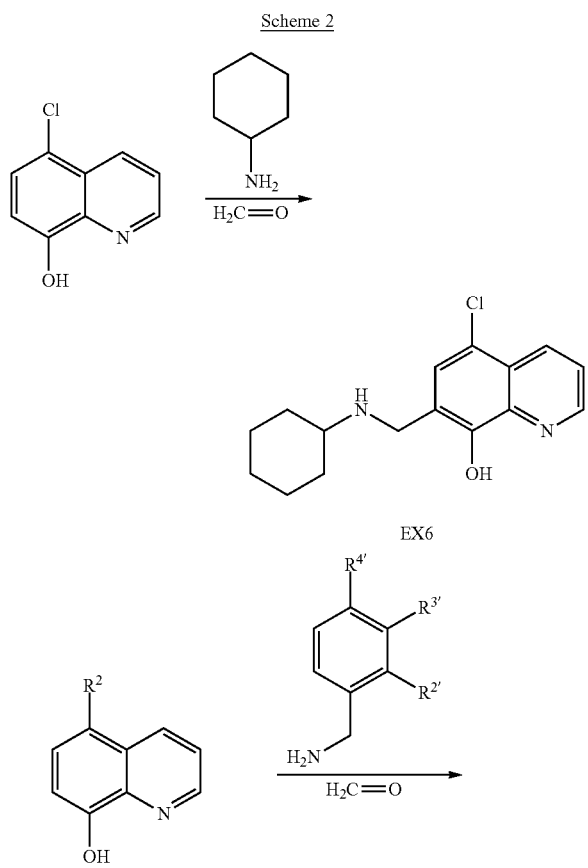

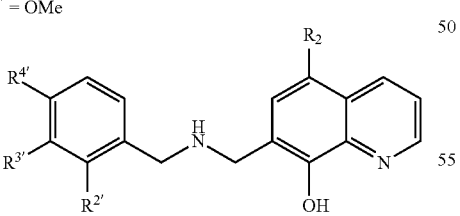

EX25 $R^2$ = Br; $R^{3'}$ = $R^{4'}$ = OMe
EX26 $R^2$ = Cl; $R^{2'}$ = $R^{4'}$ = OMe
EX27 $R^2$ = NO$_2$; $R^{4'}$ = OMe
EX28 $R^2$ = NO$_2$; $R^{2'}$ = $R^{4'}$ = OMe
EX29 $R^2$ = NO$_2$; $R^{2'}$ = OMe
EX30 $R^2$ = NO$_2$; $R^{3'}$ = $R^{4'}$ = OMe
EX37 $R^2$ = MeSO$_2$; $R^{2'}$ = $R^{4'}$ = OMe

Example 6

5-Chloro-7-((cyclohexylamino)methyl)quinolin-8-ol

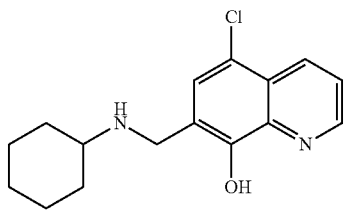 [SMILES: Oc1c(CNC2CCCCC2)cc(Cl)c2cccnc12]

The solution of cyclohexylamine (252 μL, 0.218 g, 2 mmol) θ in ethanol (4 mL) was added 35% formaldehyde (118 μL, 0.96 g, 3.2 mmol). The mixture was stirred for 1 hour. Then the solution of 5-chloroquinolin-8-ol (0.359 g, 2 mmol) in ethanol (4 mL) was added to the reaction mixture. After that the mixture was stirred at room temperature for 4 days. The solvent was removed in vacuo. The residue was dissolved in dichloromethane and extracted with 10% NaOH solution (1×), than brine and after that water. The organic phase was dried over Na$_2$SO$_4$ and concentrated under reduced pressure. The residue was treated with cold ethanol to give the titled compound (0.13 g, 22%) as yellow crystals. Mp. 123-125° C. 1H NMR (300 MHz, DMSO-$d_6$): δ 1.13 (s, 5H), 1.59 (d, 3H), 1.85 (s, 1H), 2.41 (s, 1H), 4.00 (s, 2H), 4.82 (br, 1H), 7.62 (s, 2H), 8.40 (s, 1H), 8.89 (s, 1H). 13C NMR (75 MHz, DMSO-$d_6$): δ 24.2, 25.6, 32.3, 45.6, 55.0, 117.3, 122.1, 127.5, 132.0, 139.0, 148.7, 151.9. LCMS RT=2.58 min. ESI+ m/z: 291.4 [M+H+].

Example 7

5-Chloro-7-(((4-methoxybenzyl)amino)methyl)quinolin-8-ol

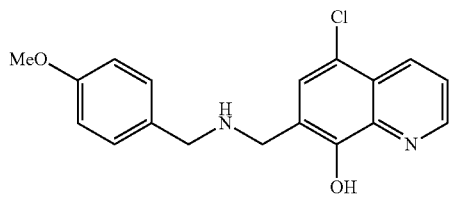

The solution of 4-methoxybenzylamine (282 μL, 0.302 g, 2.2 mmol) in ethanol (5 mL) was added 37% formaldehyde (83 μL, 0.066 g, 2.2 mmol). The mixture was stirred for 1 hour. Then the solution of 5-chloroquinolin-8-ol (0.359 g, 2 mmol) in ethanol (5 mL) was added to the reaction mixture. After that the mixture was stirred at room temperature for 14 days. The solvent was removed in vacuo. The residue was dissolved in dichloromethane and extracted with 10% NaOH solution (1x), than brine and after that water. The organic phase was dried over Na₂SO₄ and concentrated under reduced pressure. The residue was treated with cold ethanol to give the titled compound (0.113 g, 17%) as yellow crystals. Mp. 125-127° C. 1H NMR (300 MHz, CDCl₃): δ 3.80 (d, 5H), 4.11 (s, 2H), 6.88 (d, 2H), 7.27 (d, 2H), 7.43 (s, 1H), 7.46-7.52 (m, 1H), 8.45 (d, 1H), 8.86 (s, 1H). 13C NMR (75 MHz, CDCl₃): δ 49.3, 52.2, 55.2, 113.9, 119.9, 120.0, 121.9, 125.7, 127.7, 129.6, 130.6, 132.8, 139.3, 148.9, 151.3, 158.9. LCMS RT=4.48 min. ESI+ m/z: 329.1 [M+H+].

Example 8

5-Bromo-7-(((2-methoxybenzyl)amino)methyl)quinolin-8-ol

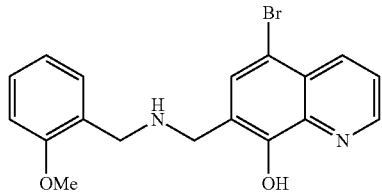 [SMILES: COc1ccccc1CNCc1cc(Br)c2cccnc2c1O]

The solution of 2-methoxybenzylamine (211 μL, 0.226 g, 1.65 mmol) in ethanol (4 mL) was added 37% formaldehyde (62 μL, 0.049 g, 1.65 mmol). The mixture was stirred for 1 hour. Then the solution of 5-bromoquinolin-8-ol (0.336 g, 1.5 mmol) in ethanol (5 mL) was added to the reaction mixture. After that the mixture was refluxed at 50° C. for 56 hours. The reaction mixture was allowed to cool down and the obtained precipitate was filtered off, washed with ethanol and crystallized from ethanol to give the titled compound (0.130 g, 23%) as yellow crystals. Mp. 135-137° C. 1H NMR (300 MHz, CDCl₃): δ 3.83 (s, 3H), 3.93 (s, 2H), 4.11 (s, 2H), 6.84-6.94 (m, 2H), 7.21-7.29 (m, 2H), 7.46-7.51 (m, 1H), 7.60 (s, 1H), 8.40 (d, 1H), 8.84 (d, 1H). 13C NMR (75 MHz, CDCl₃): δ 48.2, 49.3, 55.2, 109.2, 110.0, 110.2, 120.5, 122.2, 125.9, 127.1, 129.0, 130.5, 131.0, 135.3, 139.8, 149.0, 152.8, 157.7. LCMS RT=4.08 min. ESI+ m/z: 375.4 [M+H+].

Example 9

5-Bromo-7-(((2,4-dimethoxybenzyl)amino)methyl)quinolin-8-ol

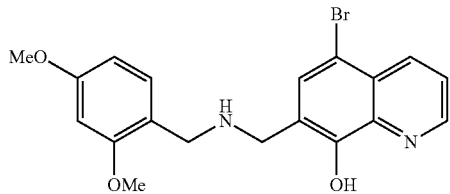 [SMILES: COc1ccc(CNCc2cc(Br)c3cccnc3c2O)c(OC)c1]

The solution of 2,4-dimethoxybenzylamine (248 μL, 0.276 g, 1.65 mmol) in ethanol (4 mL) was added 37% formaldehyde (62 μL, 0.049 g, 1.65 mmol). The mixture was stirred for 1 hour. Then the solution of 5-bromoquinolin-8-ol (0.336 g, 1.5 mmol) in ethanol (5 mL) was added to the reaction mixture. After that the mixture was refluxed at 50° C. for 56 hours. The reaction mixture was allowed to cool down and the obtained precipitate was filtered off, washed with ethanol and crystallized from ethanol to give the titled compound (0.170 g, 28%) as yellow crystals. Mp. 146-148° C. 1H NMR (300 MHz, CDCl₃): δ 3.80-3.82 (d, 8H), 4.07 (s, 2H), 6.44 (d, 2H), 7.08 (d, 1H), 7.46-7.51 (m, 1H), 7.62 (s, 1H), 8.46 (d, 1H), 8.89 (s, 1H). 13C NMR (75 MHz, CDCl₃): δ 47.7, 49.5, 55.2, 55.3, 98.6, 103.7, 109.1, 118.8, 120.6, 122.1, 127.0, 130.9, 131.0, 135.2, 140.0, 149.0, 153.1, 158.7, 160.5. LCMS RT=4.12 min. ESI+ m/z: 403.5 [M+H+].

Example 10

5-Bromo-7-(((4-methoxybenzyl)amino)methyl)quinolin-8-ol

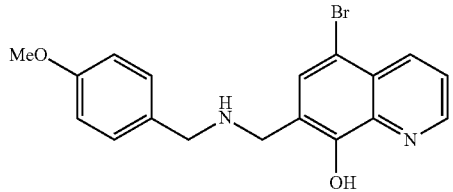 [SMILES: COc1ccc(CNCc2cc(Br)c3cccnc3c2O)cc1]

The solution of 4-methoxybenzylamine (211 μL, 0.226 g, 1.65 mmol) in ethanol (4 mL) was added 37% formaldehyde (62 μL, 0.049 g, 1.65 mmol). The mixture was stirred for 1 hour. Then the solution of 5-bromoquinolin-8-ol (0.336 g, 1.5 mmol) in ethanol (5 mL) was added to the reaction mixture. After that the mixture was refluxed at 50° C. for 72 hours. The reaction mixture was allowed to cool down and the obtained precipitate was filtered off, washed with ethanol and crystallized from ethanol to give the titled compound (0.150 g, 27%) as yellow crystals. Mp. 129-132° C. 1H NMR (300 MHz, CDCl₃): δ 3.81 (d, 5H), 4.12 (s, 2H), 6.87 (d, 2H), 7.28 (d, 2H), 7.46-7.51 (m, 1H), 7.62 (s, 1H), 8.40 (d, 1H), 8.83 (d, 1H). 13C NMR (75 MHz, CDCl₃): δ 49.4, 52.3, 55.2, 109.4, 113.9, 120.9, 122.3, 127.0, 129.6, 131.2, 134.9, 135.3, 139.6, 149.0, 152.0, 158.9. LCMS RT=4.19 min. ESI+ m/z: 375.6 [M+H+].

Reaction schemes to some further compounds

Scheme 3

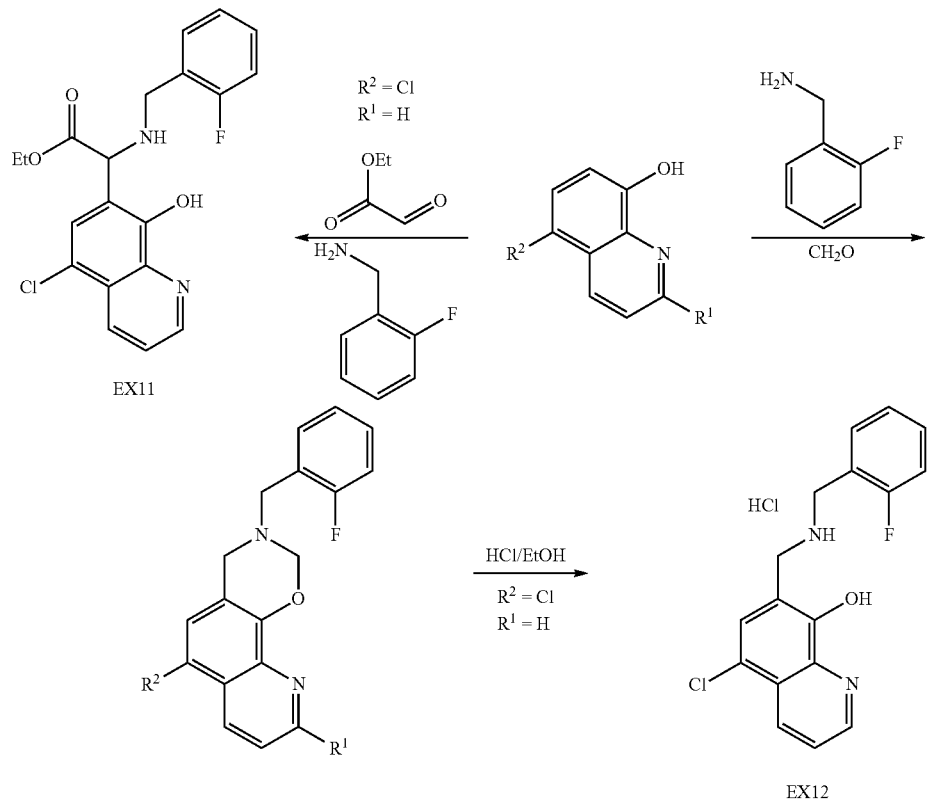

Example 11

Ethyl 2-(5-chloro-8-hydroxyquinolin-7-yl)-2-{[(2-fluorophenyl)methyl]amino}acetate

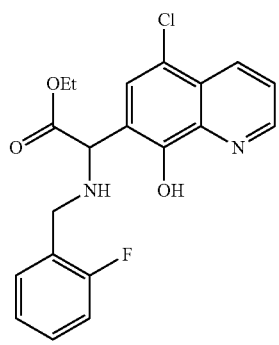 [SMILES: CCOC(=O)C(NCc1ccccc1F)c1cc(Cl)c2cccnc2c1O]

In a 35 mL pressurized reaction vial, 2-fluorobenzylamine (0.40 g, 3.2 mmol), 5-chloro-8-hydroxyquinoline (0.45 g, 2.5 mmol) and ethyl glyoxylate (50% in toluene) (1.02 g, 5.0 mmol) were dissolved in ethanol (20 mL). The reaction mixture was heated in a CEM Discover SP MW reactor at 110° C. for 120 min. The solvent was evaporated and water (20 mL) was added to the residue and extracted with dichloromethane (3×15 mL). The combined organic extracts were dried over $Na_2SO_4$ and concentrated under reduced pressure. The residue was crystallized from n-hexane:ethyl acetate (8 mL:1 mL) to give the titled compound (0.74 g, 76%). M.p. 204-206° C. 1H NMR (300 MHz, DMSO-$d_6$): δ 1.16 (t, J=7.2 Hz, 3H), 4.24 (q, J=8.1 Hz, 2H) 4.27 (s, 2H), 5.67 (s, 1H), 7.13 (d, J=8.4 Hz, 1H), 7.21-7.28 (m, 2H), 7.45 (t, J=7.4 Hz, 1H), 7.74-7.80 (m, 2H), 8.98 (s, 1H), 9.05 (d, J=7.2 Hz, 1H).

Example 12

5-Chloro-7-({[(2-fluorophenyl)methyl]amino}methyl)quinolin-8-ol Hydrochloride

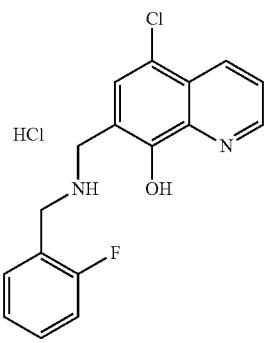 [SMILES: Oc1c(CNCc2ccccc2F)cc(Cl)c2cccnc12 ; Cl]

To a stirred solution of compound 7a (0.20 g; 0.6 mmol) in ethanol (15 mL), (0.15 mL, 1.0 mmol) of HCl/EtOH (22%) was added. The mixture was stirred for 1 h at room temperature. The solvent was evaporated and the residue crystallized with Et$_2$O (10 mL) to give the titled compound (0.19 g, 91%). M.p. 211-213° C. 1H NMR (300 MHz, DMSO-d$_6$): δ 4.29 (s, 2H), 4.39 (s, 2H), 7.25-7.34 (m, 2H), 7.49 (d, J=7.3 Hz, 1H), 7.70 (t, J=7.2 Hz, 1H), 7.78-7.95 (m, 1H) 8.55 (d, J=8.2 Hz, 1H), 9.03 (s, 1H), 9.58 (brs, 2H).

Reaction Scheme to Some Further Compounds

Example 13

5-Chloro-7-(1,2,3,4-tetrahydroisoquinolin-1-yl)quinolin-8-ol

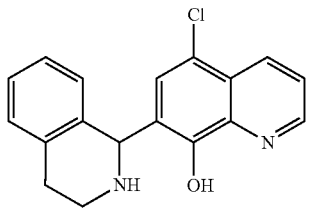

Scheme 4

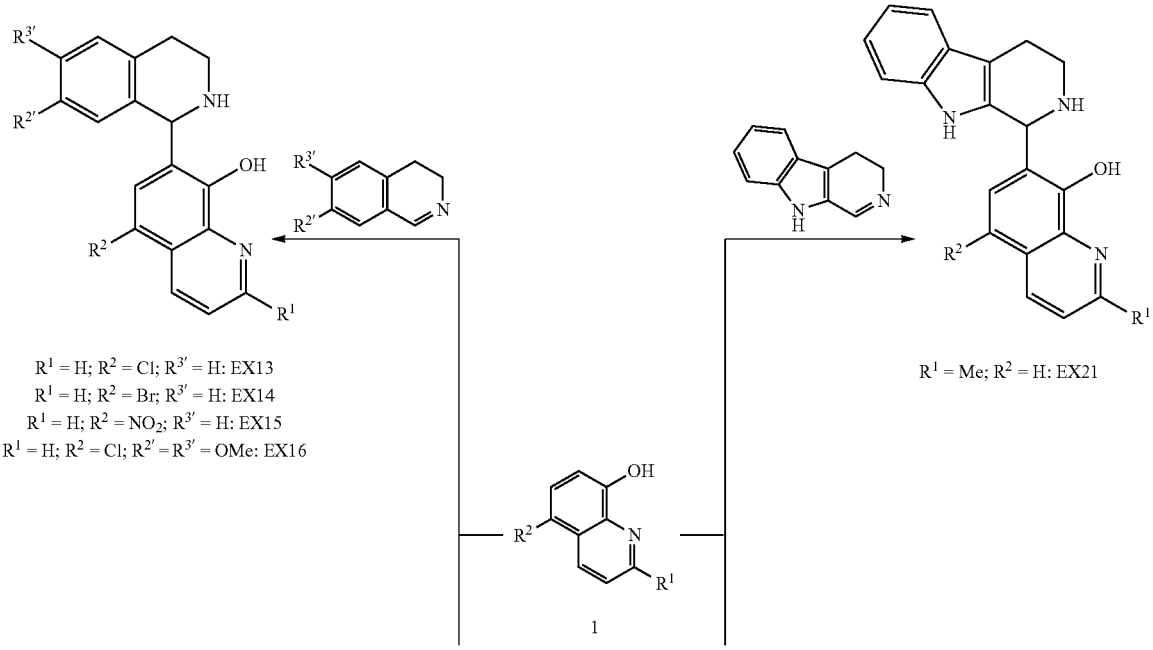

R$^1$ = H; R$^2$ = Cl; R$^{3'}$ = H: EX13
R$^1$ = H; R$^2$ = Br; R$^{3'}$ = H: EX14
R$^1$ = H; R$^2$ = NO$_2$; R$^{3'}$ = H: EX15
R$^1$ = H; R$^2$ = Cl; R$^{2'}$ = R$^{3'}$ = OMe: EX16

R$^1$ = Me; R$^2$ = H: EX21

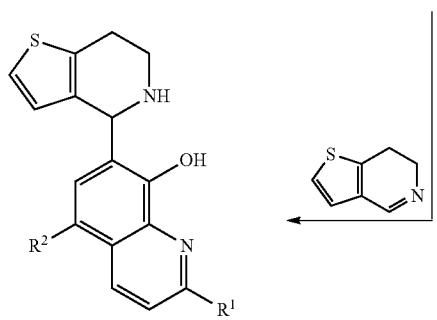

R$^1$ = H; R$^2$ = Cl: EX17  R$^1$ = H; R$^2$ = H: EX18
R$^1$ = H; R$^2$ = NO$_2$: EX19  R$^1$ = Me  R$^2$ = H: EX20

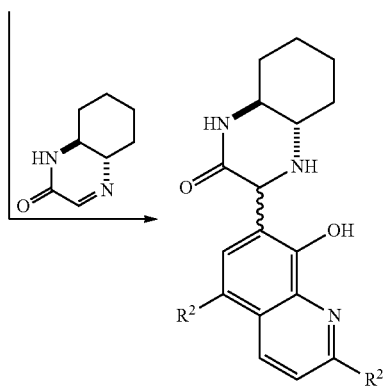

R$^1$ = H; R$^2$ = Cl: EX22
R$^1$ = H; R$^2$ = H: EX23

In a 10 mL round bottomed flask equivalent amount of 5-chloroquinolin-8-ol (0.23 g; 1.26 mmol) and 3,4-dihydroisoquinoline (0.165 g; 1.26 mmol) were added. The reaction mixture was heated in oil bath for 12 h at 80° C. The products were then isolated by crystallization with methanol (10 mL) to give the titled compound (0.27 g, 71%). M.p. 173-175° C. 1H NMR (300 MHz, DMSO-$d_6$): δ 2.74-2.82 (m, 1H), 2.95-3.07 (m, 2H), 3.17-3.25 (m, 1H), 5.59 (s, 1H), 6.76 (d, J=7.2 Hz, 1H), 7.02 (t, J=6.5 Hz, 1H), 7.11-7.21 (m, 2H), 7.45 (s, 1H), 7.68-7.73 (m, 1H), 8.47 (d, J=8.2 Hz, 1H), 8.96 (s, 1H).

Example 14

5-Bromo-7-(1,2,3,4-tetrahydroisoquinolin-1-yl)quinolin-8-ol

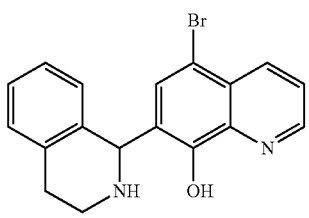 [SMILES: Oc1c(C2NCCc3ccccc32)cc(Cl)c2cccnc12]

Prepared according to Example 13, from 5-bromoquinolin-8-ol (0.282 g, 1.26 mmol) and 3,4-dihydroisoquinoline (0.165 g, 1.26 mmol) to give the titled compound (0.37 g, 82%). M.p. 179-181° C. 1H NMR (300 MHz, DMSO-$d_6$): δ 2.73-2.83 (m, 1H), 2.96-3.07 (m, 2H), 3.15-3.27 (m, 1H), 5.60 (s, 1H), 6.75 (d, J=7.3 Hz, 1H), 7.03 (t, J=6.4 Hz, 1H), 7.10-7.20 (m, 2H), 7.63 (s, 1H), 7.67-7.74 (m, 1H), 8.40 (d, J=8.1 Hz, 1H), 8.94 (s, 1H).

Example 15

5-Nitro-7-(1,2,3,4-tetrahydroisoquinolin-1-yl)quinolin-8-ol

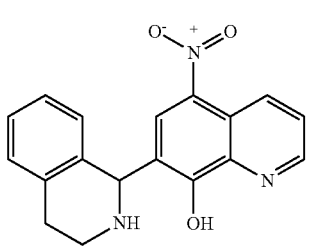

Prepared according to Example 13, from 5-nitroquinolin-8-ol (0.24 g, 1.26 mmol) and 3,4-dihydroisoquinoline (0.165 g, 1.26 mmol) to give the titled compound (0.30 g, 75%). M.p. 253-255° C. 1H NMR (300 MHz, DMSO-$d_6$): δ 2.98-3.11 (m, 1H), 3.14-3.22 (m, 1H), 3.33-3.44 (m, 2H), 5.83 (s, 1H), 7.00 (d, J=7.1 Hz, 1H), 7.16-7.34 (m, 3H), 7.51-7.58 (m, 1H), 8.16 (s, 1H), 8.57-8.64 (m, 1H), 9.31 (d, J=8.4 Hz, 1H).

Example 16

5-Chloro-7-(6,7-dimethoxy-1,2,3,4-tetrahydroisoquinolin-1-yl)quinolin-8-ol

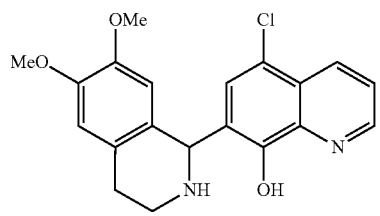 [SMILES: COc1cc2c(cc1OC)C(c1cc(Cl)c3cccnc3c1O)NCC2]

Prepared according to Example 13, from 5-chloroquinolin-8-ol (0.22 g, 1.26 mmol) and 6-7-dimethoxy-3,4-dihydroisoquinoline (0.24 g, 1.26 mmol) to give the titled compound (0.37 g, 79%). M.p. 189-192° C. 1H NMR (300 MHz, DMSO-$d_6$): δ 2.74-2.82 (m, 1H), 2.96-3.07 (m, 2H), 3.18-3.27 (m, 1H), 3.49 (s, 3H), 3.77 (s, 3H), 5.70 (s, 1H), 6.38 (s, 1H), 6.82 (s, 1H), 7.33 (s, 1H), 7.70-7.78 (m, 1H), 8.49 (d, J=8.2 Hz, 1H), 8.99 (s, 1H).

Example 17

5-Chloro-7-(4,5,6,7-tetrahydrothieno[3,2-c]pyridin-4-yl)quinolin-8-ol

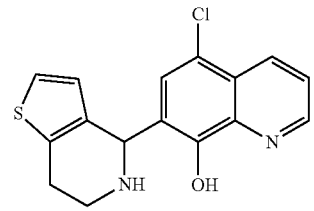 [SMILES: Oc1c(C2NCCc3sccc32)cc(Cl)c2cccnc12]

Prepared according to Example 13, from 5-chloroquinolin-8-ol (0.22 g, 1.26 mmol) and 6,7-dihydrothieno[3,2-c]pyridine (0.17 g 1.26 mmol) to give the titled compound (0.31 g, 77%). M.p. 198-201° C. 1H NMR (300 MHz, DMSO-$d_6$): δ 2.76-2.86 (m 1H), 2.91-3.06 (m 2H), 3.20-3.31 (m, 1H), 5.51 (s, 1H), 6.49 (d, J=7.2 Hz, 1H), 7.19 (d, J=7.5 Hz, 1H), 7.51 (s, 1H), 7.68-7.72 (m, 1H), 8.46 (d, J=8.5 Hz, 1H), 8.95 (s, 1H).

Example 18

7-(4,5,6,7-Tetrahydrothieno[3,2-c]pyridin-4-yl)quinolin-8-ol

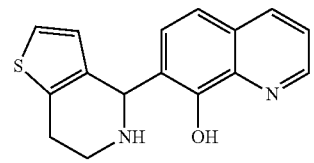 [SMILES: Oc1c(C2NCCc3sccc32)ccc2cccnc12]

Prepared according to Example 13, from 8-quinolinol (0.18 g, 1.26 mmol) and 6,7-dihydrothieno[3,2-c]pyridine (0.17 g, 1.26 mmol) to give the titled compound (0.26 g, 72%). M.p. 181-183° C. 1H NMR (300 MHz, DMSO-d$_6$): δ 2.75-2.85 (m, 1H), 2.92-3.05 (m, 2H), 3.22-3.35 (m, 1H), 5.48 (s, 1H), 6.44 (d, J=7.1 Hz, 1H), 7.16 (d, J=7.4 Hz, 1H), 7.30-7.49 (m, 2H), 7.49-7.54 (m, 1H), 8.27 (d, J=8.4 Hz, 1H), 8.84 (s, 1H).

Example 19

5-Nitro-7-(4,5,6,7-tetrahydrothieno[3,2-c]pyridin-4-yl)quinolin-8-ol

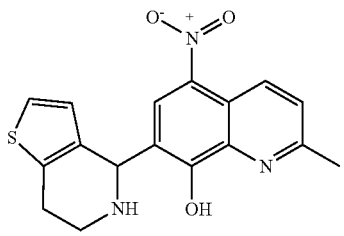

Prepared according to Example 13, from 5-nitroquinolin-8-ol (0.24 g, 1.26 mmol) and 6,7-dihydrothieno[3,2-c]pyridine (0.17 g, 1.26 mmol) to give the titled compound (0.33 g, 80%). M.p. 219-222° C. 1H NMR (300 MHz, DMSO-d$_6$): δ 2.75-2.85 (m, 1H), 2.90-3.02 (m, 2H), 3.25-3.33 (m, 1H), 5.85 (s, 1H), 6.75 (d, J=5.2 Hz, 1H), 7.49 (d, J=5.2 Hz, 1H), 7.55-7.61 (m, 1H), 8.15 (s, 1H), 8.64 (s, 1H), 9.35 (d, J=8.4 Hz, 1H).

Example 20

2-(2-Methyl-7-{4,5,6,7-tetrahydrothieno[3,2-c]pyridin-4-yl}quinolin-8-ol

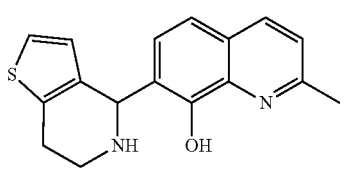 [SMILES: Cc1ccc2ccc(C3NCCc4sccc43)c(O)c2n1]

Prepared according to Example 13, from 8-hydroxy-2-methylquinoline (0.20 g, 1.26 mmol) and 6,7-dihydrothieno[3,2-c]pyridine (0.17 g, 1.26 mmol) to give the titled compound (0.28 g, 75%). M.p. 172-176° C. 1H NMR (300 MHz, DMSO-d$_6$): δ 2.57 (s, 3H), 2.67-2.76 (m, 1H), 2.78-2.95 (m, 2H), 3.04-3.11 (m, 1H), 5.36 (s, 1H), 6.33 (d, J=7.2 Hz, 1H), 7.05 (d, J=6.2 Hz, 1H), 7.10-7.14 (m, 2H), 7.28 (d, J=8.2 Hz, 1H), 8.05 (d, J=8.2 Hz, 1H), 8.15 (s, 1H), 8.64 (s, 1H), 9.35 (d, J=8.4 Hz, 1H).

Example 21

2-Methyl-7-{1H,2H,3H,4H,9H-pyrido[3,4-b]indol-1-yl}quinolin-8-ol

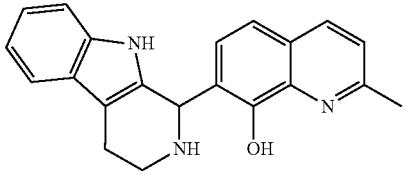 [SMILES: Cc1ccc2ccc(C3NCCc4c3[nH]c3ccccc43)c(O)c2n1]

Prepared according to Example 13, from 2-methylquinolin-8-ol (0.20 g, 1.26 mmol) and 4,9-dihydro-3H-pyrido[3,4-b]indole (0.21 g, 1.26 mmol) to give the titled compound (0.32 g, 78%). M.p. 136-139° C. 1H NMR (300 MHz, DMSO-d$_6$): δ 2.67 (s, 3H), 2.69-2.85 (m, 1H), 2.98-3.08 (m, 1H), 3.14-3.25 (m, 2H), 5.65 (s, 1H), 6.89-7.01 (m, 2H), 7.15 (d, J=8.6 Hz, 1H), 7.20 (d, J=7.9 Hz, 1H), 7.26 (d, J=8.4 Hz, 1H), 7.40 (t, J=7.6 Hz, 2H), 8.15 (d, J=8.4 Hz, 1H) 10.34 (brs, 1H).

Example 22

(3R,4aS,8aS)-3-(5-Chloro-8-hydroxyquinolin-7-yl)octahydroquinoxalin-2(1H)-one and (3S,4aS,8aS)-3-(5-chloro-8-hydroxyquinolin-7-yl)octahydroquinoxalin-2(1H)-one

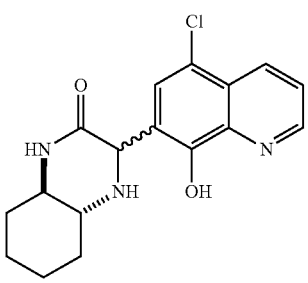

Prepared according to Example 13, from 5-chloroquinolin-8-ol (0.22 g, 1.26 mmol) and (4aS,8aS)-4a,5,6,7,8,8a-hexahydroquinoxalin-2(1H)-one (0.19 g, 1.26 mmol) to give the mixture of diastereomers D1:D2:1:0.5 (0.29 g, 71%). 1H NMR (300 MHz, DMSO-d$_6$); D1: δ 1.05-1.38 (m, 4H), 1.56-1.89 (m, 4H), 2.47-2.60 (m, 1H), 3.05-3.16 (m, 1H), 4.90 (s, H), 7.56 (s, 1H), 7.63-7.71 (m, 1H), 7.88 (s, 1H), 8.40-8.47 (m, 1H), 8.87-8.94 (m, 1H); D2: δ 1.07-1.35 (m, 4H), 1.60-1.91 (m, 4H), 2.34-2.41 (m, 1H), 2.96-3.05 (m, 1H), 4.95 (s, 1H), 7.43 (s, 1H), 7.63-7.71 (m, 1H), 8.18 (s, 1H), 8.40-8.47 (m, 1H), 8.87-8.94 (m, 1H).

Example 23

(3R,4aS,8aS)-3-(8-Hydroxyquinolin-7-yl)octahydroquinoxalin-2(1H)-one and (3S,4aS,8aS)-3-(8-hydroxyquinolin-7-yl)octahydroquinoxalin-2(1H)-one

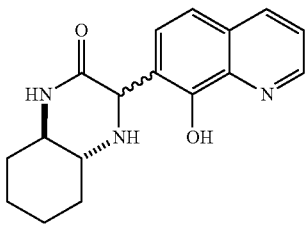

Prepared according to Example 13, from 8-quinolinol (0.18 g, 1.26 mmol) and (4aS,8aS)-4a,5,6,7,8,8a-hexahydroquinoxalin-2(1H)-one (0.19 g, 1.26 mmol) to give the mixture of diastereomers D1:D2:1:0.4 (0.28 g, 77%). 1H NMR (300 MHz, DMSO-$d_6$): D1: δ 1.07-1.39 (m, 4H), 1.58-1.91 (m, 4H), 2.45-2.63 (m, 1H), 3.08-3.18 (m, 1H), 4.86 (s, 1H), 7.32 (s, 1H), 7.46-7.53 (m, 2H), 7.80-7.84 (m, 1H), 8.26 (d, J=8.3 Hz, 1H), 8.81 (t, J=4.3 Hz, 1H); D2: δ 1.03-1.31 (m, 4H), 1.53-1.87 (m, 4H), 2.35-2.43 (m, 1H), 2.95-3.00 (m, 1H), 4.93 (s, 1H), 7.29-7.33 (m, 1H), 7.38-7.44 (m, 1H), 8.25-8.31 (m, 1H), 8.75-8.83 (m, 2H).

Reaction Scheme to a Further Compound

Scheme 5

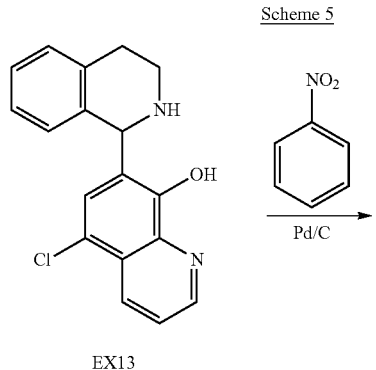

EX13

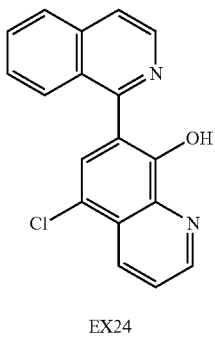

EX24

Example 24

5-Chloro-7-(isoquinolin-1-yl)quinolin-8-ol

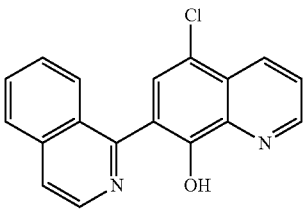 [SMILES: Oc1c(-c2nccc3ccccc23)cc(Cl)c2cccnc12]

In a 25 mL round bottomed flask 5-chloro-7-(1,2,3,4-tetrahydroisoquinolin-1-yl)quinolin-8-ol (5a, 0.20 g, 0.64 mmol) was dissolved in nitrobenzene (20 mL). 300 mg of Pd/C were added to the mixture and was refluxed for 4 h. The solvent was removed to the half under reduced pressure and the residue was crystallized with diethylether (25 mL) to give the titled compound (0.13 g, 68%). M.p. 165-169° C. 1H NMR (300 MHz, DMSO-$d_6$): δ 7.60 (t, J=7.1 Hz, 1H), 7.70-7.98 (m, 5H), 8.07 (d, J=8.2 Hz, 1H), 8.59-8.70 (m, 2H), 9.06 (s, 1H), 10.38 (brs, 1H).

Example 25

5-Bromo-7-(((3,4-dimethoxybenzyl)amino)methyl)quinolin-8-ol

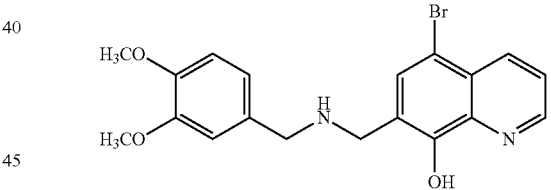

The solution of 3,4-dimethoxybenzylamine (248 µL, 0.276 g, 1.65 mmol) in ethanol (4 mL) was added 37% formaldehyde (62 µL, 0.049 g, 1.65 mmol). The mixture was stirred for 1 hour. Then the solution of 5-bromoquinolin-8-ol (0.336 g, 1.5 mmol) in ethanol (5 mL) was added to the reaction mixture. After that the mixture was refluxed at 50° C. for 72 hours. The reaction mixture was allowed to cool down and the obtained precipitate was filtered off, washed with ethanol and crystallized from ethanol to give the titled compound (0.130 g, 21%) as green crystals. Mp. 133-136° C. 1H NMR (300 MHz, CDCl$_3$): δ 3.87 (d, 8H), 4.11 (s, 2H), 6.80-6.91 (m, 3H), 7.50-7.52 (m, 1H), 7.65 (s, 1H), 8.41 (d, 1H), 8.82 (s, 1H). 13C NMR (75 MHz, CDCl$_3$): δ 52.0, 55.8, 55.9, 109.2, 110.9, 111.7, 119.5, 120.9, 121.0, 122.4, 127.1, 129.6, 131.5, 135.4, 139.3, 148.4, 148.9, 152.0, 152.1. LCMS RT=3.91 min. ESI+ m/z: 403.5 [M+H+].

Example 26

5-Chloro-7-(((2,4-dimethoxybenzyl)amino)methyl)quinolin-8-ol

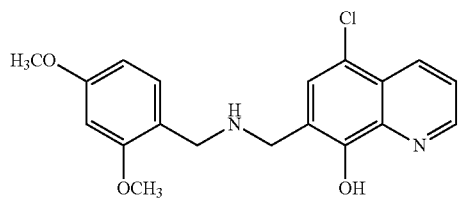 [SMILES: COc1ccc(CNCc2cc(Cl)c3cccnc3c2O)c(OC)c1]

The solution of 2,4-dimethoxybenzylamine (331 μL, 0.368 g, 2.2 mmol) in ethanol (5 mL) was added 37% formaldehyde (103 μL, 0.082 g, 2.8 mmol). The mixture was stirred for 1 hour. Then the solution of 5-chloroquinolin-8-ol (0.359 g, 2 mmol) in ethanol (5 mL) was added to the reaction mixture. After that the mixture was refluxed at 50° C. for 120 hours. The reaction mixture was allowed to cool down and the obtained precipitate was filtered off, washed with ethanol and crystallized from ethanol to give the titled compound (0.2 g, 28%) as green crystals. Mp. 136-139° C. 1H NMR (300 MHz, CDCl$_3$): δ 3.81 (d, 8H), 4.07 (s, 2H), 6.41-6.46 (m, 2H), 7.08 (d, 1H), 7.34 (s, 1H), 7.46-7.51 (m, 1H), 8.46 (d, 1H), 8.89 (s, 1H). 13C NMR (75 MHz, CDCl$_3$): δ 48.7, 55.2, 55.3, 98.4, 103.7, 117.3, 118.5, 119.5, 121.9, 125.9, 127.6, 131.3, 132.7, 139.4, 148.9, 152.2, 158.7, 160.8. LCMS RT=4.71 min. ESI+ m/z: 359.1 [M+H+].

Example 27

7-(((4-Methoxybenzyl)amino)methyl)-5-nitroquinolin-8-ol

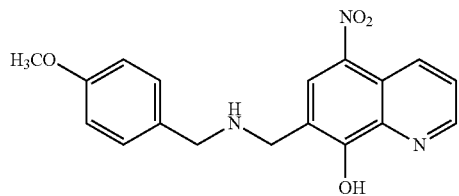 [SMILES: COc1ccc(CNCc2cc([N+](=O)[O-])c3cccnc3c2O)cc1]

The solution of 4-methoxybenzylamine (282 μL, 0.301 g, 2.2 mmol) in pyridine (10 mL) was added 37% formaldehyde (81 μL, 0.066 g, 2.2 mmol) and 5-nitroquinolin-8-ol (0.380 g, 2.0 mmol). After that the mixture was refluxed at 50° C. for 120 hours. The reaction mixture was allowed to cool down and the obtained precipitate was filtered off, washed with ethanol and crystallized from ethanol to give the titled compound (0.108 g, 16%) as yellow crystals. Mp. 191-193° C. 1H NMR (500 MHz, DMSO-d$_6$+TFA): δ 3.76 (s, 3H), 4.21 (s, 2H), 4.36 (s, 2H), 6.98 (d, 2H), 7.45 (d, 2H), 7.97-7.99 (m, 1H), 8.79 (s, 1H), 9.03 (s, 1H), 9.30 (d, 1H). 13C NMR (125 MHz, DMSO-d$_6$+TFA): δ 44.3, 55.1, 113.9, 114.6, 116.8, 122.4, 125.9, 131.3, 131.6, 132.4, 135.6, 136.0, 147.8, 157.8, 159.76, 161.0. LCMS RT=4.29 min. ESI+ m/z: 340.4 [M+H+].

Example 28

7-(((2,4-Dimethoxybenzyl)amino)methyl)-5-nitroquinolin-8-ol

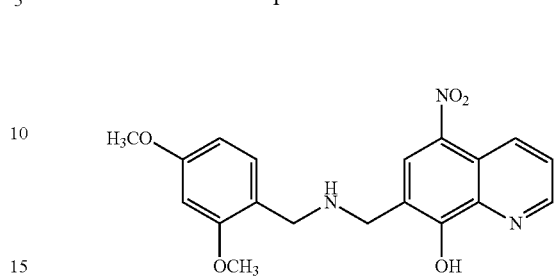

The solution of 2,4-dimethoxybenzylamine (331 μL, 0.368 g, 2.2 mmol) in pyridine (10 mL) was added 37% formaldehyde (82 μL, 0.066 g, 2.2 mmol) and 5-nitroquinolin-8-ol (0.380 g, 2.0 mmol). After that the mixture was refluxed at 50° C. for 72 hours. The reaction mixture was allowed to cool down and the obtained precipitate was filtered off, washed with ethanol and crystallized from ethanol to give the titled compound (0.285 g, 38%) as yellow crystals. Mp. 206-209° C. 1H NMR (500 MHz, DMSO-d$_6$+TFA): δ 3.75 (s, 3H), 3.79 (s, 3H), 4.12 (s, 2H), 4.34 (s, 2H), 6.52 (d, 1H), 6.57 (s, 1H), 7.31 (d, 1H), 7.96-7.99 (m, 1H), 8.75 (s, 1H), 9.02 (s, 1H), 9.31 (d, 1H). 13C NMR (125 MHz, DMSO-d$_6$+TFA): δ 44.2, 44.6, 55.3, 55.6, 98.2, 104.8, 116.9, 123.1, 125.8, 131.3, 131.4, 131.8, 132.4, 134.2, 135.8, 147.4, 158.7, 161.6. LCMS RT=4.31 min. ESI+ m/z: 370.4 [M+H+].

Example 29

7-(((2-Methoxybenzyl)amino)methyl)-5-nitroquinolin-8-ol

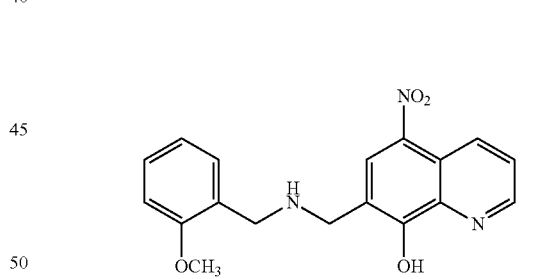

The solution of 2-methoxybenzylamine (282 μL, 0.301 g, 2.2 mmol) in pyridine (10 mL) was added 37% formaldehyde (81 μL, 0.066 g, 2.2 mmol) and 5-nitroquinolin-8-ol (0.380 g, 2.0 mmol). After that the mixture was refluxed at 50° C. for 24 hours. The reaction mixture was allowed to cool down and the obtained precipitate was filtered off, washed with ethanol and crystallized from ethanol to give the titled compound (0.160 g, 23%) as yellow crystals. Mp. 199-203° C. 1H NMR (500 MHz, DMSO-d$_6$+TFA): δ 3.81 (s, 3H), 4.20 (s, 2H), 4.39 (s, 2H), 6.96 (t, 1H), 7.04 (d, 1H), 7.37-7.42 (m, 2H), 7.97-7.99 (m, 1H), 8.77 (s, 1H), 9.03 (s, 1H), 9.31 (d, 1H). 13C NMR (125 MHz, DMSO-d$_6$+TFA): δ 44.2, 45.3, 55.5, 110.9, 114.4, 116.6, 120.3, 122.5, 125.8, 130.9, 131.4, 132.1, 134.4, 136.0, 147.4, 157.5, 161.0. LCMS RT=4.69 min. ESI+ m/z: 340.4 [M+H+].

Example 30

7-(((3,4-Dimethoxybenzyl)amino)methyl)-5-nitro-quinolin-8-ol

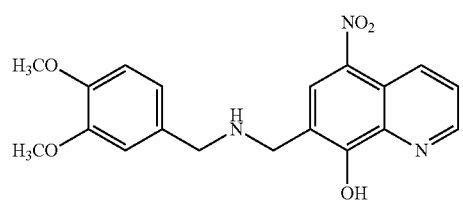 [SMILES: COc1ccc(CNCc2cc([N+](=O)[O-])c3cccnc3c2O)cc1OC]

The solution of 3,4-dimethoxybenzylamine (331 μL, 0.368 g, 2.2 mmol) in pyridine (10 mL) was added 37% formaldehyde (82 μL, 0.066 g, 2.2 mmol) and 5-nitroquinolin-8-ol (0.380 g, 2.0 mmol). After that the mixture was refluxed at 50° C. for 72 hours. The reaction mixture was allowed to cool down and the obtained precipitate was filtered off, washed with ethanol and crystallized from ethanol to give the titled compound (0.240 g, 32%) as yellow crystals. Mp. 204-206° C. 1H NMR (500 MHz, DMSO-$d_6$+ TFA): δ 3.75 (s, 6H), 4.20 (s, 2H), 4.36 (s, 2H), 6.96 (t, 1H), 7.04 (d, 1H), 7.15 (s, 1H), 7.96-7.99 (m, 1H), 8.74 (s, 1H), 9.03 (s, 1H), 9.30 (d, 1H). 13C NMR (125 MHz, DMSO-$d_6$+TFA): δ 43.8, 45.3, 55.9, 56.0, 112.0, 113.9, 115.0, 117.3, 123.2, 126.2, 131.8, 132.7, 134.7, 136.5, 148.3, 149.1, 149.8, 161.4. LCMS RT=4.19 min. ESI+ m/z: 370.5 [M+H+].

Reaction Scheme to Some Further Compounds

Scheme 6

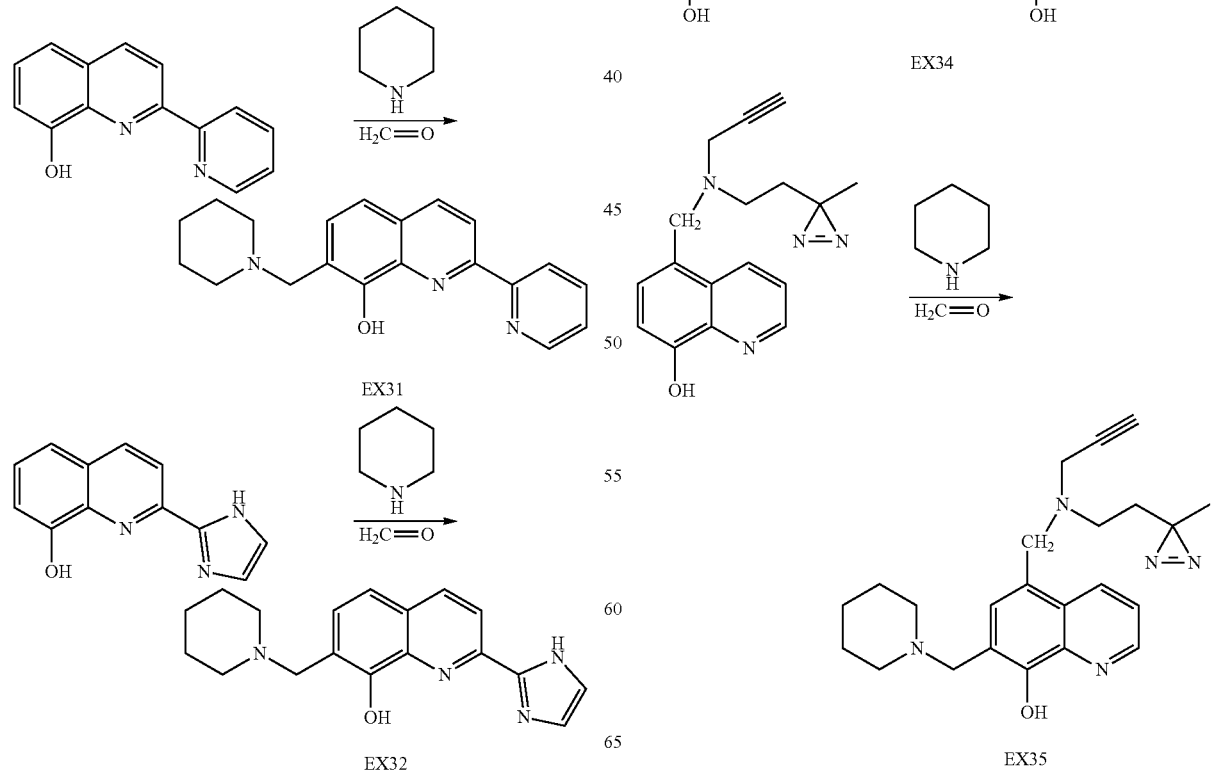

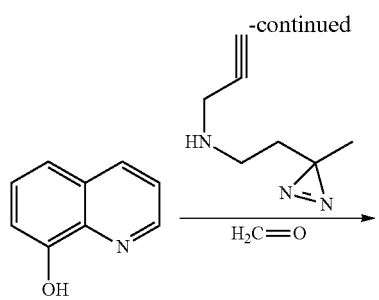

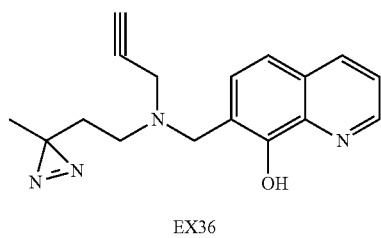

EX36

Example 31

7-(Piperidin-1-ylmethyl)-2-(pyridin-2-yl)quinolin-8-ol

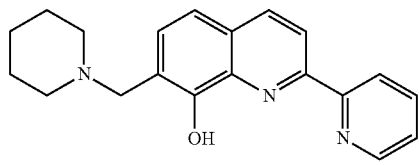 [SMILES: Oc1c(CN2CCCCC2)ccc2ccc(-c3ccccn3)nc12]

The solution of piperidine (25 μL, 0.021 g, 0.247 mmol) in ethanol (1 mL) was added 35% formaldehyde (27 μL, 0.009 g 0.315 mmol). The mixture was stirred for 1 hour. Then the solution of 2-(pyridin-2-yl)quinolin-8-ol (Lit: Ojaimi, Inorg. Chem. 2011, 50, 10966-10973) (0.05 g, 0.225 mmol) in ethanol (1 mL) was added to the reaction mixture. After that the mixture was stirred at room temperature for 2 days. The solvent was removed in vacuo. The residue was dissolved in dichloromethane and extracted with 10% NaOH solution (1×), than brine and after that water. The organic phase was dried over $Na_2SO_4$ and concentrated under reduced pressure. The title compound was isolated by preparative LC-MS providing (0.037 mg, 52%) as a yellow crystals. M.p. 136-138° C. 1H NMR (500 MHz, $CDCl_3$): δ 1.45 (d, 1H), 1.90 (dd, 5H), 2.91 (s, 2H), 3.63 (s, 2H), 4.49 (s, 2H), 7.39 (d, 1H), 7.80 (d, 1H), 7.93 (s, 1H), 8.16 (d, 1H), 8.38 (d, 1H), 8.51 (s, 2H), 9.73 (s, 1H), 11.48 (brs, 1H). 13C NMR (125 MHz, $CDCl_3$): δ 22.0, 22.7, 53.0, 54.2, 113.5, 117.8, 118.2, 122.9, 126.4, 130.2, 133.6, 138.1, 138.6, 144.3, 145.1, 149.0, 155.0.

Example 32

2-(1H-Imidazol-2-yl)-7-(piperidin-1-ylmethyl)quinolin-8-ol

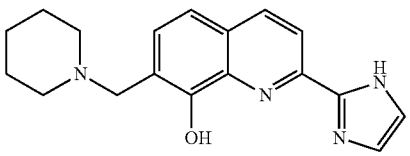 [SMILES: Oc1c(CN2CCCCC2)ccc2ccc(-c3ncc[nH]3)nc12]

The solution of piperidine (1.08 mmol) in ethanol (4 mL) was added 35% formaldehyde (1.54 mmol). The mixture was stirred for 1 hour. Then the solution of 2-(1H-imidazol-2-yl)quinolin-8-ol (prepared based on Wada, et al Chemical Communications, 2012, vol. 48, #43 p. 5340-5342) (0.2 g, 0.95 mmol) in ethanol (4 mL) was added to the reaction mixture. After that the mixture was stirred at room temperature for 3 days. The solvent was removed under reduced pressure. The residue was dissolved in dichloromethane and extracted with 10% NaOH solution (1×), than brine and after that water. The organic phase was dried over $Na_2SO_4$ and concentrated under reduced pressure. The residue was treated with ethanol to give the titled compound (0.15 g, 52%) as brownish crystals. 1H NMR (300 MHz, DMSO-$d_6$): δ 1.74 (m, 2H), 2.34 (m, 4H), 2.80 (m, 4H), 4.17 (m, 2H), 7.05 (s. 1H), 7.49 (m, 1H), 7.95 (m, 1H), 8.15 (m, 2H), 8.63 (m, 1H), 11.30 (m, 1H).

Example 33

2-[(1E)-[2-(1,3-Benzothiazol-2-yl)hydrazin-1-ylidene]methyl]-7-(piperidin-1-ylmethyl)quinolin-8-ol

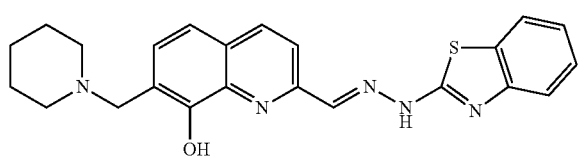 [SMILES: Oc1c(CN2CCCCC2)ccc2ccc(/C=N/Nc3nc4ccccc4s3)nc12]

The solution of piperidine (0.73 mmol) in ethanol (4 mL) was added 35% formaldehyde (1.02 mmol). The mixture was stirred for 1 hour. Then the solution of 2-[(1E)-[2-(1,3-benzothiazol-2-yl)hydrazin-1-ylidene]methyl]quinolin-8-ol (prepared based on Easmon; et al. European Journal of Medicinal Chemistry, 1997, vol. 32, #5 p. 397-408) (0.2 g, 0.63 mmol) in ethanol (4 mL) was added to the reaction mixture. After that the mixture was stirred at room temperature for 3 days. The solvent was removed in vacuo. The residue was dissolved in dichloromethane and extracted with 10% NaOH solution (1×), than brine and after that water. The organic phase was dried over $Na_2SO_4$ and concentrated under reduced pressure. The residue was treated with ethanol to give the titled compound was (0.11 g, 42%) as brownish crystals. 1H NMR (300 MHz, DMSO-$d_6$): δ 1.72 (m, 2H), 2.35 (m, 4H), 2.78 (m, 4H), 4.13 (m, 2H), 7.25 (s. 1H), 7.31 (m, 1H), 7.51 (m, 2H), 7.75-7.78 (m, 2H), 8.16 (m, 2H), 8.3 (m, 1H), 8.63 (m, 1H), 14.09 (m, 1H).

Example 34

2-[(1E)-[2-(8-Hydroxyquinolin-2-yl)hydrazin-1-ylidene]methyl]-7-(piperidin-1-ylmethyl)quinolin-8-ol

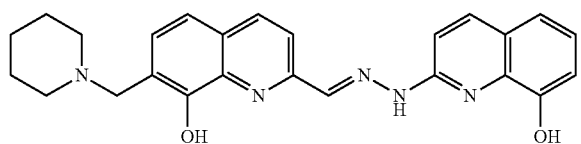 [SMILES: Oc1cccc2ccc(N/N=C/c3ccc4ccc(CN5CCCCC5)c(O)c4n3)nc12]

The solution of piperidine (0.65 mmol) in ethanol (4 mL) was added 35% formaldehyde (0.92 mmol). The mixture was stirred for 1 hour. Then the solution of 2-[(1E)-[2-(8-hydroxyquinol in-2-yl)hydrazin-1-ylidene]methyl]quinolin-8-ol (prepared based on Chaur, Manuel N.; Collado, Daniel; Lehn, Jean-Marie Chemistry—A European Journal, 2011, vol. 17, #1 p. 248-258) (0.2 g, 0.6 mmol) in ethanol (4 mL) was added to the reaction mixture. After that the mixture was stirred at room temperature for 3 days. The solvent was removed in vacuo. The residue was dissolved in dichloromethane and extracted with 10% NaOH solution (1×), than brine and after that water. The organic phase was dried over $Na_2SO_4$ and concentrated under reduced pressure. The residue was treated with ethanol to give the titled compound was (0.09 g, 35%) as brownish crystals. 1H NMR (300 MHz, DMSO-$d_6$): δ 1.74 (m, 2H), 2.33 (m, 4H), 2.81 (m, 4H), 4.08 (m, 2H), 7.05 (s. 1H), 7.12 (m, 1H), 7.24 (m, 1H), 7.35 (m, 1H), 7.68 (m, 1H), 7, 71 (m, 1H), 8.04 (m, 1H), 8.15 (m, 2H), 8.34 (m, 1H), 9.29 (s, 1H), 9.77 (s, 1H), 12.33 (b, 1H).

Example 35

5-(((2-(3-Methyl-3H-diazirin-3-yl)ethyl)(prop-2-yn-1-yl)amino)methyl)-7-(piperidin-1-ylmethyl)quinolin-8-ol

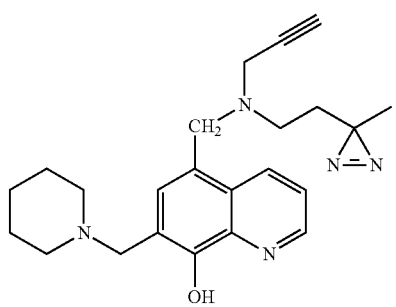 [SMILES: C#CCN(CCC1(C)N=N1)Cc1cc(CN2CCCCC2)c(O)c2ncccc12]

The solution of piperidine (0.77 mmol) in ethanol (4 mL) was added 35% formaldehyde (1.11 mmol). The mixture was stirred for 1 hour. Then the solution of 5-({[2-(3-methyl-3H-diazirin-3-yl)ethyl](prop-2-yn-1-yl)amino}methyl)quinolin-8-ol (prepared based on Lit: Cisar, J. S., & Cravatt, B. F. (2012). J. Am. Chem. Soc., 134(25), 10385-10388) (0.2 g, 0.68 mmol) in ethanol (4 mL) was added to the reaction mixture. After that the mixture was stirred at room temperature for 3 days. The solvent was removed under reduced pressure. The residue was dissolved in dichloromethane and extracted with 10% NaOH solution (1×), than brine and after that water. The organic phase was dried over $Na_2SO_4$ and concentrated under reduced pressure. The titled compound was isolated (0.18 g, 68%) as a brownish oil. 1H NMR (300 MHz, DMSO-$d_6$): δ 1.74 (m, 2H), 1.77 (m, 3H), 2.36 (m, 4H), 2.49 (m, 2H), 2.80 (m, 4H), 3.15 (s, 1H), 3.33 (m, 2H), 3.60 (m, 2H), 4.03 (m, 2H), 4.27 (m, 2H), 6.91 (s, 1H), 7.65 (m, 1H), 7.69 (m, 1H), 8.90 (m, 1H), 8.99 (m, 1H).

Example 36

7-(((2-(3-Methyl-3H-diazirin-3-yl)ethyl)(prop-2-yn-1-yl)amino)methyl)quinolin-8-ol

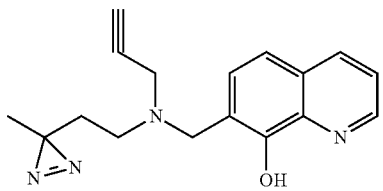 [SMILES: C#CCN(CCC1(C)N=N1)Cc1ccc2cccnc2c1O]

The solution of N-(2-(3-methyl-3H-diazirin-3-yl)ethyl) prop-2-yn-1-amine (0.100 g, 0.73 mmol) in ethanol (3 mL) was added 37% formaldehyde (36 µL, 0.029 g, 0.99 mmol) and 8-hydroxy-quinoline (0.096 g, 0.66 mmol). After that the mixture was refluxed at 60° C. for 48 hours. The reaction mixture was allowed to cool down and the solvent was removed in vacuo. The residue was dissolved in dichloromethane and extracted with 10% NaOH solution (1×), than brine and after that water. The organic phase was dried over $Na_2SO_4$ and concentrated under reduced pressure. The titled compound was isolated (0.100 g, 51%) as brown oil. 1H NMR (500 MHz, CDCl$_3$): δ 1.04 (s, 1H), 1.63 (t, 2H), 2.27 (s, 1H), 2.60 (t, 2H), 3.41 (s, 2H), 3.94 (s, 2H), 7.31 (d, 1H), 7.36-7.41 (m, 2H), 8.11 (d, 1H), 8.84 (s, 1H). 13C NMR (75 MHz, CDCl$_3$): δ 19.3, 32.3, 41.2, 48.0, 53.9, 73.9, 76.7, 117.5, 118.3, 121.4, 128.1, 128.5, 135.7, 138.5, 143.7, 148.4, 151.3. LCMS RT=6.47 min. ESI+ m/z: 295.3 [M+H+].

Example 37

7-(((2,4-Dimethoxybenzyl)amino)methyl)-5-(methylsulfonyl)quinolin-8-ol

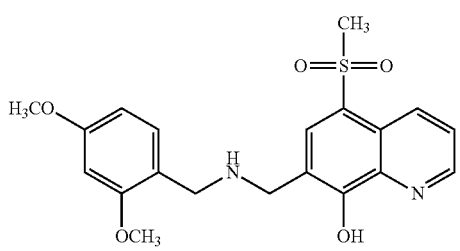 [SMILES: COc1ccc(CNCc2cc(S(C)(=O)=O)c3cccnc3c2O)c(OC)c1]

The solution of 2,4-dimethoxybenzylamine (0.183 g, 1.1 mmol) in ethanol (8 mL) was added 37% formaldehyde (41 µL, 0.033 g, 1.1 mmol) and 5-(methylsulfonyl)quinolin-8-ol (0,223 g, 1.0 mmol). After that the mixture was refluxed at 60° C. for 48 hours. The reaction mixture was allowed to cool down and the obtained precipitate was filtered off, washed with ethanol and crystallized from ethanol to give the titled compound (0.06 g, 15%) as brown crystals. Mp. 179-182° C. 1H NMR (500 MHz, DMSO-$d_6$): δ 3.14 (s, 3H), 3.76 (d, 6H), 3.83 (s, 2H), 4.02 (s, 2H), 6.49 (s, 1H), 6.55 (s, 1H), 7.22 (s, 1H), 7.58 (s, 1H), 7.97 (s, 1H), 8.78 (s, 2H). 13C NMR (75 MHz, DMSO-$d_6$): δ 45.1, 45.9, 49.0, 55.6, 55.9, 98.7, 105.0, 116.6, 123.1, 126.0, 131.4, 132.8, 141.1, 147.4, 158.9, 161.0, 166.0. LCMS RT=min. ESI+ m/z: [M+H+].

INDUSTRIAL APPLICABILITY

The objective of the present inventors was to provide compounds exhibiting improved cytotoxicity towards multidrug-resistant cells for effective inhibition of the proliferation of such cells. Furthermore, our aim was to provide new molecular entities belonging to the above-mentioned chemical class of 8-hydroxyquinolines, suitable for reversing multidrug-resistance in a cancer cell so that said cell becomes sensitive again to chemotherapeutical agents. A further objective of the present invention was to provide a method for treatment of multidrug-resistant cancer by administering the compounds of this invention in an effective concentration. A still further objective was to provide a method for treating multidrug-resistant cancer, which comprises administering a compound of the present invention simultaneously, consecutively or prior to administration of a chemotherapeutical agent for which the sensitivity of the multidrug-resistant cell has been restored by the effect of the compound according to the present invention. The above objectives have been solved according to the present invention.

REFERENCES

Betti, M. Gazz. Chim. Ital. 1903, 3311, 2.
Borst, P., 2012. Cancer drug pan-resistance: pumps, cancer stem cells, quiescence, epithelial to mesenchymal transition, blocked cell death pathways, persisters or what? Open Biology, 2(5). Available at: http://rsob.royalsocietypublishing.org/content/2/5/120066 [Accessed Jan. 7, 2013].
Enquist, P. A., et al., Bioorg Med Chem Lett, 2012. 22(10): p. 3550-3
Fernandez-Bachiller, M. I., et al., J Med Chem, 2010. 53(13): p. 4927-37.
Gillet, J.-P., Varma, S. & Gottesman, M. M., 2013. The Clinical Relevance of Cancer Cell Lines. Journal of the National Cancer Institute, 105(7), pp. 452-458.
Goldsborough, A. S. et al., 2011. Collateral Sensitivity of Multidrug-Resistant Cells to the Orphan Drug Tiopronin. Journal of Medicinal Chemistry, 54(14), pp. 4987-4997.
Gottesman, M. M., Fojo, T. & Bates, S. E., 2002. Multidrug resistance in cancer: role of ATP-dependent transporters. Nat Rev Cancer, 2, pp. 48-58.
Hall, M. D. et al., 2009. Synthesis, Activity, and Pharmacophore Development for Isatin-β-thiosemicarbazones with Selective Activity toward Multidrug-Resistant Cells. Journal of Medicinal Chemistry, 52(10), pp. 3191-3204.
Hall, M. D. et al., 2011. Synthesis and Structure—Activity Evaluation of Isatin-β-thiosemicarbazones with Improved Selective Activity toward Multidrug-Resistant Cells Expressing P-Glycoprotein. Journal of Medicinal Chemistry, 54(16), pp. 5878-5889.
Heffeter, P. et al., 2007. Multidrug-resistant cancer cells are preferential targets of the new antineoplastic lanthanum compound KP772 (FFC24). Biochemical Pharmacology, 73(12), pp. 1873-1886.
Herman T S, Cress A E, Gerner E W. Collateral sensitivity to methotrexate in cells resistant to adriamycin. Cancer Res. 1979; 39:1937-42.)
Homolya, L. et al., 1996. A new method for a quantitative assessment of P-glycoprotein-related multidrug resistance in tumour cells. Br J Cancer, 73(7), pp. 849-55.
Jansson, P. J. et al., 2015. Di-2-pyridylketone 4,4-dimethyl-3-thiosemicarbazone (Dp44mT) overcomes multidrug resistance by a novel mechanism involving the hijacking of lysosomal P-glycoprotein (Pgp). The Journal of Biological Chemistry, 290(15), pp. 9588-9603.
Kamiyama, Hirohiko et al. Personalized Chemotherapy Profiling Using Cancer Cell Lines from Selectable Mice. Clin Cancer Res 2013 19:1139-1146]
Li, L. and B. Xu, Tetrahedron, 2008. 64(49): p. 10986-10995
Libby, E. & Hromas, R., 2010. Dismounting the MDR horse. Blood, 116(20), pp. 4037-4038.
Ludwig, J. A. et al., 2006. Selective Toxicity of NSC73306 in MDR1-Positive Cells as a New Strategy to Circumvent Multidrug Resistance in Cancer. Cancer Research, 66(9), pp. 4808-4815.
Mannich, C.; Krösche, W. (1912). Archiv der Pharmazie 250: 647-667
Martin, E. W., Remington's Pharmaceutical Sciences, Mack Publishing Co., Easton, Pa., 19th Edition (1995)
M Movrin, D.; Maysinger, E. M. Pharmazie 1980, 35, 458-460).
Nakagawa-Goto, K. et al., 2010. Antitumor Agents. 280. Multidrug Resistance-Selective Desmosdumotin B Analogues. Journal of Medicinal Chemistry, 53(18), pp. 6699-6705.
Negm, N. A., S. M. Morsy, and M. M. Said, Bioorg Med Chem, 2005. 13(21): p. 5921-6
Orina, J. N. et al., 2009. Evaluation of current methods used to analyze the expression profiles of ATP-binding cassette transporters yields an improved drug-discovery database. Molecular Cancer Therapeutics, 8(7), pp. 2057-2066.
Pape V F S, Türk D, Szabó P, Wiese M, Enyedy E A, Szakács G. Synthesis and characterization of the anticancer and metal binding properties of novel pyrimidinylhydrazone derivatives. J. Inorg. Biochem. 2015; 144:18-30
Pajic, M. et al., 2009. Moderate increase in Mdr1a/1b expression causes in vivo resistance to doxorubicin in a mouse model for hereditary breast cancer. Cancer Research, 69(16), pp. 6396-6404.
Petitjean, A., N. Kyritsakas, and J. M. Lehn, Chemistry—a European Journal, 2005. 11(23): p. 6818-28.)
N. Risch et al. Angew. Chem. Int. Ed. 1998, 37, 1044-1070.
Rottenberg, S. & Borst, P., Drug resistance in the mouse cancer clinic. Drug Resistance Updates, (0). Available at: http://www.sciencedirect.com/science/article/pii/S1368764612000027 [Accessed Feb. 20, 2012].
Sarkadi, B. et al., 2006. Human multidrug resistance ABCB and ABCG transporters: participation in a chemoimmunity defense system. Physiological Reviews, 86(4), pp. 1179-1236.
Shaw, A. Y., et al., Eur J Med Chem, 2010. 45(7): p. 2860-7
Sosic, I., et al., J Med Chem, 2013. 56(2): p. 521-33.
Szakács, G., Annereau, J.-P., Lababidi, S., Shankavaram, U., Arciello, A., Bussey, K. J., et al., 2004. Predicting drug sensitivity and resistance: profiling ABC transporter genes in cancer cells. Cancer cell, 6(2), pp. 129-137.
Szakács, G., Annereau, J.-P., Lababidi, S., Shankavaram, U., Arciello, A., Bussey, K. J., et al., 2004. Predicting drug sensitivity and resistance: profiling ABC transporter genes in cancer cells. Cancer Cell, 6(2), pp. 129-137.

Szakacs, G. et al., 2006. Targeting multidrug resistance in cancer. Nat Rev Drug Discov, 5(3), pp. 219-34.
Szakács, G. et al., 2014. Targeting the Achilles Heel of Multidrug-Resistant Cancer by Exploiting the Fitness Cost of Resistance. Chemical Reviews, p. 140423154337000.
Szatmári, I., L. Lazar, and F. Fülöp, Tetrahedron Letters, 2006. 47(23): p. 3881-3883)
Szatmári, I. and F. Fülöp, Tetrahedron, 2013. 69(4): p. 1255-1278.).
Szybalski, W. & Bryson, V., 1952. Genetic studies on microbial cross resistance to toxic agents. I. Cross resistance of *Escherichia coli* to fifteen antibiotics. Journal of bacteriology, 64(4), pp. 489-499.
Terry, Rudolph F. Przystal J. P. Phillips, J. Med. Chem., 1967, 10 (5), pp 981-981 September 1967)
Tramontini, M, Angiolini, L, Mannich-Bases, Chemistry and Uses, CRC, Boca Raton, Fla., 1994)
Türk, D. et al., 2009. Identification of Compounds Selectively Killing Multidrug-Resistant Cancer Cells. Cancer Research, 69(21), pp. 8293-8301.
Türk, D. & Szakács, G., 2009. Relevance of multidrug resistance in the age of targeted therapy. Current Opinion in Drug Discovery & Development, 12(2), pp. 246-252.
Ujhelly O, Ozvegy C, Varady G, et al. Application of a human multidrug transporter (ABCG2) variant as selectable marker in gene transfer to progenitor cells. Hum Gene Ther,14 pp 403-12.
Wangtrakuldee, P., et al., ACS Med Chem Lett, 2013. 4(8)
Wu, Qiong et al. Multidrug-resistance in cancer chemotherapeutics: Mechanisms and lab approaches. Cancer Letters 347(2) 2014, 159-166

We claim:

1. A compound of Formula I,

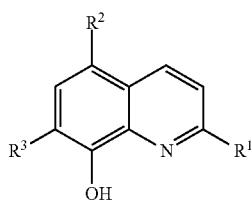

Formula I wherein
$R^1$ is selected from the group consisting of hydrogen, methyl, 1-(2-hydroxyphenyl)-ethylidene]-hydrazin-1-yl, 1-(pyridin-2-yl)-ethylidene]-hydrazin-1-yl, 2-[(E/Z)-2-[1-(pyridin-2-yl)-ethylidene]hydrazin-1-yl, 2-[(pyridin-2-yl)-methylidene]-hydrazin-1-yl, ((benzothiazol-2-yl)-hydrazin-1-ylidene)-methyl, 2-(8-hydroxyquinolin-2-yl)-hydrazin-1-ylidene)methyl, thiosemicarbamoyl-1-(4-methoxyphenyl) and pyridine-2-yl, imidazole-2-yl;
$R^2$ is selected from the group consisting of hydrogen, nitro, $(C_1-C_6)$alkylsulfonyl, pyridinyl, imidazolyl and halogen,
$R^3$ is selected from the group consisting of (piperidin-1-yl)methyl, cyclohexylaminomethyl, (4-methoxybenzyl)-amino-methyl, (2-methoxybenzyl)-amino-methyl, (2,4-dimethoxybenzyl)-amino-methyl, 3,4-dimethoxybenzyl-aminomethyl, (2-fluorobenzyl)-aminomethyl, ethyl-2-{[(2-fluorophenyl)methyl]amino}acetate, {1H,2H,3H,4H,9H-pyrido[3,4-b]indol-1-yl}, {4H,5H,6H,7H-tetrahydrothieno[3,2-c]pyridin-4-yl}, 1,2,3,4-tetrahydroisoquinolin-1-yl, 6,7-dimethoxy-1,2,3,4-tetrahydroisoquinolin-1-yl, (pyridin-3-yl)[(1,3-thiazol-2-yl)amino]methyl, benzyl-amino-methyl and octahydroquinoxalin-2(1H)-one;
with the provisos that
when $R^1$ and $R^2$ are hydrogen, $R^3$ is different from (piperidine-1-yl)-methyl, 1,2,3,4-tetrahydro-isoquionoline-1-yl and 6,7-dimethoxy-1,2,3,4-tetrahydroisoquionoline-1-yl;
when $R^1$ is hydrogen, $R^2$ is nitro, $R^3$ is different from benzylamino-methyl, (piperidine-1-yl)-methyl;
when $R^1$ is methyl and $R^2$ is hydrogen, $R^3$ is different from (piperidine-1-yl)-methyl, 1,2,3,4-tetrahydro-isoquionoline-1-yl and 6,7-dimethoxy-1,2,3,4-tetrahydroisoquionoline-1-yl; and
when $R^1$ is hydrogen and $R^2$ is halogen, $R^3$ is different from benzylamino-methyl and (piperidine-1-yl)-methyl;

or a stereoisomer, pharmaceutically acceptable salt, solvate or metal complex thereof.

2. The compound according to claim 1, wherein the compound has P-gp-potentiated MDR selectivity whereby it is capable of killing P-gp-expressing multidrug-resistant cells and wherein the compound is capable of reducing expression of P-gp in a population of P-gp-expressing cells.

3. The compound according to claim 1, wherein
$R^3$ is selected from the group consisting of cyclohexylamino-methyl, (4-methoxybenzyl)-amino-methyl, (2-methoxybenzyl)-amino-methyl, (2,4-dimethoxybenzyl)-amino-methyl, 3,4-dimethoxybenzyl-amino-methyl, (2-fluorobenzyl)-amino-methyl, ethyl-2-{[(2-fluorophenyl)methyl]amino}acetate, {1H,2H,3H,4H,9H-pyrido[3,4-b]indol-1-yl}, {4H,5H,6H,7H-tetrahydrothieno[3,2-c]pyridin-4-yl}, 1,2,3,4-tetrahydroisoquinolin-1-yl, 6,7-dimethoxy-1,2,3,4-tetrahydroisoquinolin-1-yl, (pyridin-3-yl)[(1,3-thiazol-2-yl)amino]methyl and benzyl-amino-methyl.

4. The compound according to claim 1, wherein
$R^1$ is selected from the group consisting of 1-(2-hydroxyphenyl)-ethylidene]-hydrazin-1-yl, 1-(pyridin-2-yl)-ethylidene]-hydrazin-1-yl, 2-[(E/Z)-2-[1-(pyridin-2-yl)-ethylidene]hydrazin-1-yl, (Z)-2-[(pyridin-2-yl)-methylidene]-hydrazin-1-yl, (benzothiazol-2-yl)-hydrazin-1-ylidene)-methyl, 2-(8-hydroxyquinolin-2-yl)-hydrazin-1-ylidene)methyl, thiosemicarbamoyl-1-(4-methoxyphenyl) and pyridine-2-yl, imidazole-2-yl.

5. A compound of Formula I,

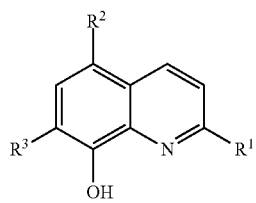

Formula I wherein
$R^1$ is selected from the group consisting of hydrogen, methyl, 1-(2-hydroxyphenyl)-ethylidene]-hydrazin-1-yl, 1-(pyridin-2-yl)-ethylidene]-hydrazin-1-yl, 2-[(E/Z)-2-[1-(pyridin-2-yl)-ethylidene]hydrazin-1-yl, 2-[(pyridin-2-yl)-methylidene]-hydrazin-1-yl, ((benzothiazol-2-yl)-hydrazin-1-ylidene)-methyl, 2-(8-hydroxyquinolin-2-yl)-hydrazin-1-ylidene)methyl, thiosemicarbamoyl-1-(4-methoxyphenyl) and pyridine-2-yl, imidazole-2-yl;

R² is selected from the group consisting of hydrogen, nitro, (C₁-C₆)alkylsulfonyl, pyridinyl, imidazolyl and halogen, R³ is selected from the group consisting of (piperidin-1-yl)methyl, cyclohexylaminomethyl, (4-methoxybenzyl)-amino-methyl, (2-methoxybenzyl)-amino-methyl, (2,4-dimethoxybenzyl)-amino-methyl, 3,4-dimethoxybenzyl-amino-methyl, (2-fluorobenzyl)-aminomethyl, ethyl-2-{[(2-fluorophenyl)methyl]amino}acetate, {1H,2H,3H,4H,9H-pyrido[3,4-b]indol-1-yl}, {4H,5H,6H,7H-tetrahydrothieno[3,2-c]pyridin-4-yl}, 1,2,3,4-tetrahydroisoquinolin-1-yl, 6,7-dimethoxy-1,2,3,4-tetrahydroisoquinolin-1-yl, (pyridin-3-yl)[(1,3-thiazol-2-yl)amino]methyl, benzyl-amino-methyl and octahydroquinoxalin-2(1H)-one;

wherein said compound is selected from the group consisting of
7-(((2,4-dimethoxybenzyl)amino)methyl)-5-(methylsulfonyl)quinolin-8-ol;
7-(((3,4-dimethoxybenzyl)amino)methyl)-5-nitroquinolin-8-ol;
7-(((2-methoxybenzyl)amino)methyl)-5-nitroquinolin-8-ol;
7-(((2,4-dimethoxybenzyl)amino)methyl)-5-nitroquinolin-8-ol;
7-(((4-methoxybenzyl)amino)methyl)-5-nitroquinolin-8-ol;
(3R,4aS,8aS)-3-(5-chloro-8-hydroxyquinolin-7-yl)octahydroquinoxalin-2(1H)-one;
(3S,4aS,8aS)-3-(5-chloro-8-hydroxyquinolin-7-yl)octahydroquinoxalin-2(1H)-one;
5-bromo-7-(((3,4-dimethoxybenzyl)amino)methyl)quinolin-8-ol;
5-chloro-7-(((2,4-dimethoxybenzyl)amino)methyl)quinolin-8-ol;
(E/Z)-7-(piperidin-1 ylmethyl)-2-(2-(1-(pyridin-2-yl)ethylidene)hydrazinyl)quinolin-8-ol;
(E/Z)-2-(2-(1-(2-hydroxyphenyl)ethylidene)hydrazinyl)-7-(piperidin-1-ylmethyl)quinolin-8-ol;
(E/Z)-7-(piperidin-1-ylmethyl)-2-(2-(pyridine-2-ylmethylene)hydrazinyl)quinolin-8-ol;
5-chloro-7-((cyclohexylamino)methyl)quinolin-8-ol;
5-chloro-7-(((4-methoxybenzyl)amino)methyl)quinolin-8-ol;
5-bromo-7-(((2-methoxybenzyl)amino)methyl)quinolin-8-ol;
5-bromo-7-(((2,4-dimethoxybenzyl)amino)methyl)quinolin-8-ol;
5-bromo-7-(((4-methoxybenzyl)amino)methyl)quinolin-8-ol;
5-chloro-7-({[(2-fluorophenyl)methyl]amino}methyl)quinolin-8-ol;
5-chloro-7-(1,2,3,4-tetrahydroisoquinolin-1-yl)quinolin-8-ol;
5-bromo-7-(1,2,3,4-tetrahydroisoquinolin-1-yl)quinolin-8-ol;
5-nitro-7-(1,2,3,4-tetrahydroisoquinolin-1-yl)quinolin-8-ol;
5-chloro-7-(6,7-dimethoxy-1,2,3,4-tetrahydroisoquinolin-1-yl)quinolin-8-ol;
5-chloro-7-(4,5,6,7-tetrahydrothieno[3,2-c]pyridin-4-yl)quinolin-8-ol;
7-(4,5,6,7-tetrahydrothieno[3,2-c]pyridin-4-yl)quinolin-8-ol;
5-nitro-7-(4,5,6,7-tetrahydrothieno[3,2-c]pyridin-4-yl)quinolin-8-ol and
2-(2-methyl-7-{4,5,6,7-tetrahydrothieno[3,2-c]pyridin-4-yl}quinolin-8-ol or a stereoisomer, pharmaceutically acceptable salt, solvate or metal complex thereof.

6. A compound of Formula I,

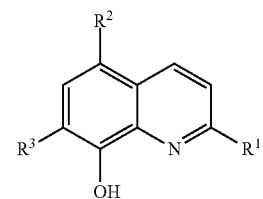

Formula I wherein

R¹ is selected from the group consisting of hydrogen, methyl, 1-(2-hydroxyphenyl)-ethylidene]-hydrazin-1-yl, 1-(pyridin-2-yl)-ethylidene]-hydrazin-1-yl, 2-[(E/Z)-2-[1-(pyridin-2-yl)-ethylidene]hydrazin-1-yl, 2-[(pyridin-2-yl)-methylidene]-hydrazin-1-yl, (benzothiazol-2-yl)-hydrazin-1-ylidene)-methyl, 2-(8-hydroxyquinolin-2-yl)-hydrazin-1-ylidene) methyl, thiosemicarbamoyl-1-(4-methoxyphenyl) and pyridine-2-yl, imidazole-2-yl;

R² is selected from the group consisting of hydrogen, nitro, (C₁-C₆)alkylsulfonyl, pyridinyl, and imidazolyl, R³ is selected from the group consisting of (piperidin-1-yl)methyl, cyclohexylamino-methyl, (4-methoxybenzyl)-amino-methyl, (2-methoxybenzyl)-amino-methyl, (2,4-dimethoxybenzyl)-amino-methyl, 3,4-dimethoxybenzyl-amino-methyl, (2-fluorobenzyl)-aminomethyl, ethyl-2-{[(2-fluorophenyl)methyl]amino}acetate, {1H,2H,3H,4H,9H-pyrido[3,4-b]indol-1-yl}, {4H,5H,6H,7H-tetrahydrothieno[3,2-c]pyridin-4-yl}, 1,2,3,4-tetrahydroisoquinolin-1-yl, 6,7-dimethoxy-1,2,3,4-tetrahydroisoquinolin-1-yl, (pyridin-3-yl)[(1,3-thiazol-2-yl)amino]methyl and benzyl-amino-methyl;

with the proviso that
when R¹ and R² are hydrogen, R³ is different from (piperidine-1-yl)-methyl, 1,2,3,4-tetrahydroisoquionoline-1-yl and 6,7-dimethoxy-1,2,3,4-tetrahydroisoquionoline-1-yl;
when R¹ is hydrogen and R² is nitro, R³ is different from benzylamino-methyl and (piperidine-1-yl)-methyl;
when R¹ is methyl and R² is hydrogen, R³ is different from (piperidine-1-yl)-methyl, 1,2,3,4-tetrahydro-isoquionoline-1-yl and 6,7-dimethoxy-1,2,3,4-tetrahydroisoquionoline-1-yl;

or a stereoisomer, pharmaceutically acceptable salt, solvate or metal complex thereof.

7. A method for reducing expression of P-gp in P-gp expressing multidrug-resistant cells, said method comprising administering a compound of the Formula I according to claim 1 to a patient in need.

8. The method according to claim 7, wherein said compound reduces expression of P-gp in P-gp-expressing multidrug-resistant cells so that the ratio of non-P-gp-expressing cells is at least 20% after the first dose of said compound.

9. The method according to claim 7, where the compound is administered in combination with a second therapeutical agent wherein the second therapeutical agent is a chemotherapeutical agent or an anticancer antibody.

10. The method of claim 9 wherein the second therapeutical agent is a chemotherapeutical agent for the treatment of multidrug-resistant and/or metastatic cancer.

11. The method according to claim 7 where the compound is administered in combination with a second therapeutical agent in the treatment of multidrug-resistant cancer, wherein the second therapeutical agent is administered simultaneously with or subsequently to said compound.

12. The method according to claim 7 where the compound is applied in combination with a second therapeutical agent which is a chemotherapeutical agent in the treatment of cancer, wherein the second therapeutical agent is a chemotherapeutical agent selected from the group consisting of alkylating agents, alkylating-like agents, alkylating-like agents, antimetabolites, anti-microtubule agents, topoisomerase inhibitors and cytotoxic antibiotics.

13. The method according to claim 7 comprising
a therapeutic regimen wherein
  a) the compound of Formula I is administered for a given period of time thereby killing P-gp-expressing cells and arriving at a non-P-gp-expressing phenotype in surviving tumor cells,
  b) a chemotherapeutic compound transportable by P-gp is administered thereby killing the surviving tumor cells of non-P-gp-expressing phenotype and
  c) optionally in a further stage of treatment one or both of a further P-gp-potentiated MDR selective compound of Formula I and a further cytotoxic chemotherapeutic compound is/are administered as defined in steps a) and b).

14. The method of claim 7 wherein the patient suffers from a multidrug-resistant cancer or a multidrug-resistant metastatic cancer selected from the group consisting of sarcomas and carcinomas including fibrosarcoma, myxosarcoma, liposarcoma, chondrosarcoma, osteogenic sarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, tumors of the CNS system including glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma, prostate, breast, colon, bladder, cervical, skin, testicular, kidney, ovarian, stomach, brain, liver, pancreatic or esophageal cancer, lymphoma, leukemia including acute lymphocytic leukemia, acute myelocytic leukemia, acute myelogenous leukemia and myeloblasts, promyelocytic, myelomonocytic, monocytic and erythroleukemia, chronic myelocytic (granulocytic) leukemia, chronic myelogenous leukemia, chronic lymphocytic leukemia, polycythemia vera, lymphoma, Hodgkin's disease, non-Hodgkin's lymphoma, multiple myeloma, Waldenstrom's macro globulinemia, heavy chain disease, myelodysplastic syndrome, hairy cell leukemia and myelodysplasia.

15. A method for reducing expression of P-gp in P-gp expressing multidrug-resistant cells, said method comprising administering a compound of the Formula I according to claim 5 to a patient in need.

\* \* \* \* \*